US009132130B2

(12) United States Patent
Suzuki et al.

(10) Patent No.: US 9,132,130 B2
(45) Date of Patent: Sep. 15, 2015

(54) PURINE DERIVATIVE AND ANTITUMOR AGENT USING SAME

(75) Inventors: Toshiaki Suzuki, Tokyo (JP); Hideki Satoh, Tokyo (JP); Toshiyuki Matsuno, Tokyo (JP); Kenichi Saitoh, Tokyo (JP); Soichi Ohta, Tokyo (JP); Manami Masuda, Tokyo (JP); Shinichi Yaguchi, Tokyo (JP); Ichiro Koshimizu, Tokyo (JP); Yuriko Watanabe, Tokyo (JP); Yoshie Minowa, Tokyo (JP); Masayuki Takahashi, Tokyo (JP); Tomoyoshi Kayou, Tokyo (JP)

(73) Assignee: ZENYAKU KOGYO KABUSHIKI KAISHA, Tokyo (JP)

( * ) Notice: Subject to any disclaimer, the term of this patent is extended or adjusted under 35 U.S.C. 154(b) by 482 days.

(21) Appl. No.: 13/266,681

(22) PCT Filed: Apr. 28, 2010

(86) PCT No.: PCT/JP2010/057614
§ 371 (c)(1),
(2), (4) Date: Dec. 16, 2011

(87) PCT Pub. No.: WO2010/126101
PCT Pub. Date: Nov. 4, 2010

(65) Prior Publication Data
US 2012/0088765 A1    Apr. 12, 2012

(30) Foreign Application Priority Data
Apr. 28, 2009 (JP) .................................. 2009-108781

(51) Int. Cl.
*A61K 31/52* (2006.01)
*C07D 473/36* (2006.01)
*C07D 487/12* (2006.01)
*C07D 473/24* (2006.01)
*A61K 31/5377* (2006.01)

(52) U.S. Cl.
CPC ............. *A61K 31/52* (2013.01); *A61K 31/5377* (2013.01); *C07D 473/24* (2013.01)
USPC ........ 514/263.2; 544/245; 544/256; 544/265; 514/247; 514/258.1; 514/262.1

(58) Field of Classification Search
CPC .............................. A61K 31/52; C07D 473/36
USPC .................. 544/245, 256, 264, 265; 514/247, 514/258.1, 262.1, 263.2
See application file for complete search history.

(56) References Cited

U.S. PATENT DOCUMENTS

| 6,329,381 | B1 * | 12/2001 | Kurimoto et al. ........ 514/263.23 |
| 6,734,187 | B1 * | 5/2004 | Ono et al. ................ 514/263.22 |
| 7,189,730 | B2 * | 3/2007 | Cristalli .................. 514/263.22 |
| 7,754,728 | B2 * | 7/2010 | Isobe et al. ................ 514/263.2 |
| 8,148,371 | B2 * | 4/2012 | Isobe et al. ................ 514/234.2 |
| 2003/0149060 | A1 | 8/2003 | Cristalli |
| 2009/0181989 | A1 | 7/2009 | Brough et al. |

FOREIGN PATENT DOCUMENTS

| CN | 101602765 | 12/2009 |
| JP | S49-18889 A | 2/1974 |
| JP | 52 71492 | 6/1977 |
| JP | 11 180981 | 7/1999 |
| JP | 2008 516938 | 5/2008 |
| WO | 99 28321 | 6/1999 |
| WO | WO 01/44259 A1 | 6/2001 |
| WO | WO 01/62768 A1 | 8/2001 |
| WO | 03 051882 | 6/2003 |
| WO | 2007 034185 | 3/2007 |

OTHER PUBLICATIONS

Cristalli et al (2003): STN International HCAPLUS database, Columbus (OH), Accession No. 2003:491228.*
Extended European Search Report issued Aug. 30, 2012 in European Patent Application No. 10769799.7.
Wignall, S.M., et al., "Identification of a Novel Protein Regulating Microtubule Stability through a Chemical Approach," Chemistry and Biology, vol. 11, pp. 136-146, (Jan. 2004).
Berge, S.M., et al., "Pharmaceutical Salts," Journal of Pharmaceutical Sciences, vol. 66, No. 1, Total 19 Pages, (Jan. 1977).
International Search Report Issued Jun. 29, 2010 in PCT/JP10/57614 Filed Mar. 28, 2010.
Office Action as received in the corresponding Japanese Patent Application No. 2011-511448 dated Oct. 21, 2014 w/English Translation.
Mono Ikehara, et al., Chemical & Pharmaceutical Bulletin, 1962, 10, pp. 665-669.

* cited by examiner

*Primary Examiner* — Golam M M Shameem
(74) *Attorney, Agent, or Firm* — Oblon, McClelland, Maier & Neustadt, L.L.P.

(57) ABSTRACT

Disclosed are: a novel purine derivative, a composition thereof, a method for treating tumor using the purine derivative, and an antitumor agent using the purine derivative. Specifically disclosed is a compound represented by formula (I), or a pharmaceutically acceptable salt, solvate or hydrate thereof, or a prodrug thereof.

15 Claims, No Drawings

PURINE DERIVATIVE AND ANTITUMOR AGENT USING SAME

This application is a National Stage of PCT/JP10/057614 filed Apr. 28, 2010 and claims the benefit of JP 2009-108781 filed Apr. 28, 2009.

TECHNICAL FIELD

The present invention relates to a purine derivative and a composition thereof, as well as an antitumor agent and a method for treating tumor using the purine derivative.

BACKGROUND ART 6-mercaptopurine, which is currently used as an antitumor agent, was discovered by Hitchings et al. in 1948 during studies on antimetabolites and synthesized by Elion et al. in 1952 from hypoxanthine. Clarke and Law et al. experimentally confirmed its antitumor effect in 1953, Burchenal et al. applied it clinically for the first time in 1953, and its superior effects were not only recognized in childhood acute leukemia, but also in adult acute leukemia. For that reason, among the numerous known chemotherapeutic agents for leukemia, it was the first substance to be called an anti-leukemic drug. Additionally, it is also used in an early stage and late stage of chronic leukemia, and is known to be effective.

6-mercaptopurine is a orally-effective nucleic acid antimetabolite for treating leukemia, and has been used to ameliorate subjective and objective symptoms of acute leukemia and chronic myeloid leukemia. However, it is known to have side effects including severe myelosuppression, liver dysfunction and hypersensitivity, and when considering patients' life of quality (QOL), they are issues that must be solved.

Moreover, the agent has also been used as an antimetabolite immunosuppressant, and has been used in Predonine non-responders and in cases where it is difficult to reduce the amount of or to go off Predonine. Since it takes three to four months before the effects are apparent, there is a need to watch for side effects. Further, due to myelosuppression as a side effect, infections tend to occur and renal dysfunction develops easily. Additionally, since resistance is weakened, all kinds of bacterial infections including colds occur easily. There is also a possibility for various complications to occur in conjunction.

Non-patent document 1: *Chemistry & Biology*, Vol. 11, 135-146, January 2004.

Patent document 1: WO 99/28321

SUMMARY OF THE INVENTION

The development of a purine derivative having a strong antitumor activity and an antitumor agent using the derivative was desired. Consequently, the object of the present invention is to provide a novel purine derivative and a composition as well as an antitumor agent and a method for treating tumor using the purine derivative.

The present inventors, as a result of searching for antitumor agents, found a purine derivative with a strong antitumor activity.

In other words, according to the present invention, a purine derivative, or a pharmaceutically acceptable salt, solvate or hydrate thereof is provided. The above purine derivative is a compound represented by the general formula (I) below:

[Chem. 1]

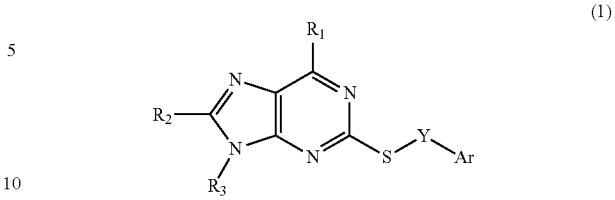

In the above formula (I), Ar represents a phenyl group, pyridyl group, thiazolyl group, benzofuranyl group, dihydrobenzofuranyl group, naphthalenyl group, imidazolyl group or pyrazolyl group. Additionally, the above phenyl group, pyridyl group, thiazolyl group, benzofuranyl group, dihydrobenzofuranyl group, naphthalenyl group, imidazolyl group or pyrazolyl group may be independently substituted with one, two or three halogens, formyl groups, cyano groups, nitro groups, amino groups, hydroxyl groups, carboxyl groups, (C1-C6) alkyl groups, (C2-C6) alkenyl groups, (C1-C6) alkylcarbonyl groups, (C1-C6) alkylamino groups, (C1-C6) alkylcarbonylaminocarbonyl groups, (C3-C6) cycloalkylamino groups, (C1-C7) alkoxycarbonylamino groups, di[(C1-C6) alkyl]amino groups, (C1-C6) alkylcarbonylamino groups, (C3-C6) cycloalkylcarbonylamino groups, di[(C1-C6) alkyl]aminocarbonylamino groups, di[(C1-C6) alkyl]aminothiocarbonylamino groups, heteroarylcarbonylamino groups, phenyloxycarbonylamino groups, phenylcarbonylamino groups, (C1-C6) alkylsulfonylamino groups, di[(C1-C6) alkyl]aminosulfonylamino groups, (C1-C6) alkoxy groups, (C1-C6) alkylthio groups, (C1-C6) alkylenedioxy groups, (C1-C6) alkoxycarbonyl groups, amino(C1-C6) alkylcarbonylamino groups, phenyl(C2-C6) alkenylcarbonylamino groups, (C1-C6) alkoxy(C1-C6) alkylcarbonylamino groups, (C1-C6) alkoxycarbonylamino (C1-C6) alkylcarbonylamino groups, phenyl groups or phenyl(C1-C6) alkoxy groups. Moreover, the above (C1-C6) alkyl group, (C2-C6) alkenyl group, (C1-C6) alkylcarbonyl group, (C1-C6) alkylamino group, (C1-C6) alkylcarbonylaminocarbonyl group, (C3-C6) cycloalkylamino group, (C1-C7) alkoxycarbonylamino group, di[(C1-C6) alkyl]amino group, (C1-C6) alkylcarbonylamino group, (C3-C6) cycloalkylcarbonylamino group, di[(C1-C6) alkyl]aminocarbonylamino group, di[(C1-C6) alkyl]aminothiocarbonylamino group, heteroarylcarbonylamino group, phenyloxycarbonylamino group, phenylcarbonylamino group, (C1-C6) alkylsulfonylamino group, di[(C1-C6) alkyl]aminosulfonylamino group, (C1-C6) alkoxy group, (C1-C6) alkylthio group, (C1-C6) alkylenedioxy group, (C1-C6) alkoxycarbonyl group, amino(C1-C6) alkylcarbonylamino group, phenyl(C2-C6) alkenylcarbonylamino group, (C1-C6) alkoxy(C1-C6) alkylcarbonylamino group, (C1-C6) alkoxycarbonylamino(C1-C6) alkylcarbonylamino group, phenyl group or phenyl(C1-C6) alkoxy group may be further substituted with a halogen, cyano group, amino group, hydroxyl group or carboxyl group.

In the above formula (I), Y represents a (C1-C6) alkylene group. Additionally, the above (C1-C6) alkylene group may comprise a carbonyl group in the carbon chain. Moreover, the above (C1-C6) alkylene group may be substituted with one or two of Ar.

In the above formula (I), $R_1$ represents a (C1-C6) alkyl group, (C2-C6) alkenyl group, amino group, (C1-C6) alkylcarbonylamino group, heterocyclic group or phenyl group. Additionally, the above amino group or (C1-C6) alkylcarbonylamino group may be substituted with one or two (C1-C6) alkyl groups, (C1-C6) alkoxy groups, (C1-C6) alkoxy(C1-C6) alkyl groups, (C3-C6) cycloalkyl groups or (C2-C6) alkenyl groups. Moreover, the above heterocyclic group may be substituted with one or two nitroso groups, formyl groups, hydroxyl groups, (C1-C6) alkyl groups, (C1-C6) alkylcarbonyl groups, (C1-C6) alkoxy groups, (C1-C6) alkoxycarbonyl groups or hydroxy (C1-C6) alkylamino groups. In addition, the above phenyl group may be substituted with one or two halogens, formyl groups, cyano groups, nitro groups, amino groups, hydroxyl groups, or carboxyl groups.

In the above formula (I), $R_2$ represents H, a (C1-C6) alkyl group, (C2-C6) alkenyl group, (C2-C6) alkynyl group or (C3-C6) cycloalkyl group. Additionally, the above (C1-C6) alkyl group, (C2-C6) alkenyl group, (C2-C6) alkynyl group or (C3-C6) cycloalkyl group may be substituted with one or two halogens, nitro groups or amino groups.

In the above formula (I), $R_3$ represents a (C1-C6) alkyl group, (C2-C6) alkenyl group, (C2-C6) alkynyl group, (C3-C6) cycloalkyl group, (C3-C6) cycloalkyl(C1-C6) alkyl group, amino(C1-C6) alkyl group, three to five-membered cyclic ether-(C1-C6) alkyl group or (C1-C6) alkylcarbonylamino(C1-C6) alkyl group. Moreover, the above (C1-C6) alkyl group, (C2-C6) alkenyl group, (C2-C6) alkynyl group, (C3-C6) cycloalkyl group, (C3-C6) cycloalkyl(C1-C6) alkyl group, amino(C1-C6) alkyl group, three to five-membered cyclic ether-(C1-C6) alkyl group or (C1-C6) alkylcarbonylamino(C1-C6) alkyl group may be substituted with halogen or a hydroxyl group.

In addition, according to the present invention, a composition comprising the above purine derivative or a pharmaceutically acceptable salt, solvate or hydrate thereof, or a prodrug thereof, and a pharmaceutically acceptable adjuvant, diluent or carrier is provided.

Moreover, according to the present invention, a pharmaceutical composition for treating tumor comprising the above purine derivative or a pharmaceutically acceptable salt, solvate or hydrate thereof, or a prodrug thereof is provided.

Additionally, according to the present invention, an antitumor agent comprising the above purine derivative or a pharmaceutically acceptable salt, solvate or hydrate thereof, or a prodrug thereof is provided.

Moreover, according to the present invention, a method for treating tumor comprising administering to a patient (in need thereof) the above purine derivative or a pharmaceutically acceptable salt, solvate or hydrate thereof, or a prodrug thereof is provided.

Further, according to the present invention, the above purine derivative or a pharmaceutically acceptable salt, solvate or hydrate thereof, or a prodrug thereof for use in the treatment of a tumor is provided.

Furthermore, according to the present invention, the above purine derivative or a pharmaceutically acceptable salt, solvate or hydrate thereof, or a prodrug thereof for use in the preparation of a medicament for treating tumor is provided.

MODES FOR CARRYING OUT THE INVENTION

[Explanation of Terminology]

In the present specification, the following terms have the meanings indicated below.

The term "halogen" or "halo" refers to fluorine, chlorine, bromine or iodine.

The term "hydroxyl" refers to a —OH group.

The term "cyano" refers to a —CN group.

The term "carboxyl" refers to a —(C=O)OH group.

The term "amino" refers to a —NH$_2$ group, or a divalent or trivalent group in which hydrogen is substituted with another atom.

The term "nitro" refers to a —NO$_2$ group.

The term "nitroso" refers to a —NO group.

The term "formyl" refers to a —(C=O)H group.

The term "sulfonyl" refers to a —S(=O)$_2$— group, which is a divalent group.

The term "carbonyl" refers to a -(C=O)— group, which is a divalent group.

The term "thiocarbonyl" refers to a —(C=S)— group, which is a divalent group.

The term "alkyl", "alkenyl", "alkynyl" and "cycloalkyl" refer to not only univalent groups, but also divalent groups and groups of higher valence in some cases. For example, when referring to divalent groups, they are respectively used in the same meaning as "alkylene", "alkenylene", "alkynylene" and "cycloalkylene".

The prefixes of the terms "(Cx-Cy) alkyl", "(Cx-Cy) alkenyl", "(Cx-Cy) alkynyl" and "(Cx-Cy) cycloalkyl" refer to groups each having x to y number of carbon atoms.

Additionally, regarding arbitrary polyvalent groups, in cases of substitution at sites where single rings or multiple rings can be formed, unless particularly limited, the polyvalent groups may form ring structures.

The terms "(C1-C6) alkyl" and "(C1-C6) alkylene" refer to branched or linear saturated hydrocarbon groups having one to six carbon atoms, and include, for example, (C1-C3) alkyl, (C1-C4) alkyl, (C1-C6) alkyl, (C2-C6) alkyl and (C3-C6) alkyl. Representative (C1-C6) alkyl groups include, for example, methyl, ethyl, propyl [e.g., propan-1-yl, propan-2-yl (or iso-propyl)], butyl [e.g., 2-methylpropan-2-yl (or tert-butyl), butan-1-yl, butan-2-yl], pentyl (e.g., pentan-1-yl, pentan-2-yl, pentan-3-yl), 2-methylbutan-1-yl, 3-methylbutan-1-yl and hexyl (e.g., hexan-1-yl).

The terms "(C2-C6) alkenyl" and "(C2-C6) alkenylene" refer to linear or branched non-aromatic hydrocarbon groups having two to six carbon atoms and at least one carbon-carbon double bond, and include, for example, (C2-C3) alkenyl, (C2-C4) alkenyl, (C2-C6) alkenyl, (C3-C6) alkenyl and (C4-C6) alkenyl. Representative (C2-C6) alkenyl groups include, for example, vinyl, 1-propenyl, 2-propenyl, iso-propenyl, 1,3-butadienyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 2,4-hexadienyl, and 5-hexenyl.

The terms "(C2-C6) alkynyl" and "(C2-C6) alkynylene" refer to linear or branched non-aromatic hydrocarbon groups having two to six carbon atoms and at least one carbon-carbon triple bond, and include, for example, (C2-C3) alkynyl, (C2-C4) alkynyl, (C2-C6) alkynyl, (C3-C6) alkynyl and (C4-C6) alkynyl. Representative (C2-C6) alkynyl groups include, for example, ethynyl, 1-propynyl, 2-propynyl, iso-propynyl, 1-budienyl, 2-budienyl, 3-budienyl, 2-methyl-1-propynyl, 1-pentynyl, 2-pentynyl, 3-pentynyl, 4-pentynyl, 3-methyl-2-butynyl, 1-hexynyl, 2-hexynyl, 3-hexynyl, and 5-hexynyl.

The term "(C3-C6) cycloalkyl" refers to a saturated monocyclic carbon ring having three to six carbon atoms. Representative (C3-C6) cycloalkyls include, for example, cyclopropyl, cyclobutyl, cyclopentyl and cyclohexyl.

The terms "alkoxy" and "alkyloxy" refer to —O—R groups where R is the above-mentioned alkyl. Additionally, when using the term "R oxy", the term refers to a —O—R group that is a monovalent or divalent group.

The term "(C1-C6) alkoxy" refers to a (C1-C6) alkyl-O— group, and includes, for example, (C1-C3) alkoxy, (C1-C4) alkoxy, (C1-C6) alkoxy, (C2-C6) alkoxy and (C3-C6) alkoxy.

Representative (C1-C6) alkoxys include, for example, methoxy, ethoxy, prop-oxy (e.g., 1-prop-oxy, 2-prop-oxy), butoxy (e.g., 1-butoxy, 2-butoxy, 2-methyl-2-prop-oxy), pent-oxy (1-pent-oxy, 2-pent-oxy) and hex-oxy (1-hex-oxy, 3-hex-oxy).

Similarly, the term "alkylthio" refers to a —S—R group where R is the above-mentioned alkyl. Moreover, when using the term "R thio", it refers to a —S—R group that is a monovalent or divalent group.

The term "heterocyclic group" refers to a monocyclic, bicyclic or polycyclic saturated or unsaturated, non-aromatic or aromatic group (heteroaryl) containing an atom other than carbon (heteroatom), e.g., one or more heteroatoms selected from nitrogen, oxygen, sulfur, SO and $S(=O)_2$ in the ring. Heterocyclic groups include, for example, non-aromatic cyclic amino groups. The heterocyclic groups in the present invention are preferably five- to seven-membered rings and more preferably five- or six-membered rings. Representative heterocyclic groups include, for example, morpholino, oxadinyl, dihydrooxadinyl, piperazinyl, thiomorpholino, piperidino, pyrrodinyl, homomorpholino, pyrrolinyl, pyrrolyl, imidazolyl, pyrazolyl, triazolyl, triazinyl, pyridinyl, pyrimidinyl, pyridazinyl, pyrazinyl, oxazolyl, isoxazolyl, thienyl and furyl.

The term "non-aromatic cyclic amino" refers to monocyclic, bicyclic or polycyclic non-armoatic group containing a nitrogen atom in the ring. Representative non-aromatic cyclic aminos include, for example, morpholino, dihydrooxadinyl, piperazinyl, thiomorpholino, piperidino, pyrrolidinyl and homomorpholino.

The term "three- to five-membered ether" refers to a three-, four- or five-membered saturated or non-aromatic unsaturated carbon ring containing an oxygen atom in the ring, i.e. an ether bond. For example, a representative three-membered cyclic ether group is an oxiranyl group.

The term "aryl" refers to a monocyclic, bicyclic or polycyclic aromatic carbon ring. Representative aryls include phenyl and naphthalenyl etc.

The term "heteroaryl" refers to a monocyclic, bicyclic or polycyclic hetero aromatic ring containing one or more heteroatoms selected from nitrogen, oxygen, sulfur, SO and $S(=O)_2$. Representative heteroaryls include pyridyl, thiazolyl, benzofuranyl, dihydrobenzofuranyl, imidazolyl and pyrazolyl.

The term "saturated or unsaturated" means that the group being referred to is either a saturated group not containing a double bond or triple bond, or an unsaturated group containing at least one double bond or triple bond.

The term "may be substituted" means that the group being referred to is either unsubstituted or substituted with one or more specific substituent groups. For example, while the number of substitution is one, two, three, four or five etc., the number of substitution is preferably one, two or three, more preferably one or two, and even more preferably one. When the group being referred to is substituted with a plurality of substituent groups, the substituent groups may be the same or they may be different.

The term "may comprise a carbonyl group in the carbon chain" means that the group being referred to is either unsubstituted or the carbon chain constituting the group contains carbonyl. For example, the number of carbonyl contained is one or two etc. For example, "alkylene groups which may comprise a carbonyl group" include alkylene group, alkylenecarbonyl group, carbonylalkylene group, alkylenecarbonylalkylene group and carbonylalkylenecarbonyl group.

Some of the above terms may be used several times in a structural formula, and respective terms may have mutually independent ranges.

Some of the above terms may be used in combination, and in such cases, the group that is mentioned first becomes a substituent group on the group that is mentioned later, and the substitution site (adduction site) is on the last portion that is mentioned of the entire group.

[History of the Invention]

The present inventors, as a result of searching for antitumor agents, found a purine derivative with a strong antitumor activity as shown in the embodiments below.

[Embodiments]

Herebelow, modes for carrying out the present invention shall be explained.

An embodiment of the purine derivative of the present invention is a compound represented by formula (I), or a pharmaceutically acceptable salt, solvate or hydrate thereof, or a prodrug thereof:

[Chem. 2]

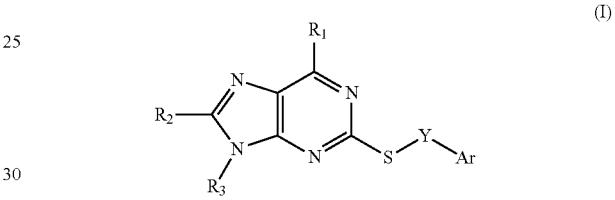

(I)

wherein Ar represents a phenyl group, pyridyl group, thiazolyl group, benzofuranyl group, dihydrobenzofuranyl group, naphthalenyl group, imidazolyl group or pyrazolyl group which may be independently substituted with one, two or three halogens, formyl groups, cyano groups, nitro groups, amino groups, hydroxyl groups or carboxyl groups; or with one, two or three (C1-C6) alkyl groups, (C2-C6) alkenyl groups, (C1-C6) alkylcarbonyl groups, (C1-C6) alkylamino groups, (C1-C6) alkylcarbonylaminocarbonyl groups, (C3-C6) cycloalkylamino groups, (C1-C7) alkoxycarbonylamino groups, di[(C1-C6) alkyl]amino groups, (C1-C6) alkylcarbonylamino groups, (C3-C6) cycloalkylcarbonylamino groups, di[(C1-C6) alkyl]aminocarbonylamino groups, di[(C1-C6) alkyl]aminothiocarbonylamino groups, heteroarylcarbonylamino groups, phenyloxycarbonylamino groups, phenylcarbonylamino groups, (C1-C6) alkylsulfonylamino groups, di[(C1-C6) alkyl]aminosulfonylamino groups, (C1-C6) alkoxy groups, (C1-C6) alkylthio groups, (C1-C6) alkylenedioxy groups, (C1-C6) alkoxycarbonyl groups, amino(C1-C6) alkylcarbonylamino groups, phenyl(C2-C6) alkenylcarbonylamino groups, (C1-C6) alkoxy(C1-C6) alkylcarbonylamino groups, (C1-C6) alkoxycarbonylamino (C1-C6) alkylcarbonylamino groups, phenyl groups or phenyl(C1-C6) alkoxy groups which may be substituted with a halogen, cyano group, amino group, hydroxyl group or carboxyl group;

Y represents a (C1-C6) alkylene group which may comprise a carbonyl group in the carbon chain and/or may be substituted with one or two of Ar;

$R_1$ represents a (C1-C6) alkyl group or (C2-C6) alkenyl group; or an amino group or (C1-C6) alkylcarbonylamino group which may be substituted with one or two (C1-C6) alkyl groups, (C1-C6) alkoxy groups, (C1-C6) alkoxy(C1-C6) alkyl groups, (C3-C6) cycloalkyl groups or (C2-C6) alkenyl groups; or a heterocyclic group which may be substituted with one or two nitroso groups, formyl groups, hydroxyl groups, (C1-C6) alkyl groups, (C1-C6) alkylcarbonyl groups, (C1-C6) alkoxy groups, (C1-C6) alkoxycarbonyl groups or hydroxy (C1-C6) alkylamino groups; or a phenyl group substituted with a halogen, formyl group, cyano group, nitro group, amino group, hydroxyl group, or carboxyl group;

$R_2$ represents H; or a (C1-C6) alkyl group, (C2-C6) alkenyl group, (C2-C6) alkynyl group or (C3-C6) cycloalkyl group which may be substituted with one or two halogens, nitro groups or amino groups; and $R_3$ represents a (C1-C6) alkyl group, (C2-C6) alkenyl group, (C2-C6) alkynyl group, (C3-C6) cycloalkyl group, (C3-C6) cycloalkyl(C1-C6) alkyl group, amino(C1-C6) alkyl group, three- to five-membered ether-(C1-C6) alkyl group or (C1-C6) alkylcarbonylamino(C1-C6) alkyl group which may be substituted with a halogen or hydroxyl group.

Another further embodiment of the present invention is a compound of any one of the above embodiments, or a pharmaceutically acceptable salt, solvate or hydrate thereof, or a prodrug thereof, wherein:

Ar represents a phenyl group, pyridyl group, thiazolyl group, benzofuranyl group, dihydrobenzofuranyl group, naphthalenyl group, imidazolyl group or pyrazolyl group which may be independently substituted with one, two or three halogens, formyl groups, cyano groups, nitro groups, amino groups, hydroxyl groups or carboxyl groups; or with one, two or three (C1-C6) alkyl groups, (C2-C6) alkenyl groups, (C1-C6) alkylcarbonyl groups, (C1-C6) alkylamino groups, (C3-C6) cycloalkylamino groups, (C1-C6) alkoxycarbonylamino groups, di[(C1-C6) alkyl]amino groups, (C1-C6) alkylcarbonylamino groups, (C3-C6) cycloalkylcarbonylamino groups, di[(C1-C6) alkyl]aminocarbonylamino groups, di[(C1-C6) alkyl]aminothiocarbonylamino groups, heteroarylcarbonylamino groups, phenyloxycarbonylamino groups, phenylcarbonylamino groups, (C1-C6) alkylsulfonylamino groups, di[(C1-C6) alkyl]aminosulfonylamino groups, (C1-C6) alkoxy groups, (C1-C6) alkylthio groups, (C1-C6) alkylenedioxy groups, (C1-C6) alkoxycarbonyl groups, amino(C1-C6) alkylcarbonylamino groups, phenyl (C2-C6) alkenylcarbonylamino groups, (C1-C6) alkoxy(C1-C6) alkylcarbonylamino groups, (C1-C6) alkoxycarbonylamino(C1-C6) alkylcarbonylamino groups, phenyl group or phenyl(C1-C6) alkoxy groups which may be substituted with a halogen, cyano group, amino group, hydroxyl group or carboxyl group;

Y represents a (C1-C6) alkylene group which may comprise a carbonyl group in the carbon chain;

$R_1$ represents a (C1-C6) alkyl group or (C2-C6) alkenyl group; or an amino group or (C1-C6) alkylcarbonylamino group which may be substituted with one or two (C1-C6) alkyl groups or (C2-C6) alkenyl groups; or a non-aromatic cyclic amino group which may be substituted with one or two nitroso groups, formyl groups, (C1-C6) alkyl groups, (C1-C6) alkylcarbonyl groups, (C1-C6) alkoxycarbonyl groups or hydroxy (C1-C6) alkylamino groups;

$R_2$ represents H; or a (C1-C6) alkyl group, (C2-C6) alkenyl group, (C2-C6) alkynyl group or (C3-C6) cycloalkyl group which may be substituted with one or two halogens, nitro groups or amino groups; and $R_3$ represents a (C1-C6) alkyl group, (C2-C6) alkenyl group, (C2-C6) alkynyl group, (C3-C6) cycloalkyl group, amino(C1-C6) alkyl group or (C1-C6) alkylcarbonylamino (C1-C6) alkyl group which may be substituted with a halogen or hydroxyl group.

Another preferable embodiment of the present invention is a compound of any of the above embodiments, or a pharmaceutically acceptable salt, solvate or hydrate thereof, or a prodrug thereof, wherein:

Ar is a phenyl group, naphthalenyl group or pyrazolyl group which may be independently substituted with one, two or three halogens, formyl groups, cyano groups, nitro groups, amino groups, hydroxyl groups or carboxyl groups; or with one, two or three (C1-C6) alkyl groups, (C2-C6) alkenyl groups, (C1-C6) alkoxycarbonylamino groups, di[(C1-C6) alkyl]amino groups, (C1-C6) alkylcarbonylamino groups, (C3-C6) cycloalkylcarbonylamino groups, di[(C1-C6) alkyl]aminocarbonylamino groups, heteroarylcarbonylamino groups, phenylcarbonylamino groups, di[(C1-C6) alkyl]aminosulfonylamino groups, (C1-C6) alkoxy groups, amino(C1-C6) alkylcarbonylamino groups, phenyl(C1-C6) alkoxy groups, (C1-C6) alkylthio groups, (C1-C6) alkylenedioxy groups, (C1-C6) alkoxycarbonyl groups or phenyl groups which may be substituted with a halogen.

Here, regarding arbitrary polyvalent groups, in cases of substitution at sites where single rings or multiple rings can be formed, unless particularly limited, the polyvalent groups may form ring structures, and for example, when the above Ar is substituted with a ring structure formed from a (C1-C6) alkylenedioxy group, the following structure may be formed.

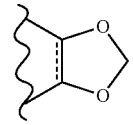

[Chem. 3]

Additionally, a more preferred embodiment of the present invention is a compound of any of the above embodiments, or a pharmaceutically acceptable salt, solvate or hydrate thereof, or a prodrug thereof, wherein Ar is a phenyl group, naphthalenyl group or pyrazolyl group which may be independently substituted with one, two or three halogens, cyano groups, nitro groups, amino groups, hydroxyl groups, (C1-C6) alkyl groups, (C2-C6) alkenyl groups, (C1-C6) alkylcarbonylamino groups, heteroarylcarbonylamino groups, phenylcarbonylamino groups, di[(C1-C6) alkyl]aminosulfonylamino groups, (C1-C6) alkoxy groups, phenyl(C1-C6) alkoxy groups or amino(C1-C6) alkylcarbonylamino groups.

Moreover, a more preferred embodiment of the present invention is a compound of any of the above embodiments, or a pharmaceutically acceptable salt, solvate or hydrate thereof, or a prodrug thereof, wherein Y is a (C1-C6) alkylene group.

Another preferred embodiment of the present invention is a compound of any of the above embodiments, or a pharmaceutically acceptable salt, solvate or hydrate thereof, or a prodrug thereof, wherein $R_1$ is a (C2-C6) alkenyl group; or an amino group or (C1-C6) alkylcarbonylamino group which may be substituted with one or two (C1-C6) alkyl groups, (C1-C6) alkoxy groups or (C3-C6) cycloalkyl groups; or a heterocyclic group which may be substituted with one or two nitroso groups, (C1-C6) alkyl groups, (C1-C6) alkylcarbonyl groups or (C1-C6) alkoxycarbonyl groups.

Further, a more preferred embodiment of the present invention is a compound of any of the above embodiments, or a pharmaceutically acceptable salt, solvate or hydrate thereof, or a prodrug thereof, wherein $R_1$ is an amino group or (C1-C6) alkylcarbonylamino group which may be substituted with one or two (C1-C6) alkyl groups or (C1-C6) alkoxy groups; or a heterocyclic group which may be substituted with one or two nitroso groups, (C1-C6) alkyl groups or (C1-C6) alkylcarbonyl groups.

Moreover, another further embodiment of the present invention is a compound of any of the above embodiments, or a pharmaceutically acceptable salt, solvate or hydrate thereof, or a prodrug thereof, wherein $R_1$ is a (C2-C6) alkenyl group; or an amino group or (C1-C6) alkylcarbonylamino group which may be substituted with one or two (C1-C6) alkyl groups; or a non-aromatic cyclic amino group which may be substituted with one or two nitroso groups, (C1-C6) alkyl groups, (C1-C6) alkylcarbonyl groups or (C1-C6) alkoxycarbonyl groups.

Additionally, another further embodiment of the present invention is a compound of any of the above embodiments, or a pharmaceutically acceptable salt, solvate or hydrate thereof, or a prodrug thereof, wherein $R_1$ is an amino group or (C1-C6) alkylcarbonylamino group which may be substituted with one or two (C1-C6) alkyl groups; or a non-aromatic cyclic amino group which may be substituted with one or two nitroso groups, (C1-C6) alkyl groups or (C1-C6) alkylcarbonyl groups.

Another preferred embodiment of the present invention is a compound of any of the above embodiments, or a pharmaceutically acceptable salt, solvate or hydrate thereof, or a prodrug thereof, wherein the heterocyclic group is a morpholino group, oxadinyl group, dihydrooxadinyl group, piperazinyl group, thiomorpholino group, piperidino group, pyrrodinyl group, homomorpholino group, pyrrolinyl group, pyrrolyl group, imidazolyl group, pyrazolyl group, triazolyl group, triazinyl group, pyridinyl group, pyrimidinyl group, pyridazinyl group, pyrazinyl group, oxazolyl group, isoxazolyl group, thienyl group or furyl group.

In addition, a more preferred embodiment of the present invention is a compound of any of the above embodiments, or a pharmaceutically acceptable salt, solvate or hydrate thereof, or a prodrug thereof, wherein the heterocyclic group is a morpholino group, oxadinyl group, dihydrooxadinyl group, piperazinyl group, pyrrolinyl group, pyrrolyl group, imidazolyl group, pyrazolyl group, triazolyl group, oxazolyl group, isoxazolyl group, thienyl group or furyl group.

Further, an even more preferred embodiment of the present invention is a compound of any of the above embodiments, or a pharmaceutically acceptable salt, solvate or hydrate thereof, or a prodrug thereof, wherein the heterocyclic group is a morpholino group, dihydrooxadinyl group, pyrrolyl group, imidazolyl group, pyrazolyl group, isoxazolyl group or thienyl group.

Moreover, another further embodiment of the present invention is a compound of any of the above embodiments, or a pharmaceutically acceptable salt, solvate or hydrate thereof, or a prodrug thereof, wherein the heterocyclic group or non-aromatic cyclic amino group is a morpholino group or piperazinyl group.

Another preferred embodiment of the present invention is a compound of any of the above embodiments, or a pharmaceutically acceptable salt, solvate or hydrate thereof, or a prodrug thereof, wherein $R_2$ is H, a (C1-C6) alkyl group, (C2-C6) alkenyl group or (C3-C6) cycloalkyl group.

Furthermore, a more preferred embodiment of the present invention is a compound of any of the above embodiments, or a pharmaceutically acceptable salt, solvate or hydrate thereof, or a prodrug thereof, wherein $R_2$ is H, a (C1-C6) alkyl group or (C2-C6) alkenyl group.

Another preferred embodiment of the present invention is a compound of any of the above embodiments, or a pharmaceutically acceptable salt, solvate or hydrate thereof, or a prodrug thereof, wherein $R_3$ is a (C1-C6) alkyl group, (C2-C6) alkenyl group or acetylamino(C1-C6) alkyl group which may be substituted with a halogen or hydroxyl group.

Additionally, a more preferred embodiment of the present invention is a compound of any of the above embodiments, or a pharmaceutically acceptable salt, solvate or hydrate thereof, or a prodrug thereof, wherein $R_3$ is a (C1-C6) alkyl group which may be substituted with a halogen or hydroxyl group.

As examples of the purine derivatives in the above embodiments, the following compounds may be given, but the purine derivatives of the present invention is not limited to these compounds.

TABLE 1

| Compound No. | Compoud Name | Structural Formula |
| --- | --- | --- |
| 1 | 8-ethyl-2-(4-methoxybenzylsulfanyl)-9-methyl-6-morpholino-9H-purine | |
| 2 | 2-(3-amino-4-methoxybenzylsulfanyl)-8-ethyl-9-methyl-6-morpholino-9H-purine | |

TABLE 1-continued

| Compound No. | Compound Name | Structural Formula |
|---|---|---|
| 3 | 2-(4-methoxybenzylsulfanyl)-8,9-dimethyl-6-morpholino-9H-purine | |
| 4 | 2-(4-methoxybenzylsulfanyl)-9-methyl-6-morpholino-8-propyl-9H-purine | |
| 5 | 8-ethyl-2-(4-methoxycarbonylbenzylsulfanyl)-9-methyl-6-morpholino-9H-purine | |
| 6 | 8-ethyl-2-(4-methoxybenzylsulfanyl)-6-morpholino-9-propyl-9H-purine | |
| 7 | 8-ethyl-2-(4-methoxybenzylsulfanyl)-9-methyl-6-(4-nitrosopiperazin-1-yl)-9H-purine | |

TABLE 1-continued

| Compound No. | Compound Name | Structural Formula |
|---|---|---|
| 8 | 8-ethyl-9-methyl-2-(4-methylbenzyl-sulfanyl)-6-morpholino-9H-purine | |
| 9 | 2-(4-methoxybenzylsulfanyl)-9-methyl-6-morpholino-9H-purine | |
| 10 | 8-ethyl-9-methyl-6-morpholino-2-(4-vinylbenzylsulfanyl)-9H-purine | |
| 11 | 8-ethyl-2-(3-fluoro-4-methylbenzyl-sulfanyl)-9-methyl-6-morpholino-9H-purine | |
| 12 | 8-ethyl-2-(4-ethylbenzylsulfanyl)-9-methyl-6-morpholino-9H-purine | |

TABLE 1-continued

| Compound No. | Compound Name | Structural Formula |
|---|---|---|
| 13 | 8-ethyl-2-(3-hydroxy-4-methoxybenzyl-sulfanyl)-9-methyl-6-morpholino-9H-purine | |
| 14 | 8-ethyl-2-(3-fluoro-4-methoxybenzyl-sulfanyl)-9-methyl-6-morpholino-9H-purine | |
| 15 | 2-(2-benzyloxy-4-methoxybenzyl-sulfanyl)-8-ethyl-9-methyl-6-morpholino-9H-purine | |
| 16 | 2-(3-chloro-4-methoxybenzylsulfanyl)-8-ethyl-9-methyl-6-morpholino-9H-purine | |
| 17 | 2-(4-ethoxybenzylsulfanyl)-8-ethyl-9-methyl-6-morpholino-9H-purine | |

TABLE 1-continued

| Compound No. | Compound Name | Structural Formula |
|---|---|---|
| 18 | 2-(3-amino-4-methoxybenzylsulfanyl)-9-methyl-6-morpholino-9H-purine | |
| 19 | 2-(3-amino-4-methoxybenzylsulfanyl)-6-dimethylamino-9-methyl-9H-purine | |
| 20 | 8-ethyl-2-(3-fluoro-4-methoxybenzyl-sulfanyl)-9-methyl-6-(4-nitrosopiperazin-1-yl)-9H-purine | |
| 21 | 6-dimethylamino-2-(4-methoxybenzyl-sulfanyl)-9-methyl-9H-purine | |
| 22 | 8-ethyl-2-(4-methoxybenzylsulfanyl)-9-methyl-6-[(3S)-3-methyl-4-nitrosopiperazin-1-yl]-9H-purine | |

TABLE 1-continued

| Compound No. | Compound Name | Structural Formula |
|---|---|---|
| 23 | 2-(3-amino-4-methoxybenzylsulfanyl)-6-dimethylamino-8-ethyl-9-methyl-9H-purine | |
| 24 | 6-dimethylamino-8-ethyl-2-(4-methoxy-benzylsulfanyl)-9-methyl-9H-purine | |
| 25 | 6-diethylamino-2-(4-methoxybenzyl-sulfanyl)-9-methyl-9H-purine | |
| 26 | 2-(4-methoxybenzylsulfanyl)-9-methyl-6-methylamino-9H-purine | |
| 27 | 2-(3-acetylamino-4-methoxybenzyl-sulfanyl)-8-ethyl-9-methyl-6-morpholino-9H-purine | |
| 28 | 2-[3-(2-aminoacetylamino)-4-methoxy-benzylsulfanyl]-8-ethyl-9-methyl-6-morpholino-9H-purine hydrochloride | |

TABLE 1-continued

| Compound No. | Compound Name | Structural Formula |
|---|---|---|
| 29 | 9-(2-acetylaminoethyl)-8-ethyl-2-(4-methoxybenzylsulfanyl)-6-morpholino-9H-purine | |
| 30 | 8-ethyl-9-(2-fluoroethyl)-2-(4-methoxybenzylsulfanyl)-6-morpholino-9H-purine | |
| 31 | 8-ethyl-2-(4-fluoromethylbenzylsulfanyl)-9-methyl-6-morpholino-9H-purine | |
| 32 | 8-ethyl-9-methyl-2-(4-methylsulfanylbenzylsulfanyl)-6-morpholino-9H-purine | |
| 33 | 8-ethyl-2-(2-fluoro-4-methoxybenzylsulfanyl)-9-methyl-6-morpholino-9H-purine | |

TABLE 1-continued

| Compound No. | Compound Name | Structural Formula |
|---|---|---|
| 34 | 6-(4-acetylpiperazin-1-yl)-8-ethyl-2-(4-methoxybenzylsulfanyl)-9-methyl-9H-purine | |
| 35 | 2-(4-dimethylaminobenzylsulfanyl)-8-ethyl-9-methyl-6-morpholino-9H-purine | |
| 36 | 2-(benzo[1,3]dioxol-5-yl-methyl-sulfanyl)-8-ethyl-9-methyl-6-morpholino-9H-purine | |
| 37 | 8-ethyl-2-(4-methoxy-3-methylbenzyl-sulfanyl)-9-methyl-6-morpholino-9H-purine | |
| 38 | 8-ethyl-2-[1-(4-methoxyphenyl)ethylsulfanyl]-9-methyl-6-morpholino-9H-purine | |

TABLE 1-continued

| Compound No. | Compound Name | Structural Formula |
|---|---|---|
| 39 | 8-ethyl-2-(3-methoxycarbonylamino-4-methoxybenzylsulfanyl)-9-methyl-6-morpholino-9H-purine | |
| 40 | 2-(3-amino-4-methylbenzylsulfanyl)-8-ethyl-9-methyl-6-morpholino-9H-purine | |
| 41 | 2-(5-chloro-3-methyl-1-phenyl-1H-pirazol-4-ylmethylsulfanyl)-8-ethyl-9-methyl-6-morpholino-9H-purine | |
| 42 | 8-ethyl-2-(6-methoxynaphthalen-2-ylmethylsulfanyl)-9-methyl-6-morpholino-9H-purine | |
| 43 | 8-ethyl-2-(4-methoxynaphthalen-1-ylmethylsulfanyl)-9-methyl-6-morpholino-9H-purine | |

TABLE 1-continued

| Compound No. | Compound Name | Structural Formula |
|---|---|---|
| 44 | 8-ethyl-2-[2-(4-methoxyphenyl)ethylsulfanyl]-9-methyl-6-morpholino-9H-purine | |
| 45 | 2-(3-amino-4-methoxybenzylsulfanyl)-9-methyl-6-methylamino-9H-purine | |
| 46 | 2-(4-bromobenzylsulfanyl)-8-ethyl-9-methyl-6-morpholino-9H-purine | |
| 47 | 8-ethyl-2-[2-(4-fluorobenzoyl)ethylsulfanyl]-9-methyl-6-morpholino-9H-purine | |
| 48 | 8-ethyl-2-[2-(4-methylbenzoyl)ethylsulfanyl]-9-methyl-6-morpholino-9H-purine | |

TABLE 1-continued

| Compound No. | Compound Name | Structural Formula |
|---|---|---|
| 49 | 8-ethyl-2-(4-iodobenzylsulfanyl)-9-methyl-6-morpholino-9H-purine | |
| 50 | 8-ethyl-2-[3-(4-methoxyphenyl)propyl-sulfanyl]-9-methyl-6-morpholino-9H-purine | |
| 51 | 2-(3-cyano-4-methoxybenzylsulfanyl)-8-ethyl-9-methyl-6-morpholino-9H-purine | |
| 52 | 8-ethyl-2-(4-methoxy-3-pivaloylamino-benzylsulfanyl)-9-methyl-6-morpholino-9H-purine | |
| 53 | 8-ethyl-2-(4-methoxy-3-propionyl-aminobenzylsulfanyl)-9-methyl-6-morpholino-9H-purine | |

TABLE 1-continued

| Compound No. | Compound Name | Structural Formula |
|---|---|---|
| 54 | 2-(3-cyclopropanecarbonylamino-4-methoxybenzylsulfanyl)-8-ethyl-9-methyl-6-morpholino-9H-purine | |
| 55 | 8-ethyl-2-[3-(2-furylcarbonyl)amino-4-methoxybenzylsulfanyl]-9-methyl-6-morpholino-9H-purine | |
| 56 | 2-(3-dimethylaminocarbonylamino-4-methoxybenzylsulfanyl)-8-ethyl-9-methyl-6-morpholino-9H-purine | |
| 57 | 2-(3-dimethylsulfamoylamino-4-methoxybenzylsulfanyl)-8-ethyl-9-methyl-6-morpholino-9H-purine | |
| 58 | 2-(3-dimethylaminothiocarbonylamino-4-methoxybenzylsulfanyl)-8-ethyl-9-methyl-6-morpholino-9H-purine | |

TABLE 1-continued

| Compound No. | Compound Name |
|---|---|
| 59 | 8-ethyl-2-[3-(4-fluorobenzoylamino)-4-methoxybenzylsulfanyl]-9-methyl-6-morpholino-9H-purine |
| 60 | 2-(3-acetylamino-4-methoxybenzyl-sulfanyl)-6-dimethylamino-8-ethyl-9-methyl-9H-purine |
| 61 | 6-(N-acetyl-N-methylamino)-2-(4-methoxybenzylsulfanyl)-9-methyl-9H-purine |
| 62 | 2-[3-(2-tert-butoxycarbonylaminoacetyl-amino)-4-methoxybenzylsulfanyl]-8-ethyl-9-methyl-6-morpholino-9H-purine |
| 63 | 8-ethyl-2-(3-methoxyacetylamino-4-methoxybenzylsulfanyl)-9-methyl-6-morpholino-9H-purine |

TABLE 1-continued

| Compound No. | Compoud Name | Structural Formula |
|---|---|---|
| 64 | 6-ethylamino-2-(4-methoxybenzyl-sulfanyl)-9-methyl-9H-purine | |
| 65 | 8-ethyl-6-(N-ethyl-N-methylamino)-2-(4-methoxybenzylsulfanyl)-9-methyl-9H-purine | |
| 66 | [2-(3-trans-cinnamoylamino)-4-methoxybenzylsulfanyl]-8-ethyl-9-methyl-6-morpholino-9H-purine | |
| 67 | 2-(3-dimethylamino-4-methoxybenzyl-sulfanyl)-8-ethyl-9-methyl-6-morpholino-9H-purine | |
| 68 | 8-ethyl-6-(N-ethyl-N-methylamino)-2-(4-iodobenzylsulfanyl)-9-methyl-9H-purine | |
| 69 | 2-(3-cyano-4-methoxybenzylsulfanyl)-6-dimethylamino-8-ethyl-9-methyl-9H-purine | |

TABLE 1-continued

| Compound No. | Compound Name | Structural Formula |
|---|---|---|
| 70 | 2-[3-(iso-butoxycarbonylamino)-4-methoxybenzylsulfanyl]-8-ethyl-9-methyl-6-morpholino-9H-purine | |
| 71 | 6-dimethylamino-8-ethyl-2-(3-fluoro-4-methoxybenzylsulfanyl)-9-methyl-9H-purine | |
| 72 | 2-(3-cyano-4-methoxybenzylsulfanyl)-6-methylamino-9-methyl-9H-purine | |
| 73 | 2-(3-fluoro-4-methoxybenzylsulfanyl)-6-methylamino-9-methyl-9H-purine | |
| 74 | 6-diethylamino-8-ethyl-2-(4-methoxybenzylsulfanyl)-9-methyl-9H-purine | |
| 75 | 6-(N-ethyl-N-methylamino)-2-(4-methoxybenzylsulfanyl)-9-methyl-9H-purine | |

TABLE 1-continued

| Compound No. | Compound Name | Structural Formula |
|---|---|---|
| 76 | 6-acetylamino-2-(4-methoxybenzyl-sulfanyl)-9-methyl-9H-purine | |
| 77 | 8-ethyl-2-(3-heptoxycarbonylamino-4-methoxybenzylsulfanyl)-9-methyl-6-morpholino-9H-purine | |
| 78 | 2-(3-bromo-4-methoxybenzyl-sulfanyl)-8-ethyl-9-methyl-6-morpholino-9H-purine | |
| 79 | 8-ethyl-2-(4-methoxy-3-vinylbenzyl-sulfanyl)-9-methyl-6-morpholino-9H-purine | |
| 80 | 2-(3-cyano-4-methoxybenzylsulfanyl)-9-methyl-6-morpholino-9H-purine | |

TABLE 1-continued

| Compound No. | Compoud Name | Structural Formula |
|---|---|---|
| 81 | 8-ethyl-2-[3-(N-acetylcarbamoyl)-4-methoxybenzylsulfanyl]-9-methyl-6-morpholino-9H-purine | |
| 82 | 6-(N-ethyl-N-methylamino)-2-(3-fluoro-4-methoxybenzylsulfanyl)-9-methyl-9H-purine | |
| 83 | 2-(3-fluoro-4-methoxybenzylsulfanyl)-9-methyl-6-morpholino-9H-purine | |
| 84 | 2-(3-amino-4-methoxybenzylsulfanyl)-6-(N-ethyl-N-methylamino)-9-methyl-9H-purine | |
| 85 | 2-(3-cyano-4-methoxybenzylsulfanyl)-6-(N-ethyl-N-methylamino)-9-methyl-9H-purine | |
| 86 | 6-dimethylamino-2-(3-fluoro-4-methoxybenzylsulfanyl)-9-methyl-9H-purine | |

TABLE 1-continued

| Compound No. | Compound Name | Structural Formula |
|---|---|---|
| 87 | 2-(3-cyano-4-methoxybenzyl-sulfanyl)-6-dimethylamino-9-methyl-9H-purine | |
| 88 | 6-(2-ethoxymorpholino)-2-(4-methoxybenzylsulfanyl)-9-methyl-9H-purine | |
| 89 | 2-(3-cyano-4-methoxybenzylsulfanyl)-6-ethylamino-9-methyl-9H-purine | |
| 90 | 2-(3-amino-4-ethylbenzylsulfanyl)-8-ethyl-9-methyl-6-morpholino-9H-purine | |
| 91 | 6-ethylamino-2-(3-fluoro-4-methoxy-benzylsulfanyl)-9-methyl-9H-purine | |
| 92 | 2-(3-amino-4-methoxybenzyl-sulfanyl)-6-ethylamino-9-methyl-9H-purine | |

TABLE 1-continued

| Compound No. | Compound Name | Structural Formula |
|---|---|---|
| 93 | 9-(2-cyclopropylmethyl)-2-(4-methoxybenzylsulfanyl)-6-morpholino-9H-purine | |
| 94 | 2-(3-cyano-4-methoxybenzylsulfanyl)-8,9-diethyl-6-morpholino-9H-purine | |
| 95 | 2-(4-methoxybenzylsulfanyl)-6-morpholino-9-oxiranylmethyl-9H-purine | |
| 96 | 9-allyl-2-(4-methoxybenzylsulfanyl)-6-morpholino-9H-purine | |
| 97 | 2-(3-amino-4-methoxybenzyl-sulfanyl)-8,9-diethyl-6-morpholino-9H-purine | |

TABLE 1-continued

| Compound No. | Compound Name | Structural Formula |
|---|---|---|
| 98 | 2-(4-methoxybenzylsulfanyl)-6-morpholino-9-propargyl-9H-purine | |
| 99 | 2-(4-ethoxybenzylsulfanyl)-9-methyl-6-morpholino-9H-purine | |
| 100 | 2-benzhydrylsulfanyl-8-ethyl-9-methyl-6-morpholino-9H-purine | |
| 101 | 6-cyclopropylamino-2-(4-methoxybenzylsulfanyl)-9-methyl-9H-purine | |
| 102 | 9-ethyl-2-(4-methoxybenzylsulfanyl)-8-methyl-6-morpholino-9H-purine | |

TABLE 1-continued

| Compound No. | Compound Name | Structural Formula |
|---|---|---|
| 103 | 2-(3-amino-4-ethoxybenzylsulfanyl)-8-ethyl-9-methyl-6-morpholino-9H-purine | |
| 104 | 2-(4-methoxybenzylsulfanyl)-9-ethyl-6-morpholino-8-propyl-9H-purine | |
| 105 | 6-(N-methoxy-N-methylamino)-2-(4-methoxybenzylsulfanyl)-9-methyl-9H-purine | |
| 106 | 2-(3-amino-4-ethoxybenzylsulfanyl)-8,9-diethyl-6-morpholino-9H-purine | |
| 107 | 2-(3-amino-4-ethoxybenzylsulfanyl)-9-methyl-6-methylamino-9H-purine | |

TABLE 1-continued

| Compound No. | Compound Name | Structural Formula |
|---|---|---|
| 108 | 2-(4-methoxybenzylsulfanyl)-6-[(2-methoxyethyl)-methylamino]-9-methyl-9H-purine | |
| 109 | 9-methyl-2-(4-methoxybenzyl-sulfanyl)-6-(1-pyrrolyl)-9H-purine | |
| 110 | 6-(imidazol-1-yl)-2-(4-methoxybenzyl-sulfanyl)-9-methyl-9H-purine | |
| 111 | 6-(2-ethoxymorpholino)-8-ethyl-2-(4-methoxybenzylsulfanyl)-9-methyl-9H-purine | |
| 112 | 3-[2-(4-methoxybenzylsulfanyl)-9-methyl-9H-purin-6-yl]-1-methyl-imidazolinium iodide | |

TABLE 1-continued

| Compound No. | Compoud Name | Structural Formula |
|---|---|---|
| 113 | 2-(3-amino-4-propoxybenzylsulfanyl)-8-ethyl-9-methyl-6-morpholino-9H-purine | |
| 114 | 2-(3-amino-4-ethoxybenzylsulfanyl)-9-methyl-6-morpholino-9H-purine | |
| 115 | 8,9-diethyl-2-(3-iodo-4-methoxy-benzylsulfanyl)-6-morpholino-9H-purine | |
| 116 | 2-(4-ethoxy-3-fluorobenzylsulfanyl)-8-ethyl-9-methyl-6-morpholino-9H-purine | |
| 117 | 8,9-diethyl-2-(4-ethoxy-3-fluorobenzylsulfanyl)-6-morpholino-9H-purine | |

TABLE 1-continued

| Compound No. | Compound Name | Structural Formula |
|---|---|---|
| 118 | 6-(2-ethoxymorpholino)-2-(4-methoxy-3-nitrobenzylsulfanyl)-9-methyl-9H-purine | |
| 119 | 2-(3-amino-4-methoxybenzylsulfanyl)-6-(2-ethoxymorpholino)-9-ethyl-9H-purine | |
| 120 | 2-(3-amino-4-methoxybenzylsulfanyl)-6-(2-ethoxymorpholino)-9-methyl-9H-purine | |
| 121 | 2-(4-methoxybenzylsulfanyl)-9-methyl-6-(pyrazol-1-yl)-9H-purine | |
| 122 | 2-(3-amino-4-ethoxybenzylsulfanyl)-9-ethyl-8-methyl-6-morpholino-9H-purine | |

TABLE 1-continued

| Compound No. | Compound Name | Structural Formula |
|---|---|---|
| 123 | 8,9-diethyl-2-(3-fluoro-4-methoxybenzylsulfanyl)-6-morpholino-9H-purine | |
| 124 | 2-(4-methoxybenzylsulfanyl)-9-methyl-6-(1,2,4-triazol-1-yl)-9H-purine | |
| 125 | 2-(3-amino-4-methoxybenzyl-sulfanyl)-9-ethyl-6-methylamino-9H-purine | |
| 126 | 6-allylamino-2-(4-methoxybenzyl-sulfanyl)-9-methyl-9H-purine | |
| 127 | 6-(N,N,-diallylamino)-2-(4-methoxybenzyl-sulfanyl)-9-methyl-9H-purine | |

TABLE 1-continued

| Compound No. | Compoud Name | Structural Formula |
|---|---|---|
| 128 | 2-(4-methoxybenzylsulfanyl)-9-methyl-6-(3-methylpyrrol-1-yl)-9H-purine | |
| 129 | 6-(2-methoxymorpholino)-2-(4-methoxy-3-nitrobenzylsulfanyl)-9-methyl-9H-purine | |
| 130 | 2-(4-methoxybenzylsulfanyl)-9-methyl-6-(3-pyrrolin-1-yl)-9H-purine | |
| 131 | 6-(2-hydroxymorpholino)-2-(4-methoxy-3-nitrobenzylsulfanyl)-9-methyl-9H-purine | |
| 132 | 2-(4-methoxybenzylsulfanyl)-9-methyl-6-morpholino-8-(1-propenyl)-9H-purine | |

TABLE 1-continued

| Compound No. | Compound Name | Structural Formula |
| --- | --- | --- |
| 133 | 6-(2-ethoxymorpholino)-2-(3-fluoro-4-methoxybenzylsulfanyl)-9-methyl-9H-purine | |
| 134 | 2-(3-cyano-4-methoxybenzylsulfanyl)-6-(2-ethoxymorpholino)-9-methyl-9H-purine | |
| 135 | 6-(2-ethoxymorpholino)-9-ethyl-2-(3-fluoro-4-methoxybenzylsulfanyl)-9H-purine | |
| 136 | 2-(3-amino-4-methoxybenzylsulfanyl)-6-dimethylamino-9-ethyl-9H-purine | |
| 137 | 2-(3-fluoro-4-methoxybenzylsulfanyl)-6-(N-methoxy-N-methylamino)-9-methyl-9H-purine | |

TABLE 1-continued

| Compound No. | Compound Name | Structural Formula |
|---|---|---|
| 138 | 6-(2-ethoxymorpholino)-2-(4-ethoxy-3-nitrobenzylsulfanyl)-9-ethyl-9H-purine | |
| 139 | 2-(4-methoxy-3-nitrobenzylsulfanyl)-9-methyl-6-(1-pyrrolyl)-9H-purine | |
| 140 | 2-(3-amino-4-ethoxybenzylsulfanyl)-6-dimethylamino-9-methyl-9H-purine | |
| 141 | 2-(3-amino-4-methoxybenzyl-sulfanyl)-9-methyl-6-(1-pyrrolyl)-9H-purine | |
| 142 | 2-(4-methoxy-3-nitrobenzylsulfanyl)-9-methyl-6-(3-pyrrolin-1-yl)-9H-purine | |

TABLE 1-continued

| Compound No. | Compound Name | Structural Formula |
|---|---|---|
| 143 | 6-(N-methoxy-N-methylamino)-2-(4-methoxy-3-nitrobenzylsulfanyl)-9-methyl-9H-purine | |
| 144 | 2-(3-amino-4-methoxybenzyl-sulfanyl)-9-methyl-6-(3-pyrrolin-1-yl)-9H-purine | |
| 145 | 2-(3-amino-4-methoxybenzyl-sulfanyl)-6-(N-methoxy-N-methylamino)-9-methyl-9H-purine | |
| 146 | 2-[2-(6-methoxynaphthalen-2-yl)-2-oxoethylsulfanyl]-8-ethyl-9-methyl-6-morpholino-9H-purine | |
| 147 | 6-(2,3-dihydro-[1,4]oxazin-4-yl)-2-(4-methoxybenzylsulfanyl)-9-methyl-9H-purine | |

TABLE 1-continued

| Compound No. | Compoud Name | Structural Formula |
|---|---|---|
| 148 | 6-(2,3-dihydro-[1,4]oxazin-4-yl)-8-ethyl-2-(4-methoxybenzyl-sulfanyl)-9-methyl-9H-purine | |
| 149 | 6-(2,3-dihydro-[1,4]oxazin-4-yl)-2-(4-methoxy-3-nitrobenzyl-sulfanyl)-9-methyl-9H-purine | |
| 150 | 2-(3-amino-4-methoxybenzyl-sulfanyl)-6-(2,3-dihydro-[1,4]oxazin-4-yl)-9-methyl-9H-purine | |
| 151 | 2-(3-amino-4-methoxybenzyl-sulfanyl)-6-(2,3-dihydro-[1,4]oxazin-4-yl)-9-ethyl-9H-purine | |
| 152 | 6-(2,3-dihydro-[1,4]oxazin-4-yl)-2-(3-fluoro-4-methoxybenzylsulfanyl)-9-methyl-9H-purine | |

TABLE 1-continued

| Compound No. | Compound Name | Structural Formula |
|---|---|---|
| 153 | 2-(3-cyano-4-methoxybenzyl-sulfanyl)-6-(2,3-dihydro-[1,4]oxazin-4-yl)-9-methyl-9H-purine | |
| 154 | 6-(2,3-dihydro-[1,4]oxazin-4-yl)-9-ethyl-2-(3-fluoro-4-methoxybenzyl-sulfanyl)-9H-purine | |
| 155 | 6-(2,3-dihydro-[1,4]oxazin-4-yl)-9-ethyl-2-(3-nitro-4-ethoxybenzyl-sulfanyl)-9H-purine | |
| 156 | 2-(3-amino-4-ethoxybenzylsulfanyl)-6-(2,3-dihydro-[1,4]oxazin-4-yl)-9-ethyl-9H-purine | |
| 157 | 6-(2,3-dihydro[1,4]oxazin-4-yl)-8-ethyl-2-(3-fluoro-4-methoxybenzyl-sulfanyl)-9-methyl-9H-purine | |

TABLE 1-continued

| Compound No. | Compound Name | Structural Formula |
|---|---|---|
| 158 | 8,9-diethyl-6-(2,3-dihydro-[1,4]oxazin-4-yl)-2-(4-methoxybenzyl-sulfanyl)-9H-purine | 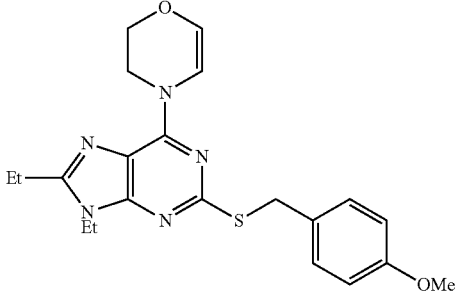 |
| 159 | 6-(2,3-dihydro-[1,4]oxazin-4-yl)-2-(4-ethoxy-3-nitrobenzylsulfanyl)-9-methyl-9H-purine | 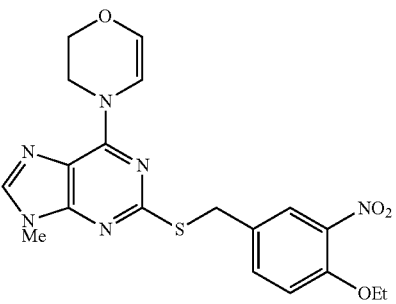 [SMILES: CCOc1ccc(CSc2nc(N3C=COCC3)c3ncn(C)c3n2)cc1[N+](=O)[O-]] |
| 160 | 2-(3-amino-4-ethoxybenzylsulfanyl)-6-(2,3-dihydro-[1,4]oxazin-4-yl)-9-methyl-9H-purine | 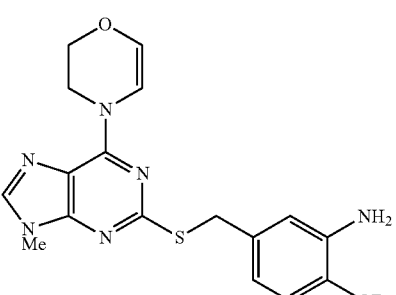 |
| 161 | 2-(3-cyano-4-methoxybenzyl-sulfanyl)-6-(2,3-dihydro-[1,4]oxazin-4-yl)-8-ethyl-9-methyl-9H-purine | 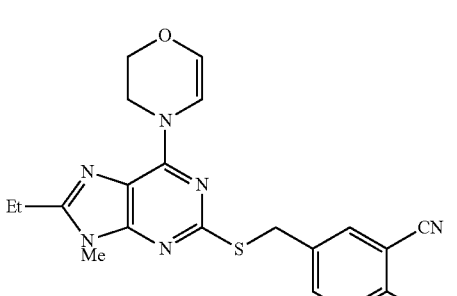 |
| 162 | 2-(3-amino-4-methoxybenzyl-sulfanyl)-6-(2,3-dihydro-[1,4]oxazin-4-yl)-8-ethyl-9-methyl-9H-purine | 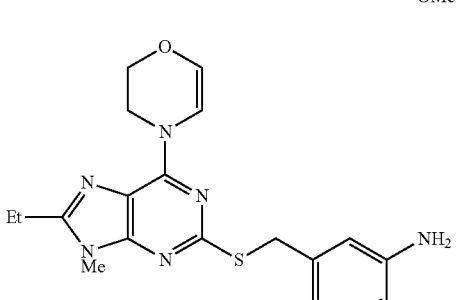 |

TABLE 1-continued

| Compound No. | Compound Name |
|---|---|
| 163 | 2-(4-methoxybenzylsulfanyl)-9-methyl-6-(1-trans-propenyl)-9H-purine |
| 164 | 2-(4-methoxybenzylsulfanyl)-9-methyl-6-propyl-9H-purine |
| 165 | 2-(4-methoxybenzylsulfanyl)-9-methyl-6-vinyl-9H-purine |
| 166 | 2-(4-methoxybenzylsulfanyl)-9-methyl-6-(4-nitrophenyl)-9H-purine |
| 167 | 6-(2-furyl)-2-(4-methoxybenzylsulfanyl)-9-methyl-9H-purine |

TABLE 1-continued

| Compound No. | Compound Name | Structural Formula |
|---|---|---|
| 168 | 2-(4-methoxybenzylsulfanyl)-9-methyl-6-(3-thienyl)-9H-purine | |
| 169 | 6-(3,5-dimethylisoxazol-4-yl)-2-(4-methoxybenzylsulfanyl)-9-methyl-9H-purine | |
| 170 | 2-(4-methoxybenzylsulfanyl)-9-methyl-6-(pyrazol-4-yl)-9H-purine | |
| 171 | 2-(4-methoxy-3-nitrobenzylsulfanyl)-9-methyl-6-(1-trans-propenyl)-9H-purine | |
| 172 | 2-(4-methoxybenzylsulfanyl)-9-methyl-6-(1-methylpyrazol-4-yl)-9H-purine | |

TABLE 1-continued

| Compound No. | Compoud Name | Structural Formula |
|---|---|---|
| 173 | 2-(3-amino-4-methoxybenzyl-sulfanyl)-9-methyl-6-(1-trans-propenyl)-9H-purine | |
| 174 | 2-(4-methoxybenzylsulfanyl)-9-methyl-6-(2-thienyl)-9H-purine | |

The above purine derivatives, when having an asymmetric carbon atom in their structures, include all isomers derived from the asymmetric carbon atom and mixtures thereof (racemic mixtures).

Methods for preparing, separating and isolating desired stereoisomers from racemic mixtures or non-racemic mixtures are well known to those skilled in the art, and for example, preparation of a diastereoisomer salt or complex that can be separated by crystallization; for example, preparation of a diastereoisomer that can be separated by crystallization or gas-liquid or liquid chromatography; selective reaction of one optical isomer using an optical isomer-specific reagent, e.g., enzymatic oxidation or reduction, followed by separation of the optical isomer; or separation by gas-liquid or liquid chromatography etc. in a chiral environment (e.g. in the presence of a chiral support such as bound chiral ligand bound silica or a chiral solvent) is possible.

Further, the above purine derivatives may, for example, be in a form dissolved in a pharmaceutically acceptable solvent such as water or ethanol. In general, a dissolved form can be considered to be equivalent to an undissolved form with regard to the objects of the present invention.

Furthermore, the above purine derivatives may be in the form of hydrates, solvates or pharmaceutically acceptable salts (acid addition salts or base addition salts) etc. A "pharmaceutically acceptable salt" refers to a salt that can be accepted pharmaceutically and can provide the desired pharmacological activity of the parent compound. A pharmaceutically acceptable salt is understood as being non-toxic or as being within a range of toxicity that is applicable to the human body. Further information relating to suitable pharmaceutically acceptable salts is known in the relevant technical field, as described in *Remington's Pharmaceutical Sciences*, 17$^{th}$ ed., Mack Publishing Company, Easton, Pa., 1985 and S. M. Berge et al., "Pharmaceutical Salts", *J. Pharm. Sci.*, 1977; 66:1-19 incorporated herein by reference.

Examples of pharmaceutically acceptable acid addition salts include salts formed by the addition of, for example, inorganic acids such as hydrochloric acid, hydrobromic acid, sulfuric acid, nitric acid, and phosphoric acid; or organic acids such as acetic acid, trifluoroacetic acid, propionic acid, hexanoic acid, cyclopentane propionic acid, glycolic acid, pyruvic acid, lactic acid, oxalic acid, maleic acid, malonic acid, succinic acid, fumaric acid, malic acid, tartaric acid, citric acid, benzoic acid, cinnamic acid, 3-(4-hydroxybenzoyl)benzoic acid, mandelic acid, methane sulfonic acid, ethane sulfonic acid, 1,2-ethane disulfonic acid, 2-hydroxy ethane sulfonic acid, benzene sulfonic acid, 4-chlorobenzene sulfonic acid, 2-naphthalene sulfonic acid, 4-toluene sulfonic acid, camphor sulfonic acid, glucoheptonic acid, 4,4'-methylene bis-(3-hydroxy-2-ene-1-carboxylic acid), 3-phenyl propionic acid, trimethyl acetic acid, tert-butyl acetic acid, lauryl sulfuric acid, gluconic acid, glutamic acid, hydroxy naphthoic acid, stearic acid, muconic acid, and salicylic acid.

Examples of pharmaceutically acceptable base addition salts include, for example, salts wherein the acidic proton in the parent compound is replaced by a metallic ion, such as salts of sodium, potassium, lithium, ammonium, calcium, magnesium, iron, zinc, copper, manganese, and aluminum. Further, for example, salts derived from organic bases such as primary, secondary and tertiary amines, substituted amines and cyclic amines are also included. Examples of organic bases include isopropylamine, trimethylamine, diethylamine, triethylamine, tripropylamine, ethanolamine, 2-dimethylamino ethanol, dicyclohexylamine, lysine, arginine, histidine, caffeine, procaine, hydrabamine, choline, betaine, ethylenediamine, glucosamine, methyl glucamine, theobromine, purine, piperazine, piperidine, N-ethylpiperidine, tromethamine, N-methyl glucamine, and polyamine resin. Representative organic bases include, for example, isopropylamine, diethylamine, ethanolamine, trimethylamine, dicyclohexylamine, choline and caffeine.

Examples of solvates include, for example, organic solvates such as dimethylsulfoxide solvates, dimethylformamide solvates, and alcohol solvates such as ethanol solvates, methanol solvates and n-propyl alcohol solvates.

Additionally, the above purine derivatives or pharmaceutically acceptable salts, solvates or hydrates thereof may also take the form of prodrugs. Prodrugs refer to compounds that are transformed in vivo, for example, by hydrolysis in the bloodstream, to produce parent compounds. General examples, while not limited to the following, include ester and amide forms of compounds having a carboxyl group, and similarly, amide forms of compounds having an amino group. Examples of pharmaceutically acceptable esters, while not limited to the following, include alkyl esters (e.g. having one to six carbons) in which the alkyl group is linear or branched. Acceptable esters include, for example, cycloalkyl esters and aryl alkyl esters such as benzyl. Examples of pharmaceutically acceptable amides, while not limited to the following, include primary amides as well as secondary and tertiary alkyl amides (e.g, having one to six carbon atoms). These amides and esters may be prepared in accordance with well-known methods in the relevant technical field.

Moreover, other prodrugs may also be prepared by well-known methods in the relevant technical field. In general, according to these methods, appropriate functional groups of compounds are modified. These modified functional groups re-form the original functional groups by a predetermined manipulation or in vivo transformation. Details regarding prodrugs are well known in the relevant technical field as described in T. Higuchi and V. Stella, "Pro-drugs as Novel Delivery Systems", Vol. 14 of the A. C. S. Symposium Series, and *Bioreversible Carriers in Drug Design*, ed. Edward B. Roche, American Pharmaceutical Association and Pergamon Press, 1987, incorporated herein by reference.

Embodiments of the above purine derivatives, or pharmaceutically acceptable salts, solvates or hydrates thereof also include N-oxide derivatives and protected derivatives of the above purine derivatives. For example, in cases where the above purine derivatives include a nitrogen atom that can be oxidized, the nitrogen atom can be transformed to an N-oxide by a well-known method in the relevant technical field. When the above purine derivatives comprise, for example, a hydroxy-, carboxy- or nitrogen-containing group, the group can be protected by an appropriate protecting group. Representatives of appropriate protecting groups are described in T. W. Greene, *Protective Groups in Organic Synthesis*, John Wiley & Sons, Inc. 1991, disclosures thereof being incorporated herein by reference. The protected derivatives of the above purine derivatives may also be prepared by well-known methods in the relevant technical field.

As long as there is no particular limitation and no conflict arises, the term "purine derivative etc." in the present specification shall be used as a collective term that includes all of the various forms described above that the purine derivative may take.

Other embodiments of the present invention are compositions, pharmaceutical compositions, formulations, medicaments or agents comprising the above purine derivative etc. The above compositions, pharmaceutical compositions, formulations, medicaments or agents may comprise a pharmaceutically acceptable adjuvant, diluent and/or carrier in addition to the purine derivative etc. Further, the above compositions, pharmaceutical compositions, formulations, medicaments or agents may further comprise another drug or agent. When the above compositions, pharmaceutical compositions, formulations, medicaments or agents are administered, it is preferred that they comprise a therapeutically effective amount of the purine derivative etc.

Consequently, one embodiment of the above compositions, pharmaceutical compositions, formulations, medicaments or agents is a composition comprising any of the above purine derivatives, or a pharmaceutically acceptable salt, solvate or hydrate thereof, or a prodrug thereof, and a pharmaceutically acceptable adjuvant, diluent or carrier.

Moreover, another embodiment of the above compositions, pharmaceutical compositions, formulations, medicaments or agents is a pharmaceutical composition for treating tumor, comprising any of the above purine derivatives, or a pharmaceutically acceptable salt, solvate or hydrate thereof, or a prodrug thereof.

In addition, another embodiment of the above compositions, pharmaceutical compositions, formulations, medicaments or agents is an antitumor agent comprising any of the above purine derivatives, or a pharmaceutically acceptable salt, solvate or hydrate thereof, or a prodrug thereof.

The above compositions, pharmaceutical compositions, formulations, medicaments or agents may be administered orally or parenterally, and as examples of forms of oral administration, pills, fine grain agents, coated pills, powder medicines, granulated agents, capsules (e.g., hard gelatin capsules, soft gelatin capsules), microcapsules, syrups and the like may be used. Additionally, as examples of forms of parenteral administration, injectable agents (including lyophilized agents for injection that are dissolved at the time of use) and suppositories may be used. Additionally, they may be prepared as liposomal agents. Further, they may be used as liquid agents wherein the purine derivative etc. are pre-dispersed in a pharmaceutically acceptable solvent, and in this case, for example, they can be used as syrups for oral administration or as injectable agents for parenteral administration (including lyophilized agents for injection that are dissolved at the time of use).

Further, the above compositions, pharmaceutical compositions, formulations, medicaments or agents may be administered as, for example, solutions, suspensions, emulsions, microemulsions, multiphase emulsions, foams, topical medicines, pastes, plasters, ointments, coated pills, rinses, rectal capsules, drops, gels, sprays, powders, aerosols, inhalants, eye drops, ophthalmic ointments, ophthalmic rinses, vaginal pessaries, vaginal rings, vaginal ointments, infusion solutions or grafts.

The above compositions, pharmaceutical compositions, formulations, medicaments or agents may be prepared using an adjuvant, diluent and/or carrier (excipient). As the adjuvant, for example, a colorant, sweetening agent, flavoring agent, binding agent, wetting agent, adsorbent, lubricant, disintegrant, softening agent, suspending agent, emulsifying agent, preservative, antioxidant, surfactant, stabilizing agent, pH adjusting agent, dispersing agent, isotonic agent and/or absorption promoter may be used; and as the diluent, for example, distilled water or a physiological saline solution may be used. These various forms of administration may be prepared according to conventional methods, and may be prepared aseptically.

Furthermore, a functional coating such as an enteric coating may be further applied to the above forms of administration depending on the conditions of use. In cases of administration in a solid form, for example, preparation can be done using a coating such as an enteric coating or shell. Additionally, such forms of administration can be made to release compounds at a certain portion of the intestinal tract in a delayed manner. Representative examples of appropriate embedding compositions are, for example, polymer substances and waxes. Additionally, they may be put in the form of microcapsules along with an excipient.

Examples of the above excipient (carrier) include crystalline cellulose, sugars (e.g., glucose, sucrose, lactose, D-mannitol, D-sorbitol), starches (e.g., corn starch, potato starch, wheat starch, rice starch), magnesium silicate, sodium hydrogen phosphate, calcium hydrogen phosphate, sodium citrate and talc.

Examples of the above disintegrant include sodium carbonate, calcium carbonate, gum arabic, starches (e.g., corn starch, potato starch, wheat starch, tapioca starch, rice starch), agar, alginic acid, silicate complex, tragacanth, crystalline cellulose, low substituted hydroxypropyl cellulose, croscarmellose sodium, carmellose calcium, carmellose sodium and sodium carboxymethyl starch.

Examples of the above binding agent include cellulose derivatives, starches, alginates, gelatin, polyvinyl pyrrolidone, sucrose and acacia gum.

Examples of the above wetting agents include glycerol, cetyl alcohol and glycerol monostearate, magnesium stearate, talc, calcium stearate, solid polyethylene glycol and sodium lauryl sulfate.

Examples of the above absorption promoter include quaternary ammonium compounds.

Examples of the above adsorbent include kaolin and bentonite.

Examples of the above lubricant include carnauba wax, hydrogenated oil, magnesium stearate, calcium stearate, sodium hydrogen phosphate, calcium hydrogen phosphate and white beeswax.

Examples of the above preservative include paraben, chlorobutanol, phenol, and sorbic acid.

Examples of the above isotonic agent include sugars and sodium chloride.

Examples of the above suspending agent include ethoxylated isostearyl alcohols, polyoxyethylene sorbitol and sorbitan ester, microcrystalline cellulose, aluminum metahydroxide, bentonite, agar, and tragacanth.

Moreover, as agents that delay the absorption of injectable agents, for example, aluminum monostearate and gelatin etc. may also be used.

The above examples of adjuvants etc. are merely illustrative, and various adjuvants that are well-known in the relevant technical field may be used, as long as they provide the desired effect.

Liquid dosage forms for oral administration of the above compositions, pharmaceutical compositions, formulations, medicaments or agents include pharmaceutically acceptable emulsions, solutions, suspensions, syrups and elixirs. Such dosage forms are generally prepared, for example, by dissolving or dispersing the above purine derivative etc. in a carrier, for example, distilled water, physiological saline solution, aqueous dextrose, glycerol or ethanol; for example, a dissolving agent or emulsifying agent such as ethyl alcohol, isopropyl alcohol, ethyl carbonate, ethyl acetate, benzyl alcohol, benzyl benzoate, propylene glycol, 1,3-butylene glycol or dimethylformamide; for example, an oil such as cotton seed oil, peanut oil, corn germ oil, olive oil, castor oil or sesame oil, or a fatty acid ester oil of glycerol, tetrahydrofurfuryl alcohol, polyethylene glycol or sorbitan; or a mixture of these substances, and forming solutions or suspensions.

Dosage forms suitable for injection of the above compositions, pharmaceutical compositions, formulations, medicaments or agents may be prepared by using a physiologically acceptable aqueous or non-aqueous sterile solution, dispersion, suspension or emulsion, or a sterile powder reconstituted in a sterilized solution and/or dispersion for injection. Representative examples of appropriate aqueous or non-aqueous carriers, diluents, solvents or vehicles are distilled water, ethanol, polyols (such as propylene glycol, polyethylene glycol and glycerol), appropriate mixtures thereof, plant-derived oils (e.g. olive oil) and injectable organic esters such as ethyl oleate.

Dosage forms suitable for rectal administration of the above compositions, pharmaceutical compositions, formulations, medicaments or agents may be prepared as suppositories using, for example, an appropriate carrier (excipient). The excipient is preferably a non-irritating excipient, and examples include cocoa butter, polyethylene glycol and suppository waxes which are in a solid state at normal temperatures, but are in a liquid state at body temperature and dissolve in appropriate body cavities to release the active ingredient there.

Dosage forms for local application of the compounds of the present invention include ointments, powders, sprays and inhalants. The active ingredient is mixed under sterile conditions with a pharmaceutically acceptable carrier and, if necessary, an optional preservative, buffer or spraying agent. Ophthalmic preparations, ophthalmic ointments, powders and solutions are considered to be within the scope of the present invention.

Methods for preparing the above dosage forms are well known in the relevant technical field, and are described in, for example, *Remington's Pharmaceutical Sciences*, 18$^{th}$ Ed., (Mack Publishing Company, Easton, Pa., 1990), incorporated herein by reference.

When applying the above purine derivative etc. to a mammal, especially a human, delivery can be made using any form of administration suitable for the desired delivery route, oral or parenterel (e.g., routes including transdermal, intradermal, intrabronchial, intranasal, intra-arterial, intravenous, intramuscular, subcutaneous, intraluminal, transvaginal, transrectal, sublingual, intracranial, epidural, intratracheal, intraocular, and other local sites).

Including cases of prophylactic use, one example of a preferable route of administration is oral administration which allows dosage to be adjusted in accordance with the severity of the targeted disease state, and increases the quality of life of the user.

The above purine derivative etc. is effective in the treatment of various tumors (including benign tumors and malignant tumors (cancer), as well as solid tumors and hematologic tumors). Examples of such tumors include lung tumor, prostate tumor, breast tumor, colon tumor, stomach tumor, pancreatic tumor, liver tumor (e.g., hepatocellular carcinoma, cholangiocarcinoma), esophageal tumor, brain tumor (e.g., glioblastoma), ovarian tumor, uterine tumor (e.g., uterine fibroids, endometrial cancer, cervical cancer), vaginal cancer, malignant melanoma, renal tumor, head and neck tumor, skin tumor, urinary tract tumor (e.g., bladder tumor, ureteral tumor, renal pelvic tumor), osteosarcoma, biliary tract tumor, vulval tumor, testicular tumor, penile tumor, rectal tumor, mediastinal tumor, urothelial tumor, villous tumor, soft tissue sarcoma, thyroid tumor, parathyroid tumor, adrenal tumor, malignant pheochromocytoma, germ cell tumor, mesothelial tumor, gastrointestinal stromal tumor, rhabdomyoma and rhabdosarcoma, leiomyoma and leiomyosarcoma, adipose tumor, angioma, fibroma, neuroma and neurosarcoma, cardiac tumor and small intestinal tumor, as well as hematologic tumors (e.g., lymphomas (such as benign and malignant, Kaposi's sarcoma and Hodgkin's disease), leukemia (e.g., chronic leukemia, acute leukemia, lymphocytic leukemia, acute lymphocytic leukemia (ALL), chronic lymphocytic leukemia (CLL), myelogenous leukemia, acute myelogenous leukemia (AML), chronic myelogenouss leukemia (e.g., CML)), multiple myeloma, polycythemia vera, myelofibrosis, and primary thrombocythemia). Additionally, tumor cells derived from the above tumors may also be used for in vitro or in vivo treatment.

Therefore, an embodiment of the present invention is a pharmaceutical composition or an antitumor agent for treating tumor comprising the above purine derivative, or a pharmaceutically acceptable salt, solvate or hydrate thereof, or a prodrug thereof, and preferred target tumors may include lung cancer, prostate cancer, breast cancer, colon cancer, stomach cancer, pancreatic cancer, liver cancer, esophageal cancer, brain tumor, ovarian cancer, uterine cancer, malignant melanoma, renal cancer, head and neck cancer, skin cancer, bladder cancer, osteosarcoma, biliary tract cancer, vulva cancer, testicular tumor, penile cancer, rectal cancer, mediastinal tumor, urothelial cancer, villous cancer, soft-tissue sarcoma, thyroid cancer, parathyroid cancer, adrenal cancer, malignant pheochromocytoma, germ cell tumor, malignant lymphoma, leukemia and multiple myeloma.

More preferred target tumors of the pharmaceutical composition or antitumor agent of the present invention may include lung cancer, prostate cancer, breast cancer, colon cancer, stomach cancer, pancreatic cancer, liver cancer, esophageal cancer, brain tumor, ovarian cancer, uterine cancer, renal cancer, head and neck cancer, skin cancer, bladder cancer, vulval cancer, testicular tumor, rectal cancer, villous cancer, germ cell tumor, malignant lymphoma, leukemia and multiple myeloma, and even more preferred target tumors may include lung cancer, prostate cancer, breast cancer, stomach cancer, esophageal cancer, brain tumor, ovarian cancer, uterine cancer, head and neck cancer, vulva cancer, testicular tumor, villous cancer, germ cell tumor, malignant lymphoma, leukemia and multiple myeloma, but the invention is not limited thereto.

An appropriate dosing regimen may be determined based on well-known technical knowledge, information provided in the present specification, and experience regarding individual subjects that are being treated. Normally, it is preferred that the above purine derivative etc. be administered at a concentration allowing effective results to be obtained without causing dangerous or harmful side effects.

A "therapeutically effective amount" refers to an amount of the purine derivative of the present invention for improving disease symptoms when administered to a subject of treatment. The therapeutically effective amount of the above purine derivative etc. can vary depending on various factors, including the level of activity, metabolic stability, duration of action, elimination rate, mode of delivery (dosage regimen) and administration time of the respective compounds, in addition to the age, weight, general state of health, sex, and daily food and drink of the subject of treatment as well as the combination of agents at the time of administration (drug interactions) and severity of the symptoms to be treated. The therapeutically effective amount can be determined conventionally by those skilled in the art by considering well-known information in the relevant technical field and the present disclosure. A dosage may be administered in divided doses (e.g., two to four divided doses per day), or may be administered in a single dose daily. Additionally, administration can be done on a daily, weekly or monthly basis.

The above purine derivative etc. can, for example, be administered to patients in a dosage within a range of 0.1 to 2000 mg daily. When used as an oral agent, the dosage of the effective ingredient will differ depending on the symptoms, age and weight etc. of the patient, but as one example, for an adult weighing 60 kg, a daily dosage of 10 to 2000 mg may be administered once, or two to three times, or in further divided doses. When used for injections into blood vessels, the dosage will differ depending on the symptoms, age and weight etc. of the patient, but as one example, for an adult weighing 60 kg, a daily dosage of 10 to 1000 mg may be administered once, or two to three times, or in further divided doses. When administered into the thorax, abdominal cavity or medullary cavity, or when administered to a local site such as into the bladders, the dosage will differ depending on the symptoms of the patient, but a daily dosage of 1 to 1000 mg may be administered once, or two to three times, or in further divided doses. Moreover, in cases of eye drops, inhalation into the lungs or nasal cavity, or injection into inflamed articular cavity, the dosage will differ depending on the symptoms of the patient, but for an adult, a daily dose of 0.1 to 100 mg may be administered once, or two to three times, or in further divided doses.

When formulated in fixed dosages, the purine derivative etc. can be used within the above dosage ranges. Additionally, as combination formulations, the above purine derivative etc. within the above dosage ranges can be used with other pharmaceutically active agents within an approved dosage range. In cases where combination formulations are inappropriate, the purine derivative etc. may be consecutively used with other pharmaceutically active agents within an approved dosage range.

"Subjects (of treatment)" or "patients" include mammals and other organisms, especially humans. Therefore, the present method can be applied to both treatment of humans and veterinary use. Preferably, the "subject (of treatment)" or "patient" is a human.

Here, the "treat" or "therapy" with regard to diseases, abnormalities or syndromes includes the treatment of a disease state (tumor) characterized by abnormal cell growth, and includes at least one of (i) when a person is susceptible to a disease state but has not been diagnosed to have that disease, the prevention of the disease state from happening in that person; (ii) the inhibition of a disease state (or development of a disease); and (iii) the alleviation of a disease state (or the regression of a disease state). Preferably, it is the above (ii) or (iii), and it is more preferably the above (iii). Details concerning therapy can be confirmed by normal experiments, investigations, and the like by specialists in the relevant technical field.

While embodiments of the present invention have been described above, these are exemplifications of the present invention, and various constitutions other than the above can be adopted. For example, in the above embodiments, the explanations focused on uses as an antitumor agent and pharmaceutical uses as a therapeutic agent, but the intent is not to limit to any pharmaceutical use in particular. The present invention is envisioned to have a wide range of uses, such as animal medicaments, diagnostic agents and research reagents in addition to pharmaceutical uses, and there is no intent to exclude such uses.

EXAMPLES

Hereafter, the present invention shall be explained concretely by way of examples, but these are respectively examples, and the present invention is not limited thereto. Additionally, the commercially available reagents mentioned in the examples were used in accordance to the manufacturers' instructions for use or conventional methods unless particularly indicated.

[General Manufacturing Process]

The synthesis of representative 2-mercaptopurine derivatives (VIII) is efficiently carried out by a method as shown in Scheme 1 below.

Scheme 1

[Chem. 4]

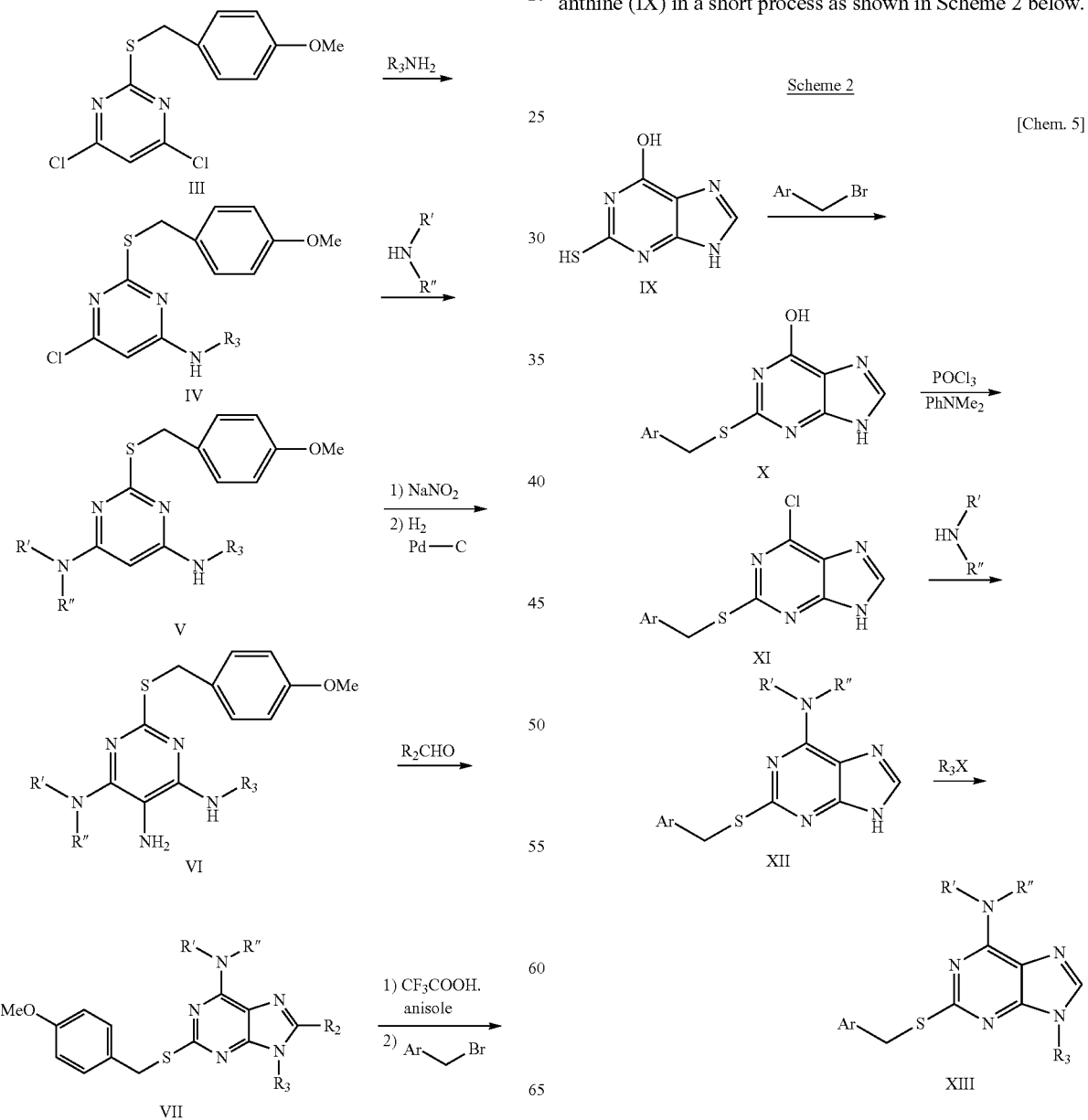

By using this synthetic method, various derivatives with different substituent groups can be synthesized.

Additionally, with regard to the synthesis of derivatives (XIII) not having a substituent group at position 8, the derivatives can be synthesized from commercially available thioxanthine (IX) in a short process as shown in Scheme 2 below.

Scheme 2

[Chem. 5]

Compounds having a substituent group at position 8 can be synthesized according to Scheme 3 below.

Scheme 3

[Chem. 6]

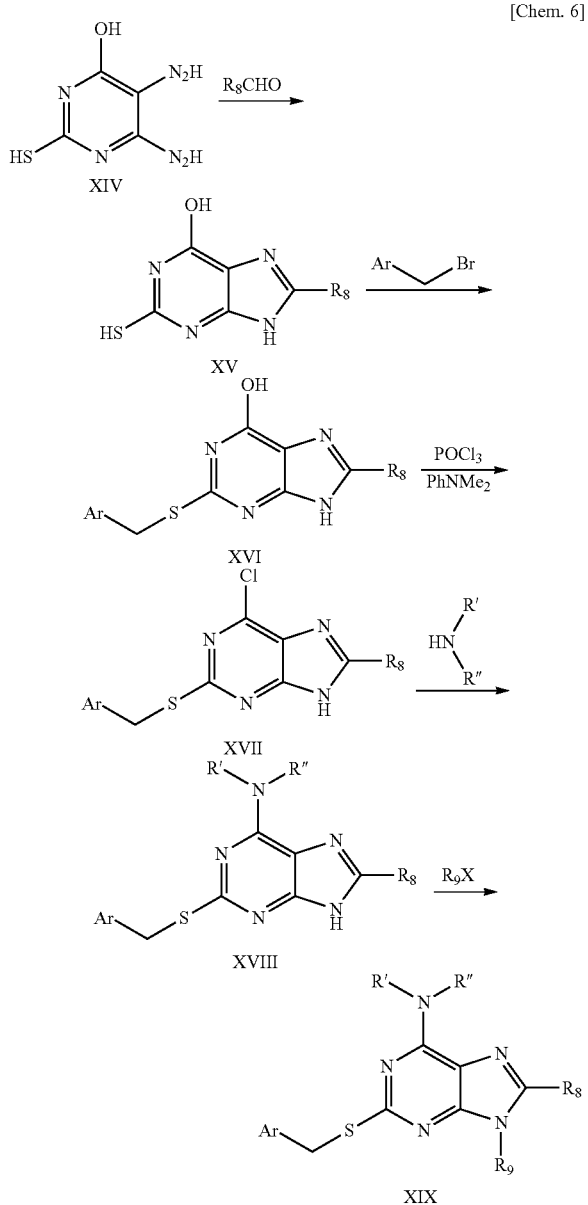

The manufacture of a 2-mercaptopurine derivative (VIII) represented in the above Scheme 1 is performed in seven steps from commercial product (I). In the synthesis of intermediate (II), a methoxybenzylsulfanyl pyrimidine derivative (II) can be obtained by using a solvent such as N,N-dimethylformamide (DMF) and adding to 2-mercaptopyrimidine an equivalent or excess amount of p-methoxybenzyl chloride in the presence of an equivalent or excess amount of amine, and allowing them to react at 0° C. to 150° C. for 1 to 24 hours, preferably at 100° C. for 2 hours.

In these reactions, reactions are carried out in a solvent and in the presence of a hydrogen chloride scavenger as necessary. Examples of the hydrogen chloride scavenger used in the reactions include sodium hydroxide, potassium hydroxide, sodium carbonate, potassium carbonate, triethylamine and pyridine, and examples of the solvent include acetone, toluene, hexane, xylene, dioxane, tetrahydrofuran or dichloroethane, DMF. This reaction may be performed using a base as the above solvent. Moreover, in cases where the amine has a low boiling point, it is preferably carried out in a sealed tube while being heated.

In the synthetic reaction of intermediate (III), a dichloropyrimidine derivative (III) with a chlorinated hydroxyl group can be obtained by adding to the methoxybenzylsulfanyl pyrimidine derivative (II), as a chlorinating agent and solvent, an amount of phosphorus oxychloride that is twice as much or in large excess, and after adding an amount of dimethylaniline ranging from a catalytic amount to five times as much, preferably twice as much, at −15° C. to room temperature, allowing them to react for 1 to 24 hours at 0° C. to 150° C., preferably for 2 hours at 100° C. The chlorinating agent is not limited to phosphorus oxychloride, and as the solvent, for example, toluene, xylene or the like may also be used. As the activating agent, other than dimethylaniline, other amines such as diethylaniline may also be used.

In the synthetic reaction of intermediate (IV), a monochloropyrimidine derivative (IV) can be obtained by reacting the dichloropyrimidine derivative (III) with an equivalent or excess amount of a primary amine at 0° C. to 100° C. for 1 to 24 hours. Moreover, in cases where the amine has a low boiling point, it is preferably carried out in a sealed tube while being heated. A solvent may be used and may react in the presence of a hydrogen chloride scavenger in addition to the reacting amine. Examples of the solvent include acetone, toluene, hexane, xylene, dioxane, tetrahydrofuran and dichloroethane and DMF.

In the synthetic reaction of intermediate (V), a diaminopyrimidine derivative (V) can be obtained by reacting the monochloropyrimidine derivative (IV) with an equivalent or excess amount of an amine at 0° C. to 100° C. for 1 to 72 hours, preferably at 80° C. for 24 hours. Moreover, in cases where the amine has a low boiling point, it is preferably carried out in a sealed tube while being heated. A solvent may be used and may react in the presence of a hydrogen chloride scavenger in addition to the reacting amine. Examples of the solvent include acetone, toluene, hexane, xylene, dioxane, tetrahydrofuran and dichloroethane and DMF.

In the synthetic reaction of intermediate (VI), the diaminopyrimidine derivative (V) may be dissolved in acetic acid, nitrosated at position 5 using sodium nitrite, and subsequently, without isolation or purification, converted to an amino group by catalytic reduction. By carrying out the nitrosation reaction at 0° C. to 40° C. for 1 to 24 hours, preferably at room temperature for 5 hours, a target 5-nitrosopyrimidine derivative can be obtained. As the solvent, other than acetic acid, an appropriate solvent, such as water, may be used. By carrying out the subsequent catalytic reduction at 0° C. to 60° C. for 1 to 24 hours, preferably at room temperature for 4 hours, a target 5-amino pyrimidine derivative (VI) can be obtained. When doing so, various metal catalysts (e.g., Pd catalyst, Pt catalyst or Ru catalyst) ranging from a catalytic amount to an equivalent amount (preferably a catalytic amount) may be used, and it is preferred that palladium-carbon be used. Additionally, an amine may be synthesized by reduction using, for example, iron, zinc or tin and hydrochloric acid etc. While examples of the solvent include ethyl acetate, ethanol, methanol, acetone, toluene, hexane, xylene, dioxane, tetrahydrofuran and dichloroethane and DMF, ethyl acetate is preferably used.

In the synthetic reaction of intermediate (VII), a purine skeleton may be constructed by a condensation reaction between the 5-aminopyrimidine derivative (VI) and an aldehyde. As the reaction conditions, by allowing it to react with an equivalent or excess amount of aldehyde at 0° C. to 100° C. for 1 to 24 hours, preferably at room temperature for 3 hours, a target product (VII) can be obtained. While examples of the solvent include ethanol, methanol, ethyl acetate, acetone, toluene, hexane, xylene, dioxane, tetrahydrofuran and dichloroethane and DMF, methanol is preferably used. In addition, in cases where the aldehyde has a low boiling point and heating is required, it is preferably carried out in a sealed tube while being heated.

In the synthetic reaction of final product (VIII), the intermediate (VII) is heated in a trifluoroacetic acid-anisole system to deprotect the p-methoxybenzyl group, freeing the mercapto group, then reacted with various substituted arylalkyl halides or substituted benzyl halides so as to be converted into a target product (VIII). The deprotection allows the final product to be obtained by reacting with excess trifluoroacetic acid and a catalytic amount of anisole at 0° C. to 150° C. for 1 to 72 hours, preferably at 80° C. for 24 hours. As the acid, other than trifluoroacetic acid, various organic acids or mineral acids (e.g., hydrochloric acid or hydrobromic acid) may be used. A hydrogen donor other than anisole may be used. In the subsequent benzylation reaction, reaction is carried out with an equivalent or excess amount of a substituted benzyl halide and, as necessary, in a solvent and in the presence of a hydrogen chloride scavenger. Examples of the hydrogen chloride scavenger used in this reaction include sodium hydroxide, potassium hydroxide, sodium carbonate, potassium carbonate, triethylamine and pyridine, and examples of the solvent include acetone, toluene, hexane, xylene, dioxane, tetrahydrofuran and dichloroethane and DMF.

With respect to the above Schemes 2 and 3, they can be carried out under the same conditions.

Example 1

Synthesis of 8-ethyl-2-(4-methoxybenzylsulfanyl)-9-methyl-6-morpholino-9H-purine (Compound 1)

(1-1) Synthesis of 4,6-dihydroxy-2-(4-methoxybenzylsulfanyl)pyrimidine

[Chem. 7]

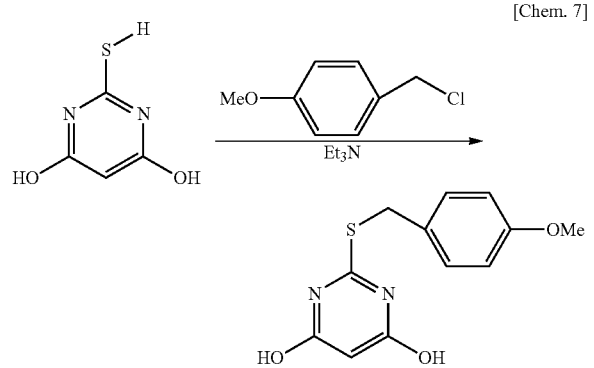

A DMF (500 ml) solution of 4,6-dihydroxy-2-mercaptopyrimidine (50 g, 346 mmol), triethylamine (62.7 ml, 450 mmol), 4-methoxybenzyl chloride (52.8 ml, 381 mmol) was heated and stirred at 100° C. for 1 hour 45 minutes. The reaction solution was poured into water and stirred for a while, and the precipitated crystals were collected by filtration and air-dried to obtain 75.2 g (82% yield) of 4,6-dihydroxy-2-(4-methoxybenzylsulfanyl)pyrimidine.

$^1$H-NMR (CDCl$_3$+CD$_3$OD) δ: 3.80(3H, s), 4.39(2H, s), 5.32(1H, s), 6.85(2H, d, J=8.9 Hz), 7.31(2H, d, J=8.9 Hz).

(1-2) Synthesis of 4,6-dichloro-2-(4-methoxybenzylsulfanyl)pyrimidine

[Chem. 8]

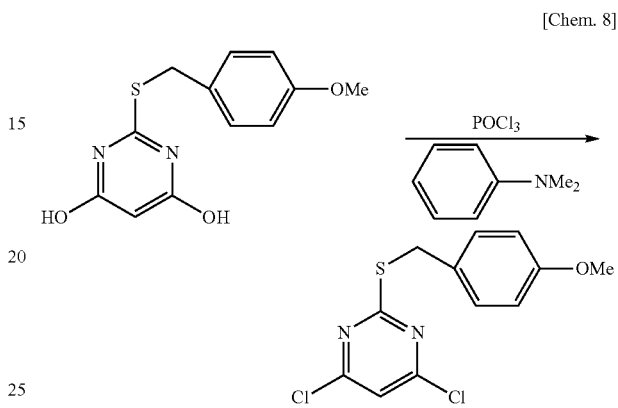

Phosphorus oxychloride (45.5 ml, 487 mmol) and dimethylaniline (20 ml, 162 mmol) were added to 4,6-dihydroxy-2-(4-methoxybenzylsulfanyl)pyrimidine (21.4 g, 81 mmol), and heated and stirred at 100° C. for 1.5 hours. The reaction solution was poured into ice water and extracted twice with ethyl acetate. After combining the ethyl acetate layers and washing with a saturated saline solution, it was dried with MgSO$_4$ and the solvent was distilled away under reduced pressure. Separation and purification were performed by silica gel column chromatography (hexane:ethyl acetate=20:1) to obtain 15.4 g (63% yield) of 4,6-dichloro-2-(4-methoxybenzylsulfanyl)pyrimidine.

$^1$H-NMR (CDCl$_3$) δ: 3.79(3H, s), 4.33(2H, s), 6.83(2H, d, J=8.7 Hz), 7.01(1H, s), 7.37(2H, d, J=8.7 Hz).

(1-3) Synthesis of 4-chloro-2-(4-methoxybenzylsulfanyl)-6-methylaminopyrimidine

[Chem. 9]

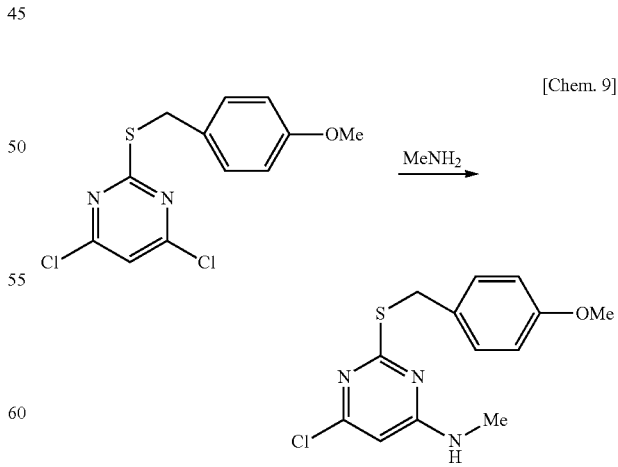

4,6-dichloro-2-(4-methoxybenzylsulfanyl)pyrimidine (3.0 g, 10 mmol) was dissolved in a 40% methylamine-methanol solution (20 ml) and stirred overnight at room temperature. The solvent was distilled away under reduced pressure, water was added and extracted twice with ethyl acetate. After combining the organic layers and washing with a saturated saline solution, it was dried with MgSO₄ and the solvent was distilled away under reduced pressure. Separation and purification were performed by silica gel column chromatography (hexane:ethyl acetate=1:2) to obtain 1.64 g (56% yield) of 4-chloro-2-(4-methoxybenzylsulfanyl)-6-methylaminopyrimidine.

$^1$H-NMR (CDCl$_3$) δ: 2.93(3H, d, J=5.2 Hz), 3.79(3H, s), 4.30(2H, s), 6.04(1H, s), 6.83(2H, d, J=8.8 Hz), 7.33(2H, d, J=8.8 Hz).

(1-4) Synthesis of 2-(4-methoxybenzylsulfanyl)-4-methylamino-6-morpholino pyrimidine

[Chem. 10]

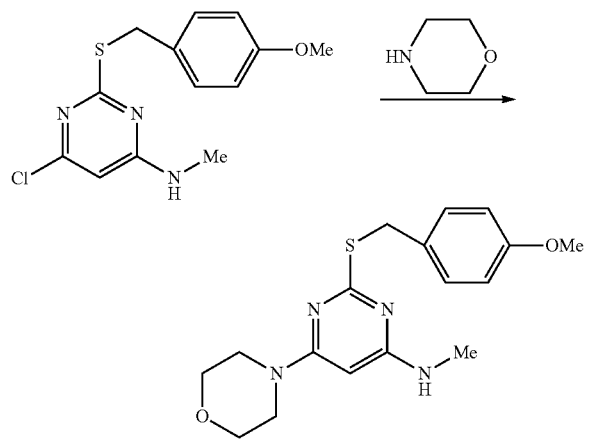

4-chloro-2-(4-methoxybenzylsulfanyl)-6-methyl aminopyrimidine (10.3 g, 35 mmol) was dissolved in morpholine (50 ml, 0.57 mol), and heated and stirred overnight at 80° C. After cooling to room temperature and distilling away morpholine under reduced pressure, water was added and extracted three times with ethyl acetate. After combining the organic layers, washing with water and drying with MgSO₄, the solvent was distilled away under reduced pressure. The residue was re-crystallized using ethanol to obtain 10.2 g (84% yield) of 2-(4-methoxybenzylsulfanyl)-4-methylamino-6-morpholinopyrimidine.

$^1$H-NMR (CDCl$_3$) δ: 2.86(3H, d, J=5.2 Hz), 3.52-3.56(4H, m), 3.73-3.77(4H, m), 3.78(3H, s), 4.29(2H, s), 4.66-4.69 (1H, m), 5.12(1H, s), 6.81(2H, d, J=8.6 Hz), 7.31(2H, d, J=8.6 Hz).

(1-5) Synthesis of 5-amino-2-(4-methoxybenzylsulfanyl)-6-methylamino-4-morpholinopyrimidine

[Chem. 11]

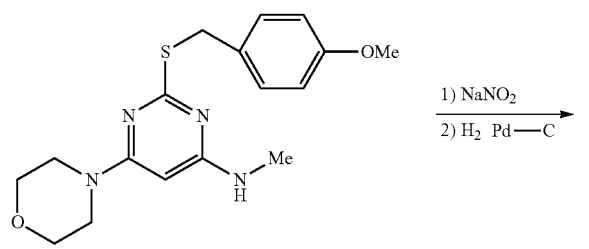

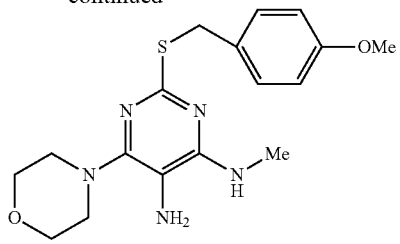

2-(4-methoxybenzylsulfanyl)-4-methylamino-6-morpholinopyrimidine (5.0 g, 14.4 mmol) was dissolved in acetic acid (50 ml), and an aqueous solution (10 ml) of sodium nitrite (1.49 g, 21.6 mmol) was added drop-wise under water cooling and stirred at room temperature for 5 hours. After distilling away acetic acid under reduced pressure and dissolving the residue in ethyl acetate, washing was performed in the order of 2N—NaOH solution and water, then dried with MgSO₄ and the solvent was distilled away under reduced pressure. The residue was dissolved in ethyl acetate (100 ml), 1.0 g of Pd/C was added and catalytic hydrogenation was performed under normal pressure for 4 hours. Celite was used to filter off Pd/C and the filtrate was distilled away under reduced pressure. Separation and purification were performed by silica gel column chromatography (ethyl acetate: hexane=2:1) to obtain 1.28 g (25% yield) of 5-amino-2-(4-methoxybenzylsulfanyl)-6-methylamino-4-morpholinopyrimidine. Melting point: 79.5 to 84° C. MS m/z: 361 (M⁺).

$^1$H-NMR (CDCl$_3$) δ: 2.82(2H, brs), 3.02(3H, d, J=5.1 Hz), 3.11-3.16(4H, m), 3.78(3H, s) 3.79-3.83(4H, m), 4.33(2H, s), 4.52-4.55(1H, m), 6.81(2H, d, J=8.6 Hz), 7.35(2H, d, J=8.6 Hz).

(1-6) Synthesis of 8-ethyl-2-(4-methoxybenzylsulfanyl)-9-methyl-6-morpholino-9H-purine

[Chem. 12]

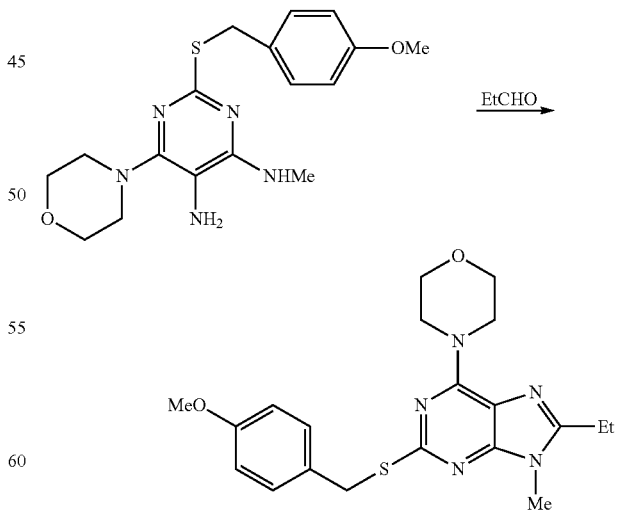

5-amino-2-(4-methoxybenzylsulfanyl)-6-methylamino-4-morpholinopyrimidine (693 mg, 1.91 mmol) was dissolved in methanol (20 ml), propionaldehyde (2.76 ml, 38.3 mmol) was added and stirred at room temperature for 3 hours. The solvent was distilled away under reduced pressure, water was added and extracted twice with ethyl acetate. After combining the organic layers and washing with a saturated saline solution, it was dried with MgSO$_4$ and the solvent was distilled away under reduced pressure. Separation and purification were performed by silica gel column chromatography (ethyl acetate:hexane=1:1) to obtain 610 mg (80% yield) of 8-ethyl-2-(4-methoxybenzylsulfanyl)-9-methyl-6-morpholino-9H-purine.

$^1$H-NMR (CDCl$_3$) δ: 1.36(3H, t, J=7.4 Hz), 2.80(2H, q, J=7.4 Hz), 3.65(3H, s), 3.78(3H, s), 3.80(4H, m), 4.25(4H, brs), 4.38(2H, s), 6.80(2H, d, J=8.6 Hz), 7.36(2H, d, J=8.6 Hz).

Example 2

Synthesis of 2-(3-amino-4-methoxybenzylsulfanyl)-8-ethyl-9-methyl-6-morpholino-9H-purine (Compound 2)

(2-1) Synthesis of 8-ethyl-9-methyl-6-morpholino-2-(3-nitro-4-methoxybenzylsulfanyl)-9H-purine

[Chem. 13]

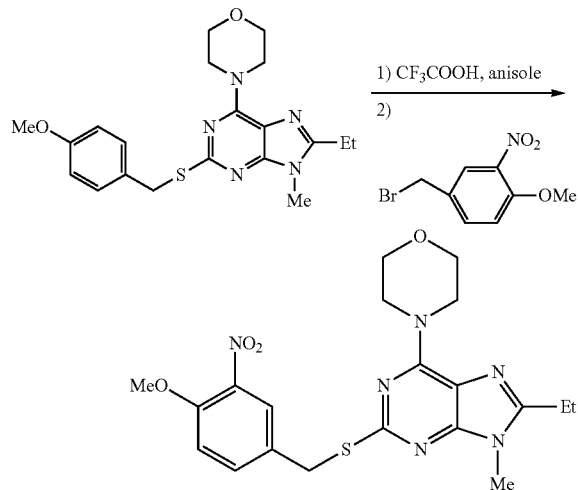

Trifluoroacetic acid (40 ml) and anisole (2.7 ml, 15 mmol) were added to 8-ethyl-2-(4-methoxybenzylsulfanyl)-9-methyl-6-morpholino-9H-purine (5.0 g, 12.5 mmol), and heated and stirred at 80° C. overnight. After distilling away trifluoroacetic acid under reduced pressure, neutralization was performed by adding excess triethylamine under ice cooling. After distilling away triethylamine under reduced pressure, the residue was dissolved in acetone (50 ml) and 3-nitro-4-methoxybenzyl bromide (3.69 g, 15 mmol) dissolved in acetone (10 ml) was added. After stirring at room temperature for 2.5 hours, the reaction solution was concentrated under reduced pressure, the residue was made to have a pH of approximately 7.0 by 2N—NaOH solution, and the precipitated crystals were collected by filtration. The obtained crystals were washed sequentially with hexane and ether to obtain 3.93 g (71% yield) of 8-ethyl-9-methyl-6-morpholino-2-(3-nitro-4-methoxybenzylsulfanyl)-9H-purine.

$^1$H-NMR (CDCl$_3$) δ: 1.36(3H, t, J=7.4 Hz), 2.80(2H, q, J=7.4 Hz), 3.67(3H, s), 3.78(4H, m), 3.92(3H, s), 4.23(4H, brs), 4.34(2H, s), 6.99(1H, m), 7.62(1H, m), 8.05(1H, m).

(2-2) Synthesis of 2-(3-amino-4-methoxybenzylsulfanyl)-8-ethyl-9-methyl-6-morpholino-9H-purine

[Chem. 14]

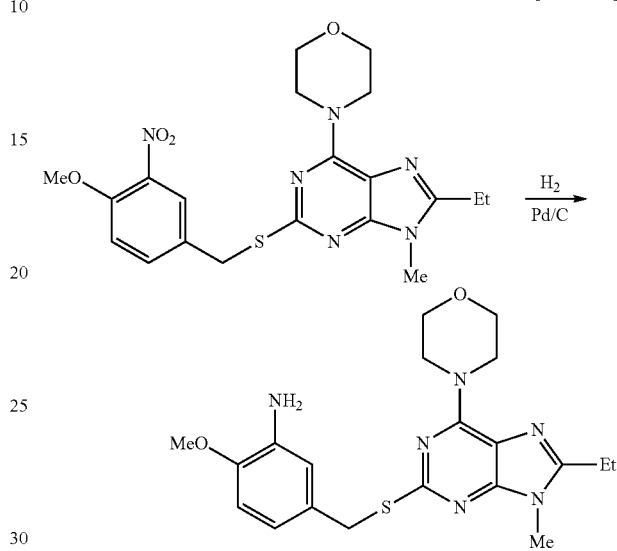

8-ethyl-9-methyl-6-morpholino-2-(3-nitro-4-methoxybenzylsulfanyl)-9H-purine (4.10 g, 9.23 mmol) was dissolved in dichloromethane (50 ml) and methanol (50 ml), 1.0 g of Pd/C was added and catalytic hydrogenation was performed under normal pressure for 18 hours. Celite was used to filter off Pd/C, and the filtrate was distilled away under reduced pressure. Ether was added to the residue and the precipitated crystals were collected by filtration to obtain 2.74 g (72% yield) of 2-(3-amino-4-methoxybenzylsulfanyl)-8-ethyl-9-methyl-6-morpholino-9H-purine.

Melting point: 139° C.

$^1$H-NMR (CDCl$_3$) δ: 1.36(3H, t, J=7.4 Hz), 2.80(2H, q, J=7.4 Hz), 3.62(3H, s), 3.79(4H, m), 3.82(3H, s), 4.24(4H, brs), 4.32(2H, s), 6.66-6.80(3H, m).

Various purine derivatives were synthesized using the same methods as Examples 1 and 2.

2-(4-methoxybenzylsulfanyl)-8,9-dimethyl-6-morpholino-9H-purine (Compound 3)

$^1$H-NMR (CDCl$_3$) δ: 2.49(3H, s), 3.65(3H, s), 3.78(3H, s), 3.78(4H, m), 4.22(4H, m), 4.38(2H, s), 6.82(2H, d, J=8.7 Hz), 7.36(2H, d, J=8.7 Hz).

2-(4-methoxybenzylsulfanyl)-9-methyl-6-morpholino-8-propyl-9H-purine (Compound 4)

$^1$H-NMR (CDCl$_3$) δ: 1.04(3H, t, J=7.3 Hz), 1.80(2H, m), 2.74(2H, m), 3.65(3H, s), 3.80(4H, m), 3.81(3H, s), 4.24(4H, m), 4.38(2H, s), 6.82(2H, d, J=8.7 Hz), 7.34(2H, d, J=8.7 Hz).

8-ethyl-2-(4-methoxycarbonylbenzylsulfanyl)-9-methyl-6-morpholino-9H-purine (Compound 5)

$^1$H-NMR (CDCl$_3$) δ: 1.38(3H, t, J=7.4 Hz), 2.78(2H, q, J=7.4 Hz), 3.64(3H, s), 3.77(4H, m), 3.89(3H, s), 4.22(4H, m), 4.44(2H, s), 7.50(2H, d, J=8.2 Hz), 7.96(2H, d, J=8.2 Hz).

8-ethyl-2-(4-methoxybenzylsulfanyl)-6-morpholino-9-propyl-9H-purine (Compound 6)

¹H-NMR (CDCl₃) δ: 0.93(3H, t, J=5.6 Hz), 1.25(3H, t, J=7.4 Hz), 1.78(2H, m), 2.77(2H, q, J=7.4 Hz), 3.77(3H, s), 3.78(4H, m), 4.04(2H, m), 4.25(4H, m), 4.36(2H, s), 6.80 (2H, d, J=8.4 Hz), 7.35(2H, d, J=8.4 Hz).

8-ethyl-2-(4-methoxybenzylsulfanyl)-9-methyl-6-(4-nitrosopiperazin-1-yl)-9H-purine (Compound 7)

¹H-NMR (CDCl₃) δ: 1.38(3H, t, J=7.6 Hz), 2.81(2H, q, J=7.6 Hz), 3.68(3H, s), 3.89(3H, s), 3.90(2H, m), 4.27-4.50 (6H, m), 4.38(2H, s), 6.82(2H, d, J=8.6 Hz), 7.36(2H, d, J=8.6 Hz).

8-ethyl-9-methyl-2-(4-methylbenzylsulfanyl)-6-morpholino-9H-purine (Compound 8)

¹H-NMR (CDCl₃) δ: 1.35(3H, t, J=7.4 Hz), 2.31(3H, s), 2.79(2H, q, J=7.4 Hz), 3.65(3H, s), 3.70(4H, m), 4.25(4H, m), 4.39(2H, s), 7.09(2H, d, J=8.1 Hz), 7.32(2H, d, J=8.1 Hz).

2-(4-methoxybenzylsulfanyl)-9-methyl-6-morpholino-9H-purine (Compound 9)

¹H-NMR (CDCl₃) δ: 3.75(3H, s), 3.78(3H, s), 3.78(4H, m), 4.25(4H, m), 4.38(2H, s), 6.80(2H, d, J=8.7 Hz), 7.34(2H, d, J=8.7 Hz), 7.69(1H, s).

8-ethyl-9-methyl-6-morpholino-2-(4-vinylbenzylsulfanyl)-9H-purine (Compound 10)

¹H-NMR (CDCl₃) δ: 1.36(3H, t, J=7.4 Hz), 2.79(2H, q, J=7.4 Hz), 3.65(3H, s), 3.78(4H, m), 4.25(4H, m), 4.41(2H, s), 5.18(1H, d, J=10.9 Hz), 5.70(1H, d, J=17.6 Hz), 6.66(1H, dd, J=10.9, 17.6 Hz), 7.33(2H, d, J=8.2 Hz), 7.40(2H, d, J=8.2 Hz).

8-ethyl-2-(3-fluoro-4-methylbenzylsulfanyl)-9-methyl-6-morpholino-9H-purine (Compound 11)

¹H-NMR (CDCl₃) δ: 1.36(3H, t, J=7.6 Hz), 2.22(3H, s), 2.80(2H, q, J=7.6 Hz), 3.63(3H, s), 3.78(4H, m), 4.25(4H, m), 4.36(2H, s), 7.03-7.14(3H, m).

8-ethyl-2-(4-ethylbenzylsulfanyl)-9-methyl-6-morpholino-9H-purine (Compound 12)

¹H-NMR (CDCl₃) δ: 1.21(3H, t, J=7.6 Hz), 1.36(3H, t, J=7.6 Hz), 2.59(2H, q, J=7.6 Hz), 2.80(2H, q, J=7.6 Hz), 3.65(3H, s), 3.78(4H, m), 4.25(4H, m), 4.40(2H, s), 7.10(2H, d, J=8.2 Hz), 7.35(2H, d, J=8.2 Hz).

8-ethyl-2-(3-hydroxy-4-methoxybenzylsulfanyl)-9-methyl-6-morpholino-9H-purine (Compound 13)

¹H-NMR (CDCl₃) δ: 1.36(3H, t, J=7.4 Hz), 2.80(2H, q, J=7.4 Hz), 3.68(3H, s), 3.78(4H, m), 3.85(3H, s), 4.25(4H, m), 4.43(2H, s), 5.54(1H, brs), 6.73(1H, m), 6.91(1H, m), 7.03(1H, m).

8-ethyl-2-(3-fluoro-4-methoxybenzylsulfanyl)-9-methyl-6-morpholino-9H-purine (Compound 14)

¹H-NMR (CDCl₃) δ: 1.36(3H, t, J=7.6 Hz), 2.79(2H, q, J=7.6 Hz), 3.66(3H, s), 3.78(4H, m), 3.86(3H, s), 4.25(4H, m), 4.43(2H, s), 6.86(1H, m), 7.13(1H, m), 7.23(1H, m).

2-(2-benzyloxy-4-methoxybenzylsulfanyl)-8-ethyl-9-methyl-6-morpholino-9H-purine (Compound 15)

¹H-NMR (CDCl₃) δ: 1.36(3H, t, J=6.7 Hz), 2.80(2H, q, J=6.7 Hz), 3.60(3H, s), 3.78(3H, s), 3.78(4H, m), 4.25(4H, m), 4.38(2H, s), 4.48(2H, s), 6.40-6.50(1H, m), 6.80(1H, m), 7.20-7.50(6H, m).

2-(3-chloro-4-methoxybenzylsulfanyl)-8-ethyl-9-methyl-6-morpholino-9H-purine (Compound 16)

¹H-NMR (CDCl₃) δ: 1.36(3H, t, J=7.6 Hz), 2.86(2H, q, J=7.6 Hz), 3.67(3H, s), 3.77(4H, m), 3.87(3H, s), 4.25(4H, m), 4.32(2H, s), 6.80(1H, m), 7.31(1H, m), 7.50(1H, m).

2-(4-ethoxybenzylsulfanyl)-8-ethyl-9-methyl-6-morpholino-9H-purine (Compound 17)

¹H-NMR (CDCl₃) δ: 1.36(6H, m), 2.80(2H, q, J=7.6 Hz), 3.65(3H, s), 3.77(4H, m), 4.00(2H, q, J=4.1 Hz), 4.25(4H, m), 4.37(2H, s), 6.78(2H, d, J=8.7 Hz), 7.30(2H, d, J=8.7 Hz).

2-(3-amino-4-methoxybenzylsulfanyl)-9-methyl-6-morpholino-9H-purine (Compound 18)

¹H-NMR (CDCl₃) δ: 3.75(3H, s), 3.78(4H, m), 3.82(3H, s), 4.25(4H, m), 4.33(2H, s), 6.67-6.92(3H, m), 7.58(1H, s).

2-(3-amino-4-methoxybenzylsulfanyl)-6-dimethylamino-9-methyl-9H-purine (Compound 19)

¹H-NMR (CDCl₃) δ: 3.50(6H, brs), 3.71(3H, s), 3.81(3H, s), 4.23(2H, s), 6.67-6.83(3H, m), 7.56(1H, s).

8-ethyl-2-(3-fluoro-4-methoxybenzylsulfanyl)-9-methyl-6-(4-nitrosopiperazin-1-yl)-9H-purine (Compound 20)

¹H-NMR (CDCl₃) δ: 1.38(3H, t, J=7.6 Hz), 2.82(2H, q, J=7.6 Hz), 3.68(3H, s), 3.86(3H, s), 3.89-3.93(4H, m), 4.25-4.33(2H, m), 4.35(2H, s), 4.36-4.49(2H, m), 6.87(1H, d, J=8.4 Hz), 6.96-7.25(2H, m).

6-dimethylamino-2-(4-methoxybenzylsulfanyl)-9-methyl-9H-purine (Compound 21)

¹H-NMR (CDCl₃) δ: 3.74(6H, brs), 3.74(3H, s), 3.78(3H, s), 4.2(2H, s), 6.84(2H, d, J=8.4 Hz), 7.37(2H, d, J=8.4 Hz), 7.57(1H, s).

8-ethyl-2-(4-methoxybenzylsulfanyl)-9-methyl-6-[(3S)-3-methyl-4-nitrosopiperazin-1-yl]-9H-purine (Compound 22)

¹H-NMR (CDCl₃) δ: 1.38(3H, t, J=7.4 Hz), 1.48(3H, t, J=6.6 Hz), 2.79(2H, q, J=7.4 Hz), 3.15-3.40(1H, m), 3.59-3.64(2H, m), 3.67(3H, s), 3.78(3H, s), 4.10-4.13(1H, m), 4.22-4.27(1H, m), 4.39(2H, s), 4.72-4.80(2H, m), 6.82(2H, d, J=8.5 Hz), 7.36(2H, d, J=8.5 Hz).

2-(3-amino-4-methoxybenzylsulfanyl)-6-dimethylamino-8-ethyl-9-methyl-9H-purine (Compound 23)

¹H-NMR (CDCl₃) δ: 1.36(3H, t, J=7.6 Hz), 2.80(2H, q, J=7.6 Hz), 3.48(6H, brs), 3.64(3H, s), 3.82(3H, s), 4.36(2H, s), 6.68(1H, d, J=8.1 Hz), 6.77-6.83(2H, m).

6-dimethylamino-8-ethyl-2-(4-methoxybenzylsulfanyl)-9-methyl-9H-purine (Compound 24)

¹H-NMR (CDCl₃) δ: 1.36(3H, t, J=7.5 Hz), 2.80(2H, q, J=7.5 Hz), 3.48(6H, brs), 3.64(3H, s), 3.77(3H, s), 4.41(2H, s), 6.83(2H, d, J=8.7 Hz), 7.36(2H, d, J=8.7 Hz).

6-diethylamino-2-(4-methoxybenzylsulfanyl)-9-methyl-9H-purine (Compound 25)

$^1$H-NMR (CDCl$_3$) δ: 1.25(6H, t, J=6.6 Hz), 3.72(3H, s), 3.78(3H, s), 3.95(4H, brs), 4.41(2H, s), 6.82(2H, d, J=8.7 Hz), 7.37(2H, d, J=8.7 Hz), 7.57(1H, s).

2-(4-methoxybenzylsulfanyl)-9-methyl-6-methylamino-9H-purine (Compound 26)

$^1$H-NMR (CDCl$_3$) δ: 3.18(3H, d, J=4.1 Hz), 3.75(3H, s), 3.78(3H, s), 4.43(2H, s), 5.62(1H, brs), 6.82(2H, d, J=8.7 Hz), 7.38(2H, d, J=8.7 Hz), 7.52(1H, s).

Example 3

Synthesis of 2-(3-acetylamino-4-methoxybenzylsulfanyl)-8-ethyl-9-methyl-6-morpholino-9H-purine (Compound 27)

[Chem. 15]

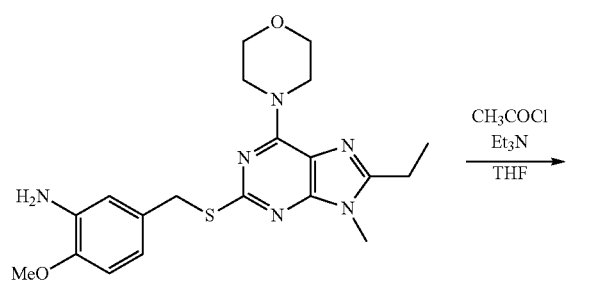

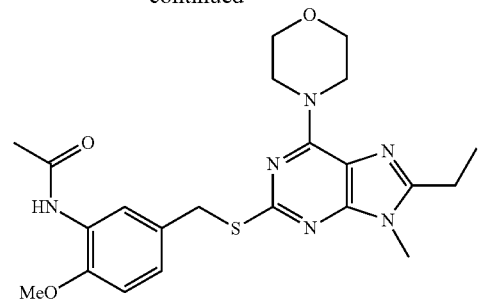

2-(3-amino-4-methoxybenzylsulfanyl)-8-ethyl-9-methyl-6-morpholino-9H-purine (100 mg, 0.24 mmol) was dissolved in tetrahydrofuran (10 ml), triethylamine (49 mg, 0.48 mmol) and acetyl chloride (38 mg, 0.48 mmol) were added and stirred at room temperature overnight. After adding water to the reaction solution and extracting twice with ethyl acetate, the organic layers were washed with a saturated saline solution and dried with MgSO$_4$. After distilling away the solvent under reduced pressure, purification was performed by silica gel column chromatography (ethyl acetate:hexane=1:1) to obtain 77 mg (70% yield) of Compound 27.

$^1$H-NMR (CDCl$_3$) δ: 1.35(3H, t, J=7.4 Hz), 2.18(3H, s), 2.79(2H, q, J=7.4 Hz), 3.67(3H, s), 3.70-3.81(4H, m), 3.84(3H, s), 4.10-4.24(4H, m), 4.38(2H, s), 6.77(1H, d, J=8.7 Hz), 7.15(1H, dd, J=2.1, 8.7 Hz), 7.27(1H, brs), 8.47(1H, brs).

Example 4

Synthesis of 2-[3-(2-aminoacetylamino)-4-methoxybenzylsulfanyl]-8-ethyl-9-methyl-6-morpholino-9H-purine hydrochloride (Compound 28)

[Chem. 16]

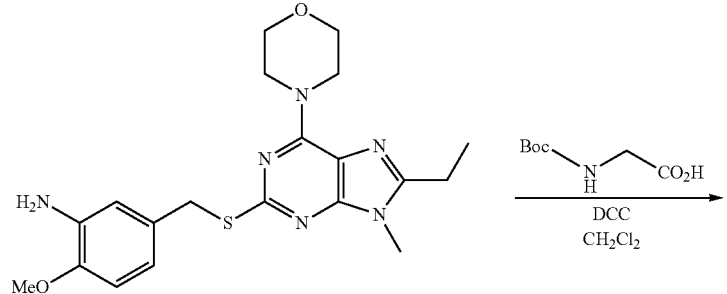

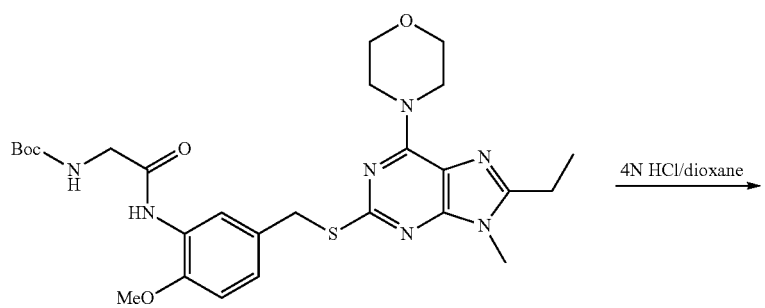

-continued

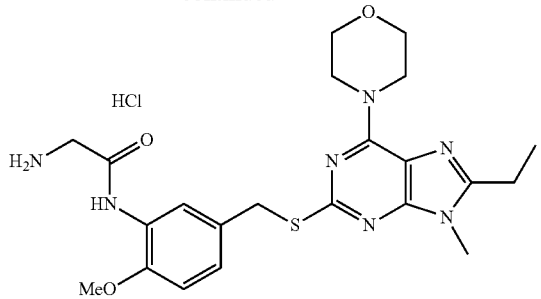

(4-1) Synthesis of 2-[3-(2-tert-butoxycarbonylaminoacetylamino)-4-methoxybenzyl sulfanyl]-8-ethyl-9-methyl-6-morpholino-9H-purine 2-(3-amino-4-methoxybenzylsulfanyl)-8-ethyl-9-methyl-6-morpholino-9H-purine (170 mg, 0.41 mmol) was dissolved in dichloromethane (10 ml), N,N-dicyclohexylcarbodiimide (85 mg, 0.41 mmol) and N—BOC glycine (72 mg, 0.41 mmol) were added and stirred at room temperature for 4 hours. Ethyl acetate (10 ml) was added, the insolubles were filtered off, and the filtrate was distilled away under reduced pressure. Purification was performed by silica gel column chromatography (ethyl acetate:hexane=3:1) to obtain 146 mg (62% yield) of 2-[3-(2-tert-butoxycarbonylaminoacetylamino)-4-methoxybenzylsulfanyl]-8-ethyl-9-methyl-6-morpholino-9H-purine (Compound 62).

$^1$H-NMR (CDCl$_3$) δ: 1.35(3H, t, J=7.6 Hz), 1.48(9H, s), 2.78(2H, q, J=7.6 Hz), 3.66(3H, s), 3.77-3.81(4H, m), 3.83 (3H, s), 3.92(2H, d, J=5.7 Hz), 4.24(4H, brs), 4.38(2H, s), 5.20(1H, brs), 6.89(1H, d, J=8.4 Hz), 7.16(1H, dd, J=2.0, 8.4 Hz), 8.29(1H, brs), 8.46(1H, d, J=2.0 Hz).

(4-2) Synthesis of 2-[3-(2-aminoacetylamino)-4-methoxybenzylsulfanyl]-8-ethyl-9-methyl-6-morpholino-9H-purine hydrochloride (Compound 28)

2-[3-(2-tert-butoxycarbonylaminoacetylamino)-4-methoxybenzylsulfanyl]-8-ethyl-9-methyl-6-morpholino-9H-purine (Compound 62) (140 mg, 0.24 mmol) was dissolved in tetrahydrofuran (15 ml), 4N-hydrogen chloride in dioxane (2 ml) and stirred for 8 hours. After distilling away the solvent under reduced pressure, the residue was washed with ether to obtain 103 mg (83% yield) of Compound 28.

$^1$H-NMR (DMSO-d$_6$) δ: 1.25(3H, t, J=7.6 Hz), 2.81(2H, q, J=7.6 Hz), 3.63(3H, s), 3.65-3.71(4H, m), 3.80(3H, s), 3.83 (2H, d, J=5.7 Hz), 4.12(4H, brs), 4.31(2H, s), 6.99(1H, d, J=8.6 Hz), 7.14-7.18(1H, m), 8.06-8.10(1H, m), 8.18(1H, brs).

The following compounds were synthesized according to the methods of the above Examples 1 to 4.

9-(2-acetylaminoethyl)-8-ethyl-2-(4-methoxybenzylsulfanyl)-6-morpholino-9H-purine (Compound 29)

$^1$H-NMR (CDCl$_3$) δ: 1.36(3H, t, J=7.6 Hz), 1.87(3H, s), 2.78(2H, q, J=7.6 Hz), 3.57(2H, m), 3.78(3H, s), 3.82(4H, m), 4.23(2H, m), 4.25(4H, brs), 4.35(2H, s), 6.58(1H, brs), 6.84 (2H, d, J=8.7 Hz), 7.36(2H, d, J=8.7 Hz).

8-ethyl-9-(2-fluoroethyl)-2-(4-methoxybenzylsulfanyl)-6-morpholino-9H-purine (Compound 30)

$^1$H-NMR (CDCl$_3$) δ: 1.34(3H, t, J=7.4 Hz), 2.85(2H, q, J=7.4 Hz), 3.77(3H, s), 3.78(4H, m), 4.26(4H, brs), 4.34(2H, s), 4.36(2H, m), 4.69(2H, dt, J=4.8, 47.3 Hz), 6.81(2H, d, J=8.4 Hz), 7.33(2H, d, J=8.4 Hz).

8-ethyl-2-(4-fluoromethylbenzylsulfanyl)-9-methyl-6-morpholino-9H-purine (Compound 31)

$^1$H-NMR (CDCl$_3$) δ: 1.36(3H, t, J=7.5 Hz), 2.80(2H, q, J=7.5 Hz), 3.65(3H, s), 3.78(4H, m), 4.10(4H, brs), 4.43(2H, s), 5.32(2H, d, J=48.0 Hz), 7.30(2H, d, J=7.4 Hz), 7.48(2H, d, J=7.4 Hz).

8-ethyl-9-methyl-2-(4-methylsulfanylbenzylsulfanyl)-6-morpholino-9H-purine (Compound 32)

$^1$H-NMR (CDCl$_3$) δ: 1.36(3H, t, J=7.6 Hz), 2.46(3H, s), 2.80(2H, q, J=7.6 Hz), 3.51(3H, s), 3.78(4H, m), 4.23(4H, brs), 4.38(2H, brs), 7.18(2H, d, J=8.1 Hz), 7.36(2H, d, J=8.1 Hz).

8-ethyl-2-(2-fluoro-4-methoxybenzylsulfanyl)-9-methyl-6-morpholino-9H-purine (Compound 33)

$^1$H-NMR (CDCl$_3$) δ: 1.40(3H, t, J=7.6 Hz), 2.82(2H, q, J=7.6 Hz), 3.68(3H, s), 3.78(3H, s), 3.79(4H, m), 4.24(4H, brs), 4.38(2H, s), 6.59(2H, m), 7.38(1H, m).

6-(4-acetylpiperazin-1-yl)-8-ethyl-2-(4-methoxybenzylsulfanyl)-9-methyl-9H-purine (Compound 34)

$^1$H-NMR (CDCl$_3$) δ: 1.37(3H, t, J=7.6 Hz), 2.14(3H, s), 2.80(2H, q, J=7.6 Hz), 3.52-3.56(2H, m), 3.66(3H, s), 3.68-3.72(2H, m), 3.78(3H, s), 4.22-4.28(4H, m), 4.38(2H, s), 6.82(2H, d, J=8.7 Hz), 7.35(2H, d, J=8.7 Hz).

2-(4-dimethylaminobenzylsulfanyl)-8-ethyl-9-methyl-6-morpholino-9H-purine (Compound 35)

$^1$H-NMR (CDCl$_3$) δ: 1.35(3H, t, J=7.6 Hz), 2.78(2H, q, J=7.6 Hz), 2.91(6H, s), 3.66(3H, s), 3.79(4H, m), 4.25(4H, brs), 4.37(2H, s), 6.65(2H, d, J=8.9 Hz), 7.31(2H, d, J=8.9 Hz).

2-(benzo[1,3]dioxol-5-yl-methylsulfanyl)-8-ethyl-9-methyl-6-morpholino-9H-purine (Compound 36)

$^1$H-NMR (CDCl$_3$) δ: 1.33(3H, t, J=7.6 Hz), 2.80(2H, q, J=7.6 Hz), 3.66(3H, s), 3.79(4H, m), 4.25(4H, brs), 4.35(2H, s), 5.91(2H, s), 6.69-6.96(3H, m).

8-ethyl-2-(4-methoxy-3-methylbenzylsulfanyl)-9-methyl-6-morpholino-9H-purine (Compound 37)

$^1$H-NMR (CDCl$_3$) δ: 1.36(3H, t, J=7.6 Hz), 2.17(3H, s), 2.81(2H, q, J=7.6 Hz), 3.66(3H, s), 3.80(3H, s), 3.82(4H, m), 4.25(4H, brs), 4.35(2H, s), 6.70-6.80(2H, m), 7.21(1H, m).

8-ethyl-2-[1-(4-methoxyphenyl)ethylsulfanyl]-9-methyl-6-morpholino-9H-purine (Compound 38)

$^1$H-NMR (CDCl$_3$) δ: 1.35(3H, t, J=7.6 Hz), 1.74(3H, d, J=7.1 Hz), 2.77(2H, q, J=7.6 Hz), 3.64(3H, s), 3.78(3H, s), 3.78(4H, m), 4.23(4H, brs), 5.00(1H, q, J=7.1 Hz), 6.82(2H, d, J=8.9 Hz), 7.40(2H, d, J=8.9 Hz).

8-ethyl-2-(3-methoxycarbonylamino-4-methoxybenzylsulfanyl)-9-methyl-6-morpholino-9H-purine (Compound 39)

$^1$H-NMR (CDCl$_3$) δ: 1.36(3H, t, J=7.6 Hz), 2.79(2H, q, J=7.6 Hz), 3.66(3H, s), 3.76(3H, s), 3.77-3.81(4H, m), 3.82(3H, s), 4.24(4H, brs), 4.38(2H, s), 6.76(1H, d, J=8.2 Hz), 7.10(1H, dd, J=2.1, 8.2 Hz), 7.26(1H, d, J=2.1 Hz), 8.19(1H, brs).

2-(3-amino-4-methylbenzylsulfanyl)-8-ethyl-9-methyl-6-morpholino-9H-purine (Compound 40)

$^1$H-NMR (CDCl$_3$) δ: 1.35(3H, t, J=7.6 Hz), 2.12(3H, s), 2.79(2H, q, J=7.6 Hz), 3.64(3H, s), 3.78(4H, t, J=4.8 Hz), 4.22-4.26(4H, m), 4.33(2H, s), 6.75-6.77(2H, m), 6.95(1H, d, J=8.1 Hz).

2-(5-chloro-3-methyl-1-phenyl-1H-pyrazol-4-ylmethylsulfanyl)-8-ethyl-9-methyl-6-morpholino-9H-purine (Compound 41)

$^1$H-NMR (CDCl$_3$) δ: 1.37(3H, t, J=7.5 Hz), 2.38(3H, s), 2.81(2H, q, J=7.5 Hz), 3.68(3H, s), 3.80(4H, m), 4.29(4H, brs), 4.38(2H, s), 7.35-7.55(5H, m).

8-ethyl-2-(6-methoxynaphthalen-2-ylmethylsulfanyl)-9-methyl-6-morpholino-9H-purine (Compound 42)

$^1$H-NMR (CDCl$_3$) δ: 1.37(3H, t, J=7.6 Hz), 2.79(2H, q, J=7.6 Hz), 3.67(3H, s), 3.78(4H, t, J=4.9 Hz), 3.98(3H, s), 4.25(4H, brs), 4.85(2H, s), 6.73(1H, d, J=7.9 Hz), 7.60(3H, m), 8.15(1H, d, J=3.9 Hz), 8.28(1H, s).

8-ethyl-2-(4-methoxynaphthalen-1-ylmethylsulfanyl)-9-methyl-6-morpholino-9H-purine (Compound 43)

$^1$H-NMR (CDCl$_3$) δ: 1.36(3H, t, J=7.6 Hz), 2.79(2H, q, J=7.6 Hz), 3.67(3H, s), 3.77(4H, t, J=4.9 Hz), 3.90(3H, s), 4.31(4H, brs), 4.56(2H, s), 7.11(2H, m), 7.55(1H, dd, J=1.7, 8.5 Hz), 7.66(2H, d, J=8.5 Hz), 8.81(1H, s).

8-ethyl-2-[2-(4-methoxyphenyl)ethylsulfanyl]-9-methyl-6-morpholino-9H-purine (Compound 44)

$^1$H-NMR (CDCl$_3$) δ: 1.37(3H, t, J=7.6 Hz), 2.80(2H, q, J=7.6 Hz), 2.97-3.03(2H, m), 3.31-3.37(2H, m), 3.66(3H, s), 3.79(3H, s), 3.79-3.83(4H, m), 4.27(4H, brs), 6.85(2H, d, J=8.6 Hz), 7.18(2H, d, J=8.6 Hz).

2-(3-amino-4-methoxybenzylsulfanyl)-9-methyl-6-methylamino-9H-purine (Compound 45)

$^1$H-NMR (CDCl$_3$) δ: 3.19(3H, brs), 3.76(3H, s), 3.82(3H, s), 4.38(2H, s), 5.66(1H, brs), 6.69(1H, d, J=7.8 Hz), 6.79-6.84(2H, m), 7.57(1H, s).

2-(4-bromobenzylsulfanyl)-8-ethyl-9-methyl-6-morpholino-9H-purine (Compound 46)

$^1$H-NMR (CDCl$_3$) δ: 1.36(3H, t, J=7.5 Hz), 2.79(2H, q, J=7.5 Hz), 3.64(3H, s), 3.78(4H, m), 4.23(4H, brs), 4.35(2H, s), 7.29-7.40(4H, m).

8-ethyl-2-[2-(4-fluorobenzoyl)ethylsulfanyl]-9-methyl-6-morpholino-9H-purine (Compound 47)

$^1$H-NMR (CDCl$_3$) δ: 1.36(3H, t, J=7.6 Hz), 2.79(2H, q, J=7.6 Hz), 3.48-3.54(4H, m), 3.62(3H, s), 3.77(4H, t, J=4.9 Hz), 4.22(4H, brs), 7.10-7.13(2H, m), 7.96-8.01(2H, m).

8-ethyl-2-[2-(4-methylbenzoyl)ethylsulfanyl]-9-methyl-6-morpholino-9H-purine (Compound 48)

$^1$H-NMR (CDCl$_3$) δ: 1.36(3H, t, J=7.5 Hz), 2.40(3H, s), 2.79(2H, q, J=7.5 Hz), 3.49-3.51(4H, m), 3.62(3H, s), 3.75-3.77(4H, m), 4.22(4H, brs), 7.24(2H, d, J=8.2 Hz), 7.86(2H, d, J=8.2 Hz).

8-ethyl-2-(4-iodobenzylsulfanyl)-9-methyl-6-morpholino-9H-purine (Compound 49)

$^1$H-NMR (CDCl$_3$) δ: 1.36(3H, t, J=7.6 Hz), 2.80(2H, q, J=7.6 Hz), 3.64(3H, s), 3.78(4H, t, J=4.8 Hz), 4.21-4.25(4H, m), 4.34(2H, s), 7.20(2H, d, J=8.4 Hz), 7.59(2H, d, J=8.4 Hz).

8-ethyl-2-[3-(4-methoxyphenyl)propylsulfanyl]-9-methyl-6-morpholino-9H-purine (Compound 50)

$^1$H-NMR (CDCl$_3$) δ: 1.36(3H, t, J=7.5 Hz), 2.00-2.11(2H, m), 2.72(2H, t, J=7.5 Hz), 2.78(2H, q, J=7.5 Hz), 3.15(2H, t, J=7.2 Hz), 3.61(3H, s), 3.78(3H, s), 3.79-3.81(4H, m), 4.22(4H, brs), 6.82(2H, d, J=8.7 Hz), 7.11(2H, d, J=8.7 Hz).

2-(3-cyano-4-methoxybenzylsulfanyl)-8-ethyl-9-methyl-6-morpholino-9H-purine (Compound 51)

$^1$H-NMR (CDCl$_3$) δ: 1.36(3H, t, J=7.6 Hz), 2.80(2H, q, J=7.6 Hz), 3.67(3H, s), 3.78(4H, m), 3.90(3H, s), 4.24(4H, brs), 4.32(2H, s), 6.87(1H, s), 7.60(1H, m), 7.69(1H, m).

8-ethyl-2-(4-methoxy-3-pivaloylaminobenzylsulfanyl)-9-methyl-6-morpholino-9H-purine (Compound 52)

$^1$H-NMR (CDCl$_3$) δ: 1.31(9H, s), 1.35(3H, t, J=7.6 Hz), 2.79(2H, q, J=7.6 Hz), 3.66(3H, s), 3.77-3.81(4H, m), 3.86(3H, s), 4.24(4H, brs), 4.38(2H, s), 6.78(1H, d, J=8.4 Hz), 7.15(1H, dd, J=2.1, 8.4 Hz), 8.09(1H, s), 8.56(1H, d, J=2.1 Hz).
MS m/z: 498 (M$^+$).

8-ethyl-2-(4-methoxy-3-propionylaminobenzylsulfanyl)-9-methyl-6-morpholino-9H-purine (Compound 53)

$^1$H-NMR (CDCl$_3$) δ: 1.24(3H, t, J=7.5 Hz), 1.35(3H, t, J=7.5 Hz), 2.40(2H, q, J=7.5 Hz), 2.79(2H, q, J=7.5 Hz), 3.66(3H, s), 3.77-3.80(4H, m), 3.84(3H, s), 4.24(4H, brs), 4.38(2H, s), 6.77(1H, d, J=8.4 Hz), 7.14(1H, dd, J=1.9, 8.4 Hz), 7.72(1H, s), 8.52(1H, d, J=1.9 Hz).

MS m/z: 470 (M$^+$).

2-(3-cyclopropancarbonylamino-4-methoxybenzylsulfanyl)-8-ethyl-9-methyl-6-morpholino-9H-purine (Compound 54)

$^1$H-NMR (CDCl$_3$) δ: 0.80-0.85(2H, m), 1.04-1.06(2H, m), 1.35(3H, t, J=7.4 Hz), 1.54-1.56(1H, m), 2.78(2H, q, J=7.4 Hz), 3.65(3H, s), 3.76-3.79(4H, m), 3.86(3H, s), 4.23(4H, brs), 4.36(2H, s), 6.78(1H, d, J=8.3 Hz), 7.13(1H, dd, J=2.1, 8.3 Hz), 7.90(1H, brs), 8.48(1H, d, J=2.1 Hz).

8-ethyl-2-[3-(2-furylcarbonylamino)-4-methoxybenzylsulfanyl]-9-methyl-6-morpholino-9H-purine (Compound 55)

$^1$H-NMR (CDCl$_3$) δ: 1.34(3H, t, J=7.5 Hz), 2.79(2H, q, J=7.5 Hz), 3.67(3H, s), 3.78-3.81(4H, m), 3.89(3H, s), 4.24(4H, brs), 4.41(2H, s), 6.53(1H, dd, J=1.7, 3.6 Hz), 6.82(1H, d, J=8.4 Hz), 7.17-7.24(2H, m), 7.51(1H, dd, J=1.4, 1.7 Hz), 8.62(1H, d, J=1.4 Hz), 8.72(1H, s).

2-(3-dimethylaminocarbonylamino-4-methoxybenzylsulfanyl)-8-ethyl-9-methyl-6-morpholino-9H-purine (Compound 56)

$^1$H-NMR (CDCl$_3$) δ: 1.36(3H, t, J=7.5 Hz), 2.80(2H, q, J=7.5 Hz), 3.04(6H, brs), 3.65(3H, s), 3.78-3.85(4H, m), 3.82(3H, s), 4.26(4H, brs), 4.37(2H, s), 6.76(1H, d, J=8.2 Hz), 6.94(1H, d, J=2.1 Hz), 7.06(1H, dd, J=2.1, 8.2 Hz), 7.52(1H, s).

2-(3-dimethylsulfamoylamino-4-methoxybenzylsulfanyl)-8-ethyl-9-methyl-6-morpholino-9H-purine (Compound 57)

$^1$H-NMR (CDCl$_3$) δ: 1.37(3H, t, J=7.5 Hz), 2.70(6H, s), 2.80(2H, q, J=7.5 Hz), 3.69(3H, s), 3.78-3.82(4H, m), 3.86(3H, s), 4.25(4H, brs), 4.36(2H, s), 6.79(1H, d, J=8.5 Hz), 6.82(1H, s), 7.13(1H, dd, J=2.1, 8.5 Hz), 7.65(1H, d, J=2.1 Hz).

MS m/z: 521 (M$^+$).

2-(3-dimethylaminothiocarbonylamino-4-methoxybenzylsulfanyl)-8-ethyl-9-methyl-6-morpholino-9H-purine (Compound 58)

$^1$H-NMR (CDCl$_3$) δ: 1.33(3H, t, J=7.5 Hz), 2.79(2H, q, J=7.5 Hz), 3.31(6H, s), 3.66(3H, s), 3.78-3.82(4H, m), 3.83(3H, s), 4.25(4H, brs), 4.41(2H, s), 6.79(1H, d, J=8.4 Hz), 7.16(1H, dd, J=2.1, 8.4 Hz), 7.34(1H, s), 8.13(1H, d, J=2.1 Hz).

8-ethyl-2-[3-(4-fluorobenzoylamino)-4-methoxybenzylsulfanyl]-9-methyl-6-morpholino-9H-purine (Compound 59)

$^1$H-NMR (CDCl$_3$) δ: 1.35(3H, t, J=7.5 Hz), 2.79(2H, q, J=7.5 Hz), 3.68(3H, s), 3.78-3.81(4H, m), 3.89(3H, s), 4.26 (4H, brs), 4.43(2H, s), 6.83(1H, d, J=8.4 Hz), 7.12-7.22(3H, m), 7.85-7.92(2H, m), 8.44(1H, s), 8.64(1H, d, J=2.1 Hz).

2-(3-acetylamino-4-methoxybenzylsulfanyl)-6-dimethylamino-8-ethyl-9-methyl-9H-purine (Compound 60)

$^1$H-NMR (CDCl$_3$) δ: 1.36(3H, t, J=7.6 Hz), 2.17(3H, s), 2.79(2H, q, J=7.6 Hz), 3.48(6H, brs), 3.65(3H, s), 3.84(3H, s), 4.42(2H, s), 6.78(1H, d, J=8.4 Hz), 7.16(1H, dd, J=2.1, 8.4 Hz), 7.70(1H, brs), 8.46(1H, d, J=2.1 Hz).

6-(N-acetyl-N-methylamino)-2-(4-methoxybenzylsulfanyl)-9-methyl-9H-purine (Compound 61)

$^1$H-NMR (CDCl$_3$) δ: 2.03(3H, s), 3.59(3H, s), 3.78(3H, s), 3.86(3H, s), 4.42(2H, s), 6.84(2H, d, J=8.7 Hz), 7.38(2H, d, J=8.7 Hz), 7.88(1H, s).

8-ethyl-2-(3-methoxyacetylamino-4-methoxybenzylsulfanyl)-9-methyl-6-morpholino-9H-purine (Compound 63)

$^1$H-NMR (CDCl$_3$) δ: 1.35(3H, t, J=7.5 Hz), 2.79(2H, q, J=7.5 Hz), 3.50(3H, s), 3.66(3H, s), 3.77-3.81(4H, m), 3.86(3H, s), 4.01(2H, s), 4.25(4H, brs), 4.39(2H, s), 6.80(1H, d, J=8.5 Hz), 7.18(1H, dd, J=2.1, 8.5 Hz), 8.51(1H, d, J=2.1 Hz), 8.81(1H, s).

6-ethylamino-2-(4-methoxybenzylsulfanyl)-9-methyl-9H-purine (Compound 64)

$^1$H-NMR (CDCl$_3$) δ: 1.28(3H, t, J=7.3 Hz), 3.69(2H, brs), 3.76(3H, s), 3.78(3H, s), 4.42(2H, s), 5.62(1H, brs), 6.83(2H, d, J=8.7 Hz), 7.38(2H, d, J=8.7 Hz), 7.58(1H, s).

8-ethyl-6-(N-ethyl-N-methylamino)-2-(4-methoxybenzylsulfanyl)-9-methyl-9H-purine (Compound 65)

$^1$H-NMR (CDCl$_3$) δ: 1.20(3H, t, J=7.1 Hz), 1.36(3H, t, J=7.5 Hz), 2.80(2H, q, J=7.5 Hz), 3.41(3H, brs), 3.64(3H, s), 3.78(3H, s), 4.01(2H, brs), 4.41(2H, s), 6.82(2H, d, J=8.7 Hz), 7.37(2H, d, J=8.7 Hz).

[2-(3-trans-cinnamoylamino)-4-methoxybenzylsulfanyl]-8-ethyl-9-methyl-6-morpholino-9H-purine (Compound 66)

$^1$H-NMR (CDCl$_3$) δ: 1.35(3H, t, J=7.5 Hz), 2.78(2H, q, J=7.5 Hz), 3.67(3H, s), 3.77-3.81(4H, m), 3.87(3H, s), 4.25 (4H, brs), 4.41(2H, s), 6.58(1H, d, J=15.5 Hz), 6.80(1H, d, J=8.4 Hz), 7.18(1H, dd, J=2.1, 8.4 Hz), 7.36-7.40(3H, m), 7.53-7.56(2H, m), 7.70(1H, d, J=15.5 Hz), 7.93(1H, s), 8.65 (1H, d, J=2.1 Hz).

2-(3-dimethylamino-4-methoxybenzylsulfanyl)-8-ethyl-9-methyl-6-morpholino-9H-purine (Compound 67)

$^1$H-NMR (CDCl$_3$) δ: 1.37(3H, t, J=7.6 Hz), 2.76(6H, s), 2.80(2H, q, J=7.6 Hz), 3.66(3H, s), 3.79-3.82(4H, m), 3.86 (3H, s), 4.26(4H, brs), 4.39(2H, s), 6.76(1H, d, J=8.7 Hz), 7.03-7.06(2H, m).

8-ethyl-6-(N-ethyl-N-methylamino)-2-(4-iodobenzylsulfanyl)-9-methyl-9H-purine (Compound 68)

¹H-NMR (CDCl₃) δ: 1.19(3H, t, J=7.1 Hz), 1.36(3H, t, J=7.6 Hz), 2.79(2H, q, J=7.6 Hz), 3.41(3H, brs), 3.63(3H, s), 4.01(2H, brs), 4.37(2H, s), 7.21(2H, d, J=8.4 Hz), 7.59(2H, d, J=8.4 Hz).

2-(3-cyano-4-methoxybenzylsulfanyl)-6-dimethylamino-8-ethyl-9-methyl-9H-purine (Compound 69)

¹H-NMR (CDCl₃) δ: 1.36(3H, t, J=7.4 Hz), 2.80(2H, q, J=7.4 Hz), 3.47(6H, brs), 3.65(3H, s), 3.89(3H, s), 4.36(2H, s), 6.87(1H, d, J=8.6 Hz), 7.62(1H, dd, J=2.2, 8.6 Hz), 7.69(1H, d, J=2.2 Hz).

2-[3-(iso-butoxycarbonylamino)-4-methoxybenzylsulfanyl]-8-ethyl-9-methyl-6-morpholino-9H-purine (Compound 70)

¹H-NMR (CDCl₃) δ: 0.96(6H, d, J=6.8 Hz), 1.35(3H, t, J=7.6 Hz), 1.97(1H, m), 2.79(2H, q, J=7.6 Hz), 3.66(3H, s), 3.77-3.81(4H, m), 3.83(3H, s), 3.93(2H, d, J=6.8 Hz), 4.25(4H, brs), 4.38(2H, s), 6.76(1H, d, J=8.4 Hz), 7.10(1H, d, J=8.4 Hz), 7.18(1H, s), 8.21(1H, s).

6-dimethylamino-8-ethyl-2-(3-fluoro-4-methoxybenzylsulfanyl)-9-methyl-9H-purine (Compound 71)

¹H-NMR (CDCl₃) δ: 1.36(3H, t, J=7.5 Hz), 2.79(2H, q, J=7.5 Hz), 3.48(6H, brs), 3.63(3H, s), 3.84(3H, s), 4.37(2H, s), 6.81-7.12(1H, m), 7.19-7.20(1H, m), 7.23-7.24(1H, m).

2-(3-cyano-4-methoxybenzylsulfanyl)-6-methylamino-9-methyl-9H-purine (Compound 72)

¹H-NMR (CDCl₃) δ: 3.17(3H, brs), 3.77(3H, s), 3.89(3H, s), 4.36(2H, s), 5.64(1H, brs), 6.88(1H, d, J=8.7 Hz), 7.59(1H, s), 7.64(1H, dd, J=2.1, 8.7 Hz), 7.73(1H, d, J=2.1 Hz).

2-(3-fluoro-4-methoxybenzylsulfanyl)-6-methylamino-9-methyl-9H-purine (Compound 73)

¹H-NMR (CDCl₃) δ: 3.18(3H, brs), 3.76(3H, s), 3.85(3H, s), 4.39(2H, s), 5.10(1H, brs), 6.83-6.89(1H, m), 7.14-7.21(2H, m), 7.58(1H, s).

6-diethylamino-8-ethyl-2-(4-methoxybenzylsulfanyl)-9-methyl-9H-purine (Compound 74)

¹H-NMR (CDCl₃) δ: 1.22(6H, t, J=7.0 Hz), 1.36(3H, t, J=7.5 Hz), 2.79(2H, q, J=7.5 Hz), 3.40(2H, dd, J=5.0, 10.0 Hz), 3.63(3H, s), 3.78(3H, s), 3.94(2H, brs), 4.41(2H, s), 6.82(2H, d, J=8.7 Hz), 7.36(2H, d, J=8.7 Hz).

6-(N-ethyl-N-methylamino)-2-(4-methoxybenzylsulfanyl)-9-methyl-9H-purine (Compound 75)

¹H-NMR (CDCl₃) δ: 1.24(3H, t, J=7.0 Hz), 3.42(3H, brs), 3.74(3H, s), 3.80(3H, s), 4.05(2H, brs), 4.42(2H, s), 6.82(2H, d, J=8.7 Hz), 7.37(2H, d, J=8.7 Hz), 7.57(1H, s).

6-acetylamino-2-(4-methoxybenzylsulfanyl)-9-methyl-9H-purine (Compound 76)

¹H-NMR (CDCl₃) δ: 2.64(3H, s), 3.79(3H, s), 3.83(3H, s), 4.43(2H, s), 6.84(2H, d, J=8.6 Hz), 7.37(2H, d, J=8.6 Hz), 7.81(1H, s), 8.51(1H, brs).

8-ethyl-2-(3-heptoxycarbonylamino-4-methoxybenzylsulfanyl)-9-methyl-6-morpholino-9H-purine (Compound 77)

¹H-NMR (CDCl₃) δ: 0.86(3H, t, J=6.5 Hz), 1.29-1.38(8H, m), 1.35(3H, t, J=7.5 Hz), 1.61-1.72(2H, m), 2.79(2H, q, 7.5 Hz), 3.66(3H, s), 3.77-3.81(4H, m), 3.83(3H, s), 4.14(2H, t, J=6.7 Hz), 4.25(4H, brs), 4.38(2H, s), 6.76(1H, d, J=8.3 Hz), 7.09(1H, d, J=8.3 Hz), 7.17(1H, s), 8.22(1H, s).

2-(3-bromo-4-methoxybenzylsulfanyl)-8-ethyl-9-methyl-6-morpholino-9H-purine (Compound 78)

¹H-NMR (CDCl₃) δ: 1.36(3H, t, J=7.6 Hz), 2.80(2H, q, J=7.6 Hz), 3.66(3H, s), 3.78(4H, m), 3.86(3H, s), 4.25(4H, brs), 4.32(2H, s), 6.81(1H, m), 7.35(1H, m), 7.68(1H, m).

8-ethyl-2-(4-methoxy-3-vinylbenzylsulfanyl)-9-methyl-6-morpholino-9H-purine (Compound 79)

¹H-NMR (CDCl₃) δ: 1.36(3H, t, J=7.4 Hz), 2.80(2H, q, J=7.4 Hz), 3.65(3H, s), 3.79(4H, m), 3.82(3H, s), 4.25(4H, brs), 4.37(2H, s), 5.25(1H, dd, J=1.5, 11.2 Hz), 5.70(1H, dd, J=1.5, 17.7 Hz), 6.80(1H, m), 7.00(1H, dd, J=11.2, 17.7 Hz), 7.34(1H, m), 7.55(1H, m).

2-(3-cyano-4-methoxybenzylsulfanyl)-9-methyl-6-morpholino-9H-purine (Compound 80)

¹H-NMR (CDCl₃) δ: 3.73(3H, s), 3.77(4H, m), 3.91(3H, s), 4.25(4H, brs), 4.33(2H, s), 6.89(1H, m), 7.60(1H, s), 7.63(1H, m), 7.75(1H, m).

8-ethyl-2-[3-(N-acetylcarbamoyl)-4-methoxybenzylsulfanyl]-9-methyl-6-morpholino-9H-purine (Compound 81)

¹H-NMR (CDCl₃) δ: 1.35(3H, t, J=7.6 Hz), 2.78(2H, q, J=7.6 Hz), 2.99(3H, d, J=4.9 Hz), 3.69(3H, s), 3.78(4H, m), 3.92(3H, s), 4.23(4H, brs), 4.39(2H, s), 6.90(1H, d, J=8.6 Hz), 7.55(1H, dd, J=2.3, 8.6 Hz), 7.75(1H, s), 8.32(1H, d, J=2.3 Hz).

6-(N-ethyl-N-methylamino)-2-(3-fluoro-4-methoxybenzylsulfanyl)-9-methyl-9H-purine (Compound 82)

¹H-NMR (CDCl₃) δ: 1.23(3H, t, J=7.1 Hz), 3.41(3H, brs), 3.74(3H, s), 3.86(3H, s), 4.04(2H, brs), 4.38(2H, s), 6.87(1H, t, J=8.4 Hz), 7.15(1H, d, J=8.4 Hz), 7.22(1H, m), 7.58(1H, s).

2-(3-fluoro-4-methoxybenzylsulfanyl)-9-methyl-6-morpholino-9H-purine (Compound 83)

¹H-NMR (CDCl₃) δ: 3.76(3H, s), 3.81(4H, m), 3.86(3H, s), 4.25(4H, brs), 4.35(2H, s), 6.86(1H, m), 7.13(1H, m), 7.23(1H, m), 7.59(1H, s).

2-(3-amino-4-methoxybenzylsulfanyl)-6-(N-ethyl-N-methylamino)-9-methyl-9H-purine (Compound 84)

¹H-NMR (CDCl₃) δ: 1.24(3H, t, J=7.0 Hz), 3.42(3H, brs), 3.71(3H, s), 3.73(2H, brs), 3.80(3H, s), 4.08(2H, brs), 4.36(2H, s), 6.68-6.70(1H, m), 6.77-6.83(2H, m), 7.57(1H, s).

2-(3-cyano-4-methoxybenzylsulfanyl)-6-(N-ethyl-N-methylamino)-9-methyl-9H-purine (Compound 85)

$^1$H-NMR (CDCl$_3$) δ: 1.23(3H, t, J=6.9 Hz), 3.39(3H, brs), 3.75(3H, s), 3.90(3H, s), 4.04(2H, brs), 4.36(2H, s), 6.89(1H, d, J=8.7 Hz), 7.59(1H, s), 7.63(1H, dd, J=2.3, 8.7 Hz), 7.69(1H, d, J=2.3 Hz).

6-dimethylamino-2-(3-fluoro-4-methoxybenzylsulfanyl)-9-methyl-9H-purine (Compound 86)

$^1$H-NMR (CDCl$_3$) δ: 3.50(6H, brs), 3.74(3H, s), 3.85(3H, s), 4.38(2H, s), 6.83-6.89(1H, m), 7.13-7.25(2H, m), 7.58(1H, s).

2-(3-cyano-4-methoxybenzylsulfanyl)-6-dimethylamino-9-methyl-9H-purine (Compound 87)

$^1$H-NMR (CDCl$_3$) δ: 3.49(6H, brs), 3.75(3H, s), 3.89(3H, s), 4.36(2H, s), 6.88(1H, d, J=8.5 Hz), 7.55-7.64(2H, m), 7.70(1H, s).

6-(2-ethoxymorpholino)-2-(4-methoxybenzylsulfanyl)-9-methyl-9H-purine (Compound 88)

$^1$H-NMR (CDCl$_3$) δ: 1.23(3H, t, J=7.0 Hz), 1.57(2H, s), 3.56-3.87(8H, m), 4.01-4.39(7H, m), 6.82(2H, d, J=6.8 Hz), 7.37(2H, d, J=8.6 Hz), 7.59(1H, s).

2-(3-cyano-4-methoxybenzylsulfanyl)-6-ethylamino-9-methyl-9H-purine (Compound 89)

$^1$H-NMR (CDCl$_3$) δ: 1.27(3H, t, J=7.3 Hz), 3.65(2H, brs), 3.76(3H, s), 3.89(3H, s), 4.35(2H, s), 5.88(1H, brs), 6.89(1H, d, J=8.7 Hz), 7.59(1H, s), 7.63(1H, dd, J=2.2, 8.7 Hz), 7.71(1H, d, J=2.2 Hz).

2-(3-amino-4-ethylbenzylsulfanyl)-8-ethyl-9-methyl-6-morpholino-9H-purine (Compound 90)

$^1$H-NMR (CDCl$_3$) δ: 1.20(3H, t, J=7.5 Hz), 1.36(3H, t, J=7.6 Hz), 2.47(2H, q, J=7.5 Hz), 2.79(2H, q, J=7.6 Hz), 3.65(3H, s), 3.76-3.80(4H, m), 4.24(4H, brs), 4.34(2H, s), 6.78-6.82(2H, m), 6.97(1H, d, J=7.6 Hz).

6-ethylamino-2-(3-fluoro-4-methoxybenzylsulfanyl)-9-methyl-9H-purine (Compound 91)

$^1$H-NMR (CDCl$_3$) δ: 1.28(3H, t, J=7.3 Hz), 3.68(2H, brs), 3.76(3H, s), 3.86(3H, s), 4.38(2H, s), 5.46(1H, brs), 6.87(1H, t, J=8.6 Hz), 7.16-7.26(2H, m), 7.58(1H, s).

2-(3-amino-4-methoxybenzylsulfanyl)-6-ethylamino-9-methyl-9H-purine (Compound 92)

$^1$H-NMR (CDCl$_3$) δ: 1.28(3H, t, J=7.2 Hz), 3.69-3.71(4H, m), 3.74(3H, s), 3.82(3H, s), 4.36(2H, s), 5.80(1H, brs), 6.69(1H, d, J=8.1 Hz), 6.78-6.84(2H, m), 7.56(1H, s).

9-(2-cyclopropylmethyl)-2-(4-methoxybenzylsulfanyl)-6-morpholino-9H-purine (Compound 93)

$^1$H-NMR (CDCl$_3$) δ: 0.42(2H, dt, J=4.9, 5.9 Hz), 0.64(2H, dt, J=4.9, 5.9 Hz), 1.21-1.36(1H, m), 3.78(3H, s), 3.81(4H, t, J=4.6 Hz), 3.97(2H, d, J=7.3 Hz), 4.27(4H, brs), 4.37(2H, s), 6.82(2H, d, J=8.6 Hz), 7.36(2H, d, J=8.6 Hz), 7.72(1H, s).

2-(3-cyano-4-methoxybenzylsulfanyl)-8,9-diethyl-6-morpholino-9H-purine (Compound 94)

$^1$H-NMR (CDCl$_3$) δ: 1.38(6H, t, J=7.4 Hz), 2.85(2H, q, J=7.4 Hz), 3.80(4H, m), 3.89(3H, s), 4.13(2H, q, J=7.4 Hz), 4.24(4H, brs), 4.32(2H, s), 6.87(1H, m), 7.61(1H, m), 7.67(1H, m).

2-(4-methoxybenzylsulfanyl)-6-morpholino-9-oxiranylmethyl-9H-purine (Compound 95)

$^1$H-NMR (CDCl$_3$) δ: 2.49(1H, dd, J=2.4, 4.6 Hz), 2.84(1H, t, J=4.1 Hz), 3.29-3.37(1H, m), 3.78(3H, s), 3.80(4H, t, J=4.6 Hz), 4.11(1H, d, J=5.9 Hz), 4.15(1H, d, J=5.9 Hz), 4.28(4H, brs), 4.37(2H, s), 6.82(2H, d, J=8.6 Hz), 7.35(2H, d, J=8.6 Hz), 7.68(1H, s).

9-allyl-2-(4-methoxybenzylsulfanyl)-6-morpholino-9H-purine (Compound 96)

$^1$H-NMR (CDCl$_3$) δ: 3.78(3H, s), 3.81(4H, t, J=4.9 Hz), 4.27(4H, brs), 4.37(2H, s), 4.75(2H, dd, J=1.4, 5.7 Hz), 5.17-5.31(2H, m), 5.90-6.10(1H, m), 6.82(2H, d, J=8.6 Hz), 7.36(2H, d, J=8.6 Hz), 7.61(1H, s).

2-(3-amino-4-methoxybenzylsulfanyl)-8,9-diethyl-6-morpholino-9H-purine (Compound 97)

$^1$H-NMR (CDCl$_3$) δ: 1.37(6H, m), 2.80(2H, q, J=7.4 Hz), 3.78(4H, m), 3.82(3H, s), 4.13(2H, q, J=7.3 Hz), 4.25(4H, brs), 4.32(2H, s), 6.66-6.82(3H, m).

2-(4-methoxybenzylsulfanyl)-6-morpholino-9-propargyl-9H-purine (Compound 98)

$^1$H-NMR (CDCl$_3$) δ: 2.49(1H, t, J=2.7 Hz), 3.77(3H, s), 3.79(4H, t, J=4.6 Hz), 4.25(4H, brs), 4.37(2H, s), 4.90(2H, d, J=2.7 Hz), 6.82(2H, d, J=8.6 Hz), 7.35(2H, d, J=8.6 Hz), 7.81(1H, s).

2-(4-ethoxybenzylsulfanyl)-9-methyl-6-morpholino-9H-purine (Compound 99)

$^1$H-NMR (CDCl$_3$) δ: 1.39(3H, t, J=6.9 Hz), 3.75(3H, s), 3.79(4H, m), 4.00(2H, q, J=6.9 Hz), 4.26(4H, brs), 4.38(2H, s), 6.81(2H, d, J=8.6 Hz), 7.34(2H, d, J=8.6 Hz), 7.58(1H, s).

2-benzhydrylsulfanyl-8-ethyl-9-methyl-6-morpholino-9H-purine (Compound 100)

$^1$H-NMR (CDCl$_3$) δ: 1.32(3H, t, J=7.6 Hz), 2.75(2H, q, J=7.3 Hz), 3.58(3H, s), 3.67(4H, dd, J=4.6, 4.9 Hz), 4.12(4H, brs), 6.23(1H, s), 7.17-7.30(6H, m), 7.46-7.49(4H, m).

6-cyclopropylamino-2-(4-methoxybenzylsulfanyl)-9-methyl-9H-purine (Compound 101)

$^1$H-NMR (CDCl$_3$) δ: 0.60-0.66(2H, m), 0.84-0.91(2H, m), 3.07(1H, brs), 3.67(3H, s), 3.78(3H, s), 4.46(2H, s), 5.77(1H, brs), 6.82(2H, d, J=8.6 Hz), 7.40(2H, d, J=8.6 Hz), 7.58(1H, s).

9-ethyl-2-(4-methoxybenzylsulfanyl)-8-methyl-6-morpholino-9H-purine (Compound 102)

$^1$H-NMR (CDCl$_3$) δ: 1.36(3H, t, J=7.3 Hz), 2.51(3H, s), 3.78(3H, s), 3.78(4H, m), 4.12(2H, q, J=7.3 Hz), 4.22, (4H, brs), 4.37(2H, s), 6.81(2H, d, J=8.7 Hz), 7.35(2H, d, J=8.7 Hz).

2-(3-amino-4-ethoxybenzylsulfanyl)-8-ethyl-9-methyl-6-morpholino-9H-purine (Compound 103)

$^1$H-NMR (CDCl$_3$) δ: 1.36(3H, t, J=7.6 Hz), 1.39(3H, t, J=7.1 Hz), 2.78(2H, q, J=7.6 Hz), 3.65(3H, s), 3.79(4H, m), 4.02(2H, q, J=7.1 Hz), 4.25(4H, brs), 4.32(2H, s), 6.65-6.82 (3H, m).

2-(4-methoxybenzylsulfanyl)-9-ethyl-6-morpholino-8-propyl-9H-purine (Compound 104)

$^1$H-NMR (CDCl$_3$) δ: 1.00(3H, m), 1.36(3H, t, J=7.3 Hz), 1.80(2H, m), 2.75(2H, m), 3.77(3H, s), 3.78(4H, m), 4.12 (2H, q, J=7.3 Hz), 4.25(4H, brs), 4.37(2H, s), 6.80(2H, d, J=8.7 Hz), 7.34(2H, d, J=8.7 Hz).

6-(N-methoxy-N-methylamino)-2-(4-methoxybenzylsulfanyl)-9-methyl-9H-purine (Compound 105)

$^1$H-NMR (CDCl$_3$) δ: 3.53(3H, s), 3.77(3H, s), 3.78(3H, s), 3.93(3H, s), 4.41(2H, s), 6.83(2H, d, J=8.6 Hz), 7.37(2H, d, J=8.6 Hz), 7.69(1H, s).

2-(3-amino-4-ethoxybenzylsulfanyl)-8,9-diethyl-6-morpholino-9H-purine (Compound 106)

$^1$H-NMR (CDCl$_3$) δ: 1.37(6H, m), 1.39(3H, t, J=7.4 Hz), 2.79(2H, q, J=7.4 Hz), 3.79(4H, m), 4.12(4H, m), 4.25(4H, brs), 4.31(2H, s), 6.68-6.82(3H, m).

2-(3-amino-4-ethoxybenzylsulfanyl)-9-methyl-6-methylamino-9H-purine (Compound 107)

$^1$H-NMR (CDCl$_3$) δ: 1.41(3H, t, J=6.9 Hz), 3.19(3H, brs), 3.75(3H, s), 4.02(2H, q, J=6.9 Hz), 4.37(2H, s), 5.65(1H, brs), 6.67(1H, d, J=7.8 Hz), 6.77-6.84(2H, m), 7.51(1H, s).

2-(4-methoxybenzylsulfanyl)-6-[(2-methoxyethyl)-methyl-amino]-9-methyl-9H-purine (Compound 108)

$^1$H-NMR (CDCl$_3$) δ: 3.34(3H, s), 3.40-3.60(5H, brs), 3.66 (2H, m), 3.74(3H, s), 3.78(3H, s), 4.41(2H, s), 6.82(2H, d, J=8.7 Hz), 7.37(2H, d, J=8.7 Hz), 7.57(1H, s).

9-methyl-2-(4-methoxybenzylsulfanyl)-6-(1-pyrrolyl)-9H-purine (Compound 109)

$^1$H-NMR (CDCl$_3$) δ: 3.79(3H, s), 3.85(3H, s), 4.49(2H, s), 6.41(2H, t, J=2.3 Hz), 6.84(2H, d, J=8.7 Hz), 7.40(2H, d, J=8.7 Hz), 7.86(1H, s), 8.28(2H, t, J=2.3 Hz).

6-(imidazol-1-yl)-2-(4-methoxybenzylsulfanyl)-9-methyl-9H-purine (Compound 110)

$^1$H-NMR (CDCl$_3$) δ: 3.79(3H, s), 3.88(3H, s), 4.48(2H, s), 6.85(2H, d, J=8.6 Hz), 7.23(1H, brs), 7.40(2H, d, J=8.6 Hz), 7.92(1H, s), 8.34(1H, brs), 9.10(1H, brs).

6-(2-ethoxymorpholino)-8-ethyl-2-(4-methoxybenzylsulfanyl)-9-methyl-9H-purine (Compound 111)

$^1$H-NMR (CDCl$_3$) δ: 1.22(3H, t, J=7.1 Hz), 1.35(3H, t, J=7.6 Hz), 2.80(2H, q, J=7.6 Hz), 3.62 (2H, q, J=7.1 Hz), 3.63(3H, s), 3.77(3H, s), 3.80-3.90(2H, m), 4.10-4.20(2H, m), 4.25-4.35(2H, brs), 4.38(2H, s), 4.65-4.75(1H, m), 6.81 (2H, d, J=8.7 Hz), 7.36(2H, d, J=8.7H).

3-[2-(4-methoxybenzylsulfanyl)-9-methyl-9H-purin-6-yl]-1-methyl-imidazolinium iodide (Compound 112)

$^1$H-NMR (CDCl$_3$) δ: 3.77(3H, s), 3.95(3H, s), 4.38(3H, s), 4.50(2H, s), 6.83(2H, d, J=8.6 Hz), 7.40(2H, d, J=8.6 Hz), 7.94(1H, brs), 8.36(1H, s), 8.60(1H, brs), 10.52(1H, brs).

2-(3-amino-4-propoxybenzylsulfanyl)-8-ethyl-9-methyl-6-morpholino-9H-purine (Compound 113)

$^1$H-NMR (CDCl$_3$) δ: 1.03(3H, t, J=7.4 Hz), 1.36(3H, t, J=7.6 Hz), 1.80(2H, m), 2.80(2H, q, J=7.6 Hz), 3.65(3H, s), 3.80(4H, m), 3.79(2H, t, J=4.6 Hz), 4.24(4H, brs), 4.32(2H, s), 6.68-6.81(3H, m).

2-(3-amino-4-ethoxybenzylsulfanyl)-9-methyl-6-morpholino-9H-purine (Compound 114)

$^1$H-NMR (CDCl$_3$) δ: 1.41(3H, t, J=7.3 Hz), 3.76(3H, s), 3.79(4H, m), 4.12(2H, q, J=7.3 Hz), 4.26(4H, brs), 4.33(2H, s), 6.67(1H, d, J=8.1 Hz), 6.75(1H, dd, J=2.1, 8.1 Hz), 6.82 (1H, d, J=2.1 Hz), 7.58(1H, s).

8,9-diethyl-2-(3-iodo-4-methoxybenzylsulfanyl)-6-morpholino-9H-purine (Compound 115)

$^1$H-NMR (CDCl$_3$) δ: 1.38(6H, m), 2.80(2H, q, J=7.6 Hz), 3.80(4H, m), 3.84(3H, s), 4.12(2H, q, J=7.3 Hz), 4.25(4H, brs), 4.30(2H, s), 6.73(1H, d, J=8.4 Hz), 7.40(1H, dd, J=2.3, 8.4 Hz), 7.89(1H, d, J=2.3 Hz).

2-(4-ethoxy-3-fluorobenzylsulfanyl)-8-ethyl-9-methyl-6-morpholino-9H-purine (Compound 116)

$^1$H-NMR (CDCl$_3$) δ: 1.13(3H, t, J=7.6 Hz), 1.45(3H, t, J=7.1 Hz), 2.78(2H, q, J=7.6 Hz), 3.66(3H, s), 3.79(4H, m), 4.07(2H, q, J=7.1 Hz), 4.25(4H, brs), 4.34(2H, s), 6.86(1H, m), 7.09(1H, m), 7.17(1H, m).

8,9-diethyl-2-(4-ethoxy-3-fluorobenzylsulfanyl)-6-morpholino-9H-purine (Compound 117)

$^1$H-NMR (CDCl$_3$) δ: 1.39(9H, m), 2.79(2H, q, J=7.6 Hz), 3.78(4H, m), 4.07(2H, q, J=6.9 Hz), 4.13(2H, q, J=7.3 Hz), 4.25(4H, brs), 4.33(2H, s), 6.86(1H, m), 7.20(1H, m), 7.28(1H, m).

2-(3-amino-4-methoxybenzylsulfanyl)-6-(2-ethoxymorpholino)-9-ethyl-9H-purine (Compound 119)

$^1$H-NMR (CDCl$_3$) δ: 1.22(3H, t, J=7.1 Hz), 1.47(3H, t, J=7.4 Hz), 3.74-3.80(2H, m), 3.82(3H, s), 3.85-3.91(2H, m), 4.05-4.19(2H, m), 4.11(2H, q, J=7.1 Hz), 4.19(2H, q, J=7.4 Hz), 4.32(2H, s), 4.65-4.75(1H, m), 6.68(1H, d. J=7.8 Hz), 6.77-6.82(2H, m), 7.62(1H, s).

2-(3-amino-4-methoxybenzylsulfanyl)-6-(2-ethoxymorpholino)-9-methyl-9H-purine (Compound 120)

$^1$H-NMR (CDCl$_3$) δ: 1.22(3H, t, J=7.0 Hz), 3.56-4.33 (18H, m), 4.73(1H, dd, J=5.1, 5.7 Hz), 6.83-6.67(3H, m), 7.59(1H, s).

2-(4-methoxybenzylsulfanyl)-9-methyl-6-(pyrazol-1-yl)-9H-purine (Compound 121)

$^1$H-NMR (CDCl$_3$) δ: 3.77(3H, s), 3.87(3H, s), 4.49(2H, s), 6.54(1H, dd, J=1.0, 2.6 Hz), 6.85(2H, d, J=8.7 Hz), 7.42(2H, d, J=8.7 Hz), 7.99(2H, m), 8.84(1H, d, J=2.6 Hz).

2-(3-amino-4-ethoxybenzylsulfanyl)-9-ethyl-8-methyl-6-morpholino-9H-purine (Compound 122)

$^1$H-NMR (CDCl$_3$) δ: 1.36(3H, t, J=6.9 Hz), 1.40(3H, t, J=7.1 Hz), 2.51(3H, s), 3.78(4H, m), 4.02(2H, q, J=6.9 Hz), 4.14(2H, q, J=7.1 Hz), 4.23(4H, brs), 4.31(2H, s), 6.65-6.82 (3H, m).

8,9-diethyl-2-(3-fluoro-4-methoxybenzylsulfanyl)-6-morpholino-9H-purine (Compound 123)

$^1$H-NMR (CDCl$_3$) δ: 1.38(6H, m), 2.80(2H, q, J=7.6 Hz), 3.78(4H, m), 3.85(3H, s), 4.13(2H, q, J=7.1 Hz), 4.25(4H, brs), 4.33(2H, s), 6.85-7.25(3H, m).

2-(4-methoxybenzylsulfanyl)-9-methyl-6-(1,2,4-triazol-1-yl)-9H-purine (Compound 124)

$^1$H-NMR (CDCl$_3$) δ: 3.78(3H, s), 3.90(3H, s), 4.48(2H, s), 6.84(2H, d, J=8.7 Hz), 7.42(2H, d, J=8.7 Hz), 8.02(1H, s), 8.28(1H, s), 9.50(1H, s).

2-(3-amino-4-methoxybenzylsulfanyl)-9-ethyl-6-methylamino-9H-purine (Compound 125)

$^1$H-NMR (CDCl$_3$) δ: 1.50(3H, t, J=7.4 Hz), 3.19(3H, brs), 3.82(3H, s), 4.18(2H, q, J=7.4 Hz), 4.36(2H, s), 5.59(1H, brs), 6.69(1H, d, J=8.1 Hz), 6.79-6.84(2H, m), 7.61(1H, s).

6-allylamino-2-(4-methoxybenzylsulfanyl)-9-methyl-9H-purine (Compound 126)

$^1$H-NMR (CDCl$_3$) δ: 3.76(3H, s), 3.78(3H, s), 4.30(2H, brs), 4.41(2H, s), 5.17(1H, dd, J=2.8, 10.2 Hz), 5.28(1H, dd, J=2.8, 17.1 Hz), 5.83(1H, brs), 5.90-6.04(1H, m), 6.82(2H, d, J=8.6 Hz), 7.37(2H, d, J=8.6 Hz), 7.59(1H, s).

6-(N,N-diallylamino)-2-(4-methoxybenzylsulfanyl)-9-methyl-9H-purine (Compound 127)

$^1$H-NMR (CDCl$_3$) δ: 3.74(3H, s), 3.78(3H, s), 4.05-5.13 (6H, m), 5.15(2H, dd, J=1.4, 1.6 Hz), 5.20(2H, d, J=4.9 Hz), 5.83-5.96(2H, m), 6.82(2H, d, J=8.6 Hz), 7.36(2H, d, J=8.6 Hz), 7.58(1H, s).

2-(4-methoxybenzylsulfanyl)-9-methyl-6-(3-methylpyrrol-1-yl)-9H-purine (Compound 128)

$^1$H-NMR (CDCl$_3$) δ: 2.17(3H, s), 3.78(3H, s), 3.84(3H, s), 4.48(2H, s), 6.24(1H, dd, J=0.8, 2.6 Hz), 6.84(2H, d, J=8.9 Hz), 7.40(2H, d, J=8.9 Hz), 7.86(1H, s), 8.02(1H, d, J=0.8 Hz), 8.16 (1H, d, J=2.6 Hz).

6-(2-methoxymorpholino)-2-(4-methoxy-3-nitrobenzylsulfanyl)-9-methyl-9H-purine (Compound 129)

$^1$H-NMR (CDCl$_3$) δ: 3.41(3H, s), 3.26-4.06(11H, m), 4.35 (2H, s), 4.67-4.71(2H, m), 7.01(1H, d, J=8.6 Hz), 7.60(1H, s), 7.65(1H, dd, J=2.3, 8.6 Hz), 8.05(1H, d, J=2.3 Hz).

2-(4-methoxybenzylsulfanyl)-9-methyl-6-(3-pyrrolin-1-yl)-9H-purine (Compound 130)

$^1$H-NMR (CDCl$_3$) δ: 3.76(3H, s), 3.78(3H, s), 4.44(2H, s), 4.53(2H, brs), 4.89(2H, brs), 5.96(2H, brd, J=3.2 Hz), 6.82 (2H, d, J=8.6 Hz), 7.39(2H, d, J=8.6 Hz), 7.59(1H, s).

6-(2-hydroxymorpholino)-2-(4-methoxy-3-nitrobenzylsulfanyl)-9-methyl-9H-purine (Compound 131)

$^1$H-NMR (CDCl$_3$) δ: 3.60-3.75(2H, m), 3.76(3H, s), 3.92 (3H, s), 4.10-4.20(2H, m), 4.30(2H, brs), 4.35(2H, s), 5.10 (1H, t, J=3.5 Hz), 7.01(1H, d, J=8.7 Hz), 7.61(1H, s), 7.64 (1H, dd, J=2.3, 8.7 Hz), 8.06(1H, d, J=2.3 Hz).

2-(4-methoxybenzylsulfanyl)-9-methyl-6-morpholino-8-(1-propenyl)-9H-purine (Compound 132)

$^1$H-NMR (CDCl$_3$) δ: 1.99(3H, dd, J=1.8, 6.8 Hz), 3.71(3H, s), 3.78(3H, s), 3.80(4H, m), 4.27(4H, brs), 4.38(2H, s), 6.39 (1H, dd, J=1.8, 13.7 Hz), 6.81(2H, d, J=8.4 Hz), 6.89(1H, dd, J=6.8, 13.7 Hz), 7.36(2H, d, J=8.4 Hz).

6-(2-ethoxymorpholino)-2-(3-fluoro-4-methoxybenzylsulfanyl)-9-methyl-9H-purine (Compound 133)

$^1$H-NMR (CDCl$_3$) δ: 1.21(3H, t, J=7.0 Hz), 3.50-4.35 (16H, m), 4.72(1H, t, J=3.5 Hz), 6.87(1H, dd, J=8.1 8.6 Hz), 7.13-7.17(1H, m), 7.22(1H, dd, J=2.2, 12.2 Hz), 7.60(1H, s).

2-(3-cyano-4-methoxybenzylsulfanyl)-6-(2-ethoxymorpholino)-9-methyl-9H-purine (Compound 134)

$^1$H-NMR (CDCl$_3$) δ: 1.21(3H, t, J=7.1 Hz), 3.50-3.85(2H, m), 3.76(3H, s), 3.89(3H, s), 4.10(1H, m), 4.28(4H, brs), 4.33(2H, s), 4.74(1H, m), 6.89(1H, d, J=8.6 Hz), 7.60(1H, s), 7.60-7.76(2H, m).

6-(2-ethoxymorpholino)-9-ethyl-2-(3-fluoro-4-methoxybenzylsulfanyl)-9H-purine (Compound 135)

$^1$H-NMR (CDCl$_3$) δ: 1.21(3H, t, J=6.9 Hz), 1.47(3H, t, J=7.2 Hz), 3.53-3.59(1H, m), 3.65-3.70(1H, m), 3.85(3H, s), 4.10-4.13(2H, m), 4.16(2H, q, J=6.9 Hz), 4.19(2H, q, J=7.2 Hz), 4.32-4.34(2H, m), 4.36(2H, s), 4.70-4.73(1H, m), 6.86 (1H, t, J=8.6 Hz), 7.12-7.27(2H, m), 7.63(1H, s).

2-(3-amino-4-methoxybenzylsulfanyl)-6-dimethylamino-9-ethyl-9H-purine (Compound 136)

$^1$H-NMR (CDCl$_3$) δ: 1.47(3H, t, J=7.2 Hz), 3.50(6H, brs), 3.81(3H, s), 4.16(2H, q, J=7.2 Hz), 4.35(2H, s), 6.68(1H, d. J=8.0 Hz), 6.77-6.90(2H, m), 7.61(1H, s).

2-(3-fluoro-4-methoxybenzylsulfanyl)-6-(N-methoxy-N-methylamino)-9-methyl-9H-purine (Compound 137)

$^1$H-NMR (CDCl$_3$) δ: 3.54(3H, s), 3.80(3H, s), 3.86(3H, s), 3.92(3H, s), 4.36(2H, s), 6.87(1H, t, J=8.6 Hz), 7.13-7.16(1H, m), 7.19-7.24(1H, m), 7.99(1H, s).

6-(2-ethoxymorpholino)-2-(4-ethoxy-3-nitrobenzylsulfanyl)-9-ethyl-9H-purine (Compound 138)

$^1$H-NMR (CDCl$_3$) δ: 1.21(3H, t, J=7.3 Hz), 1.45(3H, t, J=7.0 Hz), 1.48(3H, t, J=7.3 Hz), 3.50-3.86(3H, m), 4.07-

4.35(11H, m), 4.72(1H, t, J=3.8 Hz), 6.98(1H, d, J=8.6 Hz), 7.61(2H, d, J=8.6 Hz), 7.98(1H, d, J=2.4 Hz).

2-(4-methoxy-3-nitrobenzylsulfanyl)-9-methyl-6-(1-pyrrolyl)-9H-purine (Compound 139)

$^1$H-NMR (CDCl$_3$) δ: 3.88(3H, s), 3.93(3H, s), 4.45(2H, s), 6.40(2H, t, J=2.3 Hz), 7.03(1H, d, J=8.6 Hz), 7.69(1H, dd, J=2.3, 8.6 Hz), 7.87(1H, s), 8.10(1H, d, J=2.4 Hz), 8.24(2H, t, J=2.3 Hz).

2-(3-amino-4-ethoxybenzylsulfanyl)-6-dimethylamino-9-methyl-9H-purine (Compound 140)

$^1$H-NMR (CDCl$_3$) δ: 1.41(3H, t, J=6.9 Hz), 3.49(6H, brs), 3.73(3H, s), 3.80(2H. Brs), 4.02(2H, q. J=6.9 Hz), 4.36(2H, s), 6.67(1H, d. J=8.2 Hz), 6.75-6.83(2H, m), 7.56(1H, s).

2-(3-amino-4-methoxybenzylsulfanyl)-9-methyl-6-(1-pyrrolyl)-9H-purine (Compound 141)

$^1$H-NMR (CDCl$_3$) δ: 3.82(3H, s), 3.87(3H, s), 4.49(2H, s), 6.40(2H, t, J=2.3 Hz), 6.72(1H, d, J=8.4 Hz), 6.85(1H, d, J=2.3 Hz), 7.04(1H, dd, J=2.3, 8.4 Hz), 7.85(1H, s), 8.29(2H, t, J=2.3 Hz).

2-(4-methoxy-3-nitrobenzylsulfanyl)-9-methyl-6-(3-pyrrolin-1-yl)-9H-purine (Compound 142)

$^1$H-NMR (CDCl$_3$) δ: 3.78(3H, s), 3.93(3H, s), 4.40(2H, s), 4.50(2H, brs), 4.88(2H, brs), 5.96(2H, d, J=2.7 Hz), 7.01(1H, d, J=8.6 Hz), 7.60(1H, s), 7.67(1H, dd, J=2.2, 8.6 Hz), 8.07(1H, d, J=2.2 Hz).

6-(N-methoxy-N-methylamino)-2-(4-methoxy-3-nitrobenzylsulfanyl)-9-methyl-9H-purine (Compound 143)

$^1$H-NMR (CDCl$_3$) δ: 3.52(3H, s), 3.76(3H, s), 3.92(3H, s), 3.93(3H, s), 4.37(2H, s), 7.01(1H, t, J=8.7 Hz), 7.66(1H, dd, J=2.3, 8.7 Hz), 7.70(1H, s), 8.05(1H, d, J=2.3 Hz).

2-(3-amino-4-methoxybenzylsulfanyl)-9-methyl-6-(3-pyrrolin-1-yl)-9H-purine (Compound 144)

$^1$H-NMR (CDCl$_3$) δ: 3.74(3H, s), 3.82(3H, s), 4.38(2H, s), 4.43-4.87(6H, m), 5.95(2H, d, J=2.7 Hz), 6.69(1H, d, J=8.1 Hz), 6.80(2H, m), 7.57(1H, s).

2-(3-amino-4-methoxybenzylsulfanyl)-6-(N-methoxy-N-methylamino)-9-methyl-9H-purine (Compound 145)

$^1$H-NMR (CDCl$_3$) δ: 3.56(3H, s), 3.77(3H, s), 3.82(3H, s), 3.93(3H, s), 4.36(2H, s), 6.71(1H, t, J=8.4 Hz), 6.81-6.86(2H, m), 7.67(1H, s).

2-[2-(6-methoxynaphthalen-2-yl)-2-oxoethylsulfanyl]-8-ethyl-9-methyl-6-morpholino-9H-purine (Compound 146)

$^1$H-NMR (CDCl$_3$) δ: 1.32(3H, t, J=7.3 Hz), 2.70(2H, q, J=7.3 Hz), 3.45(3H, s), 3.63(4H, t, J=4.7 Hz), 3.96(3H, s), 4.12, (4H, brs), 4.67(2H, s), 7.12-7.20(2H, m), 7.80-7.86(2H, m), 8.08-8.11(2H, m), 8.59(2H, d, J=3.7 Hz).

Example 5

Synthesis of 2-(3-amino-4-methoxybenzylsulfanyl)-6-(2,3,-dihydro-[1,4]oxadin-4-yl)-9-methyl-9H-purine (Compound 150)

[Chem. 17]

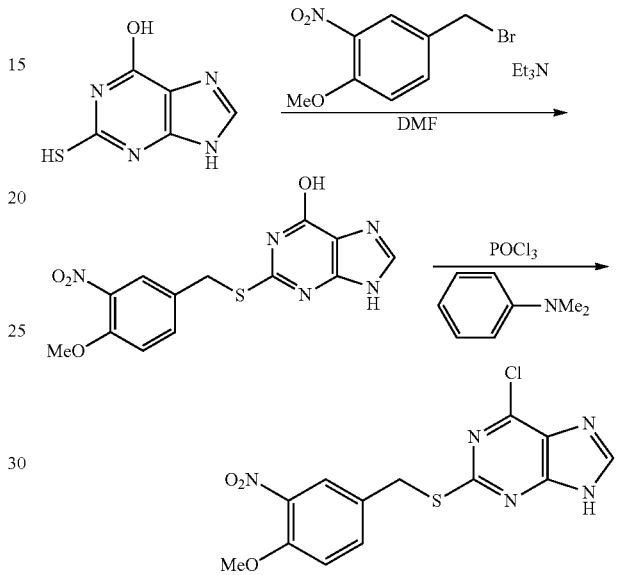

(5-1) Synthesis of 6-hydroxy-2-(4-methoxy-3-nitrobenzylsulfanyl)-9H-purine

A DMF (100 ml) solution of 2-thioxanthine (7.75 g, 46 mmol), triethylamine (8.0 ml, 60 mmol), 4-methoxy-3-nitrobenzyl bromide (12.48 g, 51 mmol) was heated and stirred at 100° C. for 3 hours. Water was added to the reaction solution, the precipitated crystals were collected by filtration and washed sequentially with water and ether to obtain 14.67 g (95% yield) of 6-hydroxy-2-(4-methoxy-3-nitrobenzylsulfanyl)-9H-purine.

$^1$H-NMR (DMSO-d$_6$) δ: 3.89(3H, s), 4.45(2H, s), 7.32(1H, d, J=8.6 Hz), 7.76(1H, dd, J=2.1, 8.6 Hz), 7.99(1H, d, J=2.1 Hz), 8.01(2H, brs), 12.5(1H, brs).

(5-2) Synthesis of 6-chloro-2-(4-methoxy-3-nitrobenzylsulfanyl)-9H-purine 6-hydroxy-2-(4-methoxy-3-nitrobenzylsulfanyl)-9H-purine (14.67 g, 44 mmol) was suspended in dioxane (30 ml), phosphorus oxychloride (12.3 ml, 132 mmol) and dimethylaniline (8.3 ml, 66 mmol) were added and heated and stirred at 100° C. for 2 hours. The reaction solution was poured into ice water and extracted twice with ethyl acetate. After combining the ethyl acetate layers and washing with a saturated saline solution, it was dried with MgSO$_4$ and the solvent was distilled away under reduced pressure. Separation and purification were performed by silica gel column chromatography (dichloromethane: methanol=20:1) to obtain 5.45 g (35% yield) of 6-chloro-2-(4-methoxy-3-nitrobenzylsulfanyl)-9H-purine.

¹H-NMR (DMSO-d₆) δ: 3.89(3H, s), 4.46(2H, s), 7.31(1H, d, J=8.7 Hz), 7.78(1H, dd, J=2.3, 8.7 Hz), 8.01(1H, d, J=2.3 Hz), 8.55(1H, s), 13.80(1H, brs).

[Chem. 18]

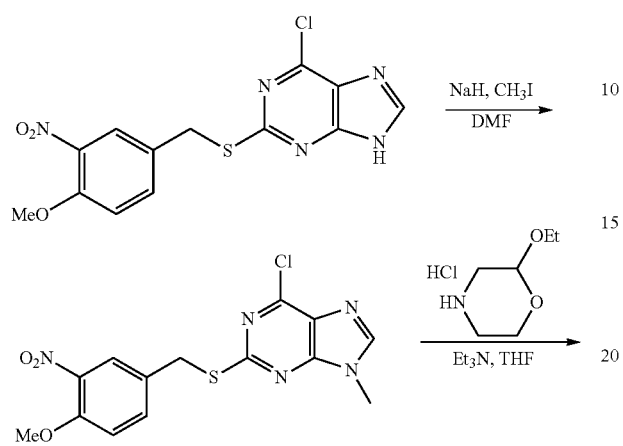

(5-3) Synthesis of 6-chloro-2-(4-methoxy-3-nitrobenzylsulfanyl)-9-methyl-9H-purine 6-chloro-2-(4-methoxy-3-nitrobenzylsulfanyl)-9H-purine (2.00 g, 6.3 mmol) was dissolved in N,N-dimethylformamide (20 ml), under ice cooling, 60% sodium hydride (0.30 g, 7.6 mmol) was added and stirred for 5 minutes, then methyl iodide (1.08 g, 0.76 mmol) was added and stirred overnight. Water was added to the reaction solution, the precipitated crystals were collected by filtration and washed sequentially with water and ether to obtain 2.06 g (89% yield) of 6-chloro-2-(4-methoxy-3-nitrobenzylsulfanyl)-9-methyl-9H-purine.

¹H-NMR (CDCl₃) δ: 3.89(3H, s), 3.95(3H, s), 4.39(2H, s), 7.03(1H, d, J=8.6 Hz), 7.69(1H, dd, J=2.3, 8.6 Hz), 7.94(1H, s), 8.10(1H, d, J=2.3 Hz).

(5-4) Synthesis of 6-(2-ethoxymorpholino)-2-(4-methoxy-3-nitrobenzylsulfanyl)-9-methyl-9H-purine (Compound 118)

6-chloro-2-(4-methoxy-3-nitrobenzylsulfanyl)-9-methyl-9H-purine (850 mg, 2.32 mmol) was dissolved in tetrahydrofuran (100 ml), triethylamine (1.57 g, 15.51 mmol) and 2-ethoxymorpholine hydrochloride (520 mg, 3.10 mmol) were added and heated to reflux for 7 hours. After distilling away the solvent under reduced pressure, water was added to the residue and extracted twice with ethyl acetate, then the organic layers were washed with a saturated saline solution and dried with MgSO₄. After distilling away the solvent under reduced pressure, purification was performed by silica gel column chromatography (ethyl acetate:hexane=1:3) to obtain 738 mg (69% yield) of 6-(2-ethoxymorpholino)-2-(4-methoxy-3-nitrobenzylsulfanyl)-9-methyl-9H-purine.

¹H-NMR (CDCl₃) δ: 1.22(3H, t, J=3.5 Hz), 4.73(1H, t, J=3.8 Hz), 3.26-4.35(16H, m), 7.01(1H, d, J=8.4 Hz), 7.65 (2H, dd, J=2.4, 8.4 Hz), 8.05(1H, d, J=2.4 Hz).

[Chem. 19]

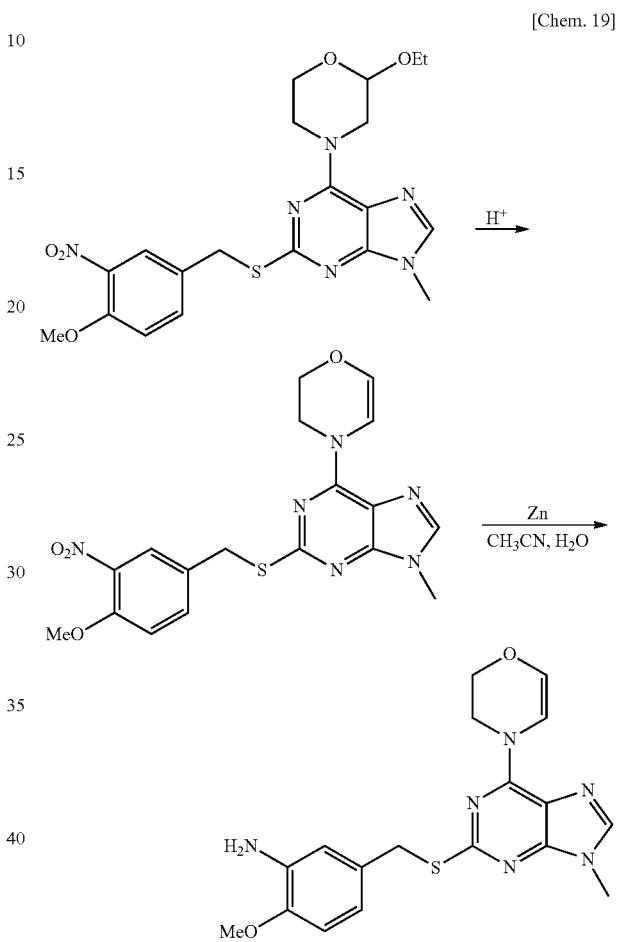

(5-5) Synthesis of 6-(2,3-dihydro-[1,4]oxadin-4-yl)-2-(4-methoxy-3-nitrobenzylsulfanyl)-9-methyl-9H-purine (Compound 149)

4N—HCl/dioxane (2 ml) was added to 6-(2-ethoxymorpholino)-2-(4-methoxy-3-nitrobenzylsulfanyl)-9-methyl-9H-purine (30 mg, 65.1 µmol) under ice cooling, and heated to reflux for 2 hours. The solvent was distilled away under reduced pressure, and dichloromethane and water were added to the residue. Neutralization was done using a saturated sodium carbonate solution and extraction was performed with dichloromethane. After drying the organic layer with magnesium sulfate and distilling away the solvent under reduced pressure, the residue was subjected to silica gel column chromatography (hexane:ethyl acetate=1:4) to obtain 6-(3,4-dihydro-2H-[1,4]oxadin-4-yl)-2-(4-methoxy-3-nitrobenzylsulfanyl)-9-methyl-9H-purine (15 mg, 56%).

¹H-NMR (CDCl₃) δ: 3.64-4.36(11H, m), 4.37(2H, s), 6.15 (1H, d, J=5.1 Hz), 7.01(1H, d, J=8.6 Hz), 7.05(2H, dd, J=2.4, 8.6 Hz), 8.07(1H, d, J=2.4 Hz).

(5-6) Synthesis of 2-(3-amino-4-methoxybenzylsulfanyl)-6-(2,3,-dihydro-[1,4]oxadin-4-yl)-9-methyl-9H-purine (Compound 150)

A mixture of 6-(3,4-dihydro-2H-[1,4]oxadin-4-yl)-2-(4-methoxy-3-nitrobenzylsulfanyl)-9-methyl-9H-purine (25 mg, 60.3 μmol), zinc dust (90 mg, 1.38 mmol), calcium chloride (4 mg, 36.0 μmol), acetonitrile (1 ml) and water (0.3 ml) was heated to reflux for 2 hours. The insolubles were filtered off, the filtrate was distilled away under reduced pressure, dichloromethane and water were added to the residue and extracted with dichloromethane. The organic layer was dried with magnesium sulfate, and the filtrate was distilled away under reduced pressure. Chloroform and ethyl acetate were added to the residue to dissolve it, hexane was added, and the precipitated crystals were collected by filtration to obtain 2-(3-amino-4-methoxybenzylsulfanyl)-6-(3,4,-dihydro-2H-[1,4]oxadin-4-yl)-9-methyl-9H-purine (12.7 mg, 55%).

$^1$H-NMR (CDCl$_3$) δ: 3.60-4.35(14H, m), 6.15(1H, d, J=5.1 Hz), 6.68-6.87(4H, m), 7.64(1H, d, J=4.1 Hz).

The following compounds were synthesized according to the above methods of Examples 1 to 5.

6-(2,3-dihydro-[1,4]oxadin-4-yl)-2-(4-methoxybenzylsulfanyl)-9-methyl-9H-purine (Compound 147)

$^1$H-NMR (CDCl$_3$) δ: 3.64-4.22(10H, m), 4.41(2H, s), 6.15(1H, d, J=5.4 Hz), 6.81-6.86(3H, m), 7.37(2H, d, J=8.6 Hz), 7.64(1H, s).

6-(2,3-dihydro-[1,4]oxadin-4-yl)-8-ethyl-2-(4-methoxybenzylsulfanyl)-9-methyl-9H-purine (Compound 148)

$^1$H-NMR (CDCl$_3$) δ: 1.39(3H, t, J=7.5 Hz), 2.82(2H, q, J=7.5 Hz), 3.69(3H, s), 3.78(3H, s), 4.20-4.50(2H, brs), 4.22(2H, brd, J=2.8 Hz), 4.40(2H, s), 6.13(1H, d, J=5.1 Hz), 6.83(2H, d, J=8.7H), 7.37(2H, d, J=8.7 Hz), 7.90(1H, brs).

2-(3-amino-4-methoxybenzylsulfanyl)-6-(2,3-dihydro-[1,4]oxadin-4-yl)-9-ethyl-9H-purine (Compound 151)

$^1$H-NMR (CDCl$_3$) δ: 1.47(3H, t, J=7.2 Hz), 3.76(2H, brs), 3.82(3H, s), 4.13-4.23(4H, m), 4.34(2H, s), 6.14(1H, d, J=5.0 Hz), 6.68(1H, d, J=8.1 Hz), 6.77-6.82(2H, m), 7.67(1H, s), 7.89 (1H, brs).

6-(2,3-dihydro-[1,4]oxadin-4-yl)-2-(3-fluoro-4-methoxybenzylsulfanyl)-9-methyl-9H-purine (Compound 152)

$^1$H-NMR (CDCl$_3$) δ: 3.87-4.75(12H, m), 6.33(1H, d, J=5.1 Hz), 6.86-6.92(1H, m), 7.11-7.19(2H, m), 7.69(1H, brs), 8.09 (1H, brs).

2-(3-cyano-4-methoxybenzylsulfanyl)-6-(2,3-dihydro-[1,4]oxadin-4-yl)-9-methyl-9H-purine (Compound 153)

$^1$H-NMR (CDCl$_3$) δ: 3.78(3H, s), 3.89(3H, s), 4.20(2H, brs), 4.22(2H, m), 4.35(2H, s), 6.15(1H, d, J=4.9 Hz), 6.89 (1H, d, J=8.7 Hz), 7.64(1H, dd, J=2.3, 8.7 Hz), 7.65(1H, s), 7.70(1H, d, J=2.3 Hz), 7.90(1H, brs).

6-(2,3-dihydro-[1,4]oxadin-4-yl)-9-ethyl-2-(3-fluoro-4-methoxybenzylsulfanyl)-9H-purine (Compound 154)

$^1$H-NMR (CDCl$_3$) δ: 1.49(3H, t, J=7.3 Hz), 3.86(3H, s), 4.15-4.24(4H, m), 4.22(2H, q, J=7.3 Hz), 4.35(2H, s), 6.15(1H, d, J=5.1 Hz), 6.87(1H, t, J=8.4 Hz), 7.13-7.24(2H, m), 7.67(1H, s), 7.80(1H, brs).

6-(2,3-dihydro-[1,4]oxadin-4-yl)-9-ethyl-2-(3-nitro-4-ethoxybenzylsulfanyl)-9H-purine (Compound 155)

$^1$H-NMR (CDCl$_3$) δ: 1.46(3H, t, J=6.8 Hz), 1.59(3H, t, J=7.0 Hz), 4.12-4.43(10H, m), 6.28(1H, d, J=5.1 Hz), 7.01 (2H, d, J=8.6 Hz), 7.61(1H, d, J=8.6 Hz), 7.96(1H, d, J=2.4 Hz), 8.11(1H, brs).

2-(3-amino-4-ethoxybenzylsulfanyl)-6-(2,3-dihydro-[1,4]oxadin-4-yl)-9-ethyl-9H-purine (Compound 156)

$^1$H-NMR (CDCl$_3$) δ: 1.41(3H, t, J=7.3 Hz), 1.49(3H, t, J=7.3 Hz), 3.61-4.30(10H, m), 4.34(2H, s), 6.15(1H, d, J=5.1 Hz), 6.68(1H, d, J=8.1 Hz), 6.77(1H, dd, J=2.2, 8.1 Hz), 6.82(1H, d, J=2.2 Hz), 7.67(1H, s), 7.88(1H, brs).

6-(2,3-dihydro[1,4]oxadin-4-yl)-8-ethyl-2-(3-fluoro-4-methoxybenzylsulfanyl)-9-methyl-9H-purine (Compound 157)

$^1$H-NMR (CDCl$_3$) δ: 1.38(3H, t, J=7.6 Hz), 2.82(2H, q, J=7.6 Hz), 3.67(3H, s), 3.86(3H, s), 4.15-4.33(4H, m), 4.36 (2H, s), 6.13(1H, d, J=5.1 Hz), 6.86(1H, t, J=8.6H), 7.13-7.24 (2H, m), 7.77(1H, brs).

8,9-diethyl-6-(2,3-dihydro-[1,4]oxadin-4-yl)-2-(4-methoxybenzylsulfanyl)-9H-purine (Compound 158)

$^1$H-NMR (CDCl$_3$) δ: 1.37(3H, t, J=7.6 Hz), 1.38(3H, t, J=7.3 Hz), 2.81(2H, q, J=7.6 Hz), 3.78(3H, s), 4.15(2H, q, J=7.3 Hz), 4.20(2H, m), 4.30(2H, brs), 4.39(2H, s), 6.13(1H, d, J=5.1 Hz), 6.82(2H, d, J=8.7 Hz), 7.38(2H, d, J=8.7 Hz), 7.88(1H, brs).

6-(2,3-dihydro-[1,4]oxadin-4-yl)-2-(4-ethoxy-3-nitrobenzylsulfanyl)-9-methyl-9H-purine (Compound 159)

$^1$H-NMR (CDCl$_3$) δ: 1.44(3H, t, J=6.9 Hz), 3.79(3H, s), 4.14(2H, q, J=6.9 Hz), 4.20-4.23(2H, m), 4.36(2H, s), 4.75 (2H, brs), 6.15(1H, d, J=5.0 Hz), 6.98(1H, d, J=8.7 Hz), 7.61(1H, dd, J=2.1, 8.7 Hz), 7.64(1H, s), 7.88(1H, brs), 8.03 (1H, d, J=2.1 Hz).

2-(3-amino-4-ethoxybenzylsulfanyl)-6-(2,3-dihydro-[1,4]oxadin-4-yl)-9-methyl-9H-purine (Compound 160)

$^1$H-NMR (CDCl$_3$) δ: 1.41(3H, t, J=6.9 Hz), 3.67(3H, s), 3.99(2H, brs), 4.02(2H, q, J=6.9 Hz), 4.20-4.25(2H, m), 4.34 (2H, s), 4.75(2H, brs), 6.15(1H, d, J=4.9 Hz), 6.68(1H, d, J=8.2 Hz), 6.77(1H, dd, J=2.1, 8.2 Hz), 6.82(1H, d, J=2.1 Hz), 7.62(1H, s), 7.87(1H, brs).

2-(3-cyano-4-methoxybenzylsulfanyl)-6-(2,3-dihydro-[1,4]oxadin-4-yl)-8-ethyl-9-methyl-9H-purine (Compound 161)

$^1$H-NMR (CDCl$_3$) δ: 1.39(3H, t, J=7.6 Hz), 2.82(2H, q, J=7.6 Hz), 3.68(3H, s), 3.89(3H, s), 4.13-4.22(4H, m), 4.34

(2H, s), 6.14(1H, d, J=5.1 Hz), 6.88(1H, d, J=8.6 Hz), 7.62 (1H, dd. J=2.1 Hz, 8.6 Hz), 7.69(1H, d, J=2.1 Hz), 7.95(1H, brs).

2-(3-amino-4-methoxybenzylsulfanyl)-6-(2,3-dihydro-[1,4]oxadin-4-yl)-8-ethyl-9-methyl-9H-purine (Compound 162)

¹H-NMR (CDCl₃) δ: 1.38(3H, t, J=7.6 Hz), 2.81(2H, q, J=7.6 Hz), 3.66(3H, s), 3.82(3H, s), 4.16-4.21(4H, m), 4.34 (2H, s), 6.13(1H, d, J=5.1 Hz), 6.68(1H, d, J=8.1 Hz), 6.78 (1H, dd. J=2.0 Hz, 8.1 Hz), 6.82(1H, d, J=2.0 Hz), 7.91(1H, brs).

Example 6

Synthesis of 2-(4-methoxy-3-nitrobenzylsulfanyl)-9-methyl-6-(1-trans-propenyl)-9H-purine (Compound 171)

[Chem. 20]

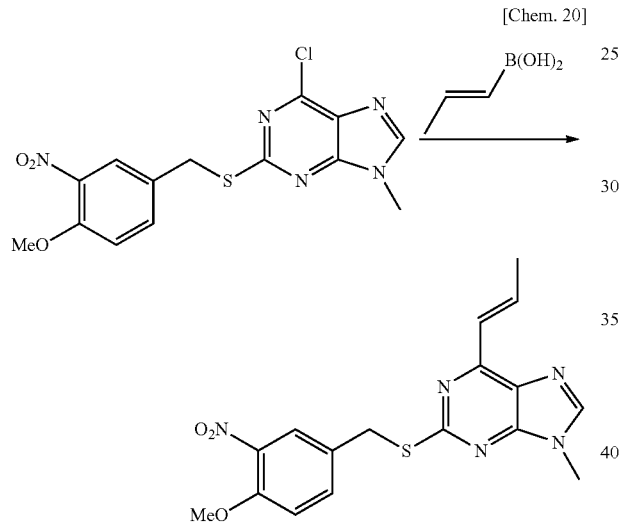

6-chloro-2-(4-methoxy-3-nitrobenzylsulfanyl)-9-methyl-9H-purine (100 mg, 0.273 mmol) was dissolved in dimethoxyethane (4 ml), then trans-propenylboronic acid (70 mg, 0.815 mmol) and tetrakis(triphenylphosphine)palladium (0) (30 mg, 0.025 mmol) were added. Then 106 mg (1.0 mmol) of sodium carbonate dissolved in water (2 ml) was added, and the mixture was heated to reflux for 2 hours. After cooling it, the insolubles were filtered off with Celite, the filtrate was distilled away under reduced pressure, ethyl acetate (20 ml) and water (20 ml) were added to the residue and extraction was performed. After washing with water, drying was carried out with anhydrous magnesium sulfate, the insolubles were filtered off, the filtrate was distilled away under reduced pressure, and the residue was subjected to silica gel column chromatography (ethyl acetate: methanol=50:1) to obtain 2-(4-methoxy-3-nitrobenzylsulfanyl)-9-methyl-6-(1-trans-propenyl)-9H-purine (87.5 mg, 86%).

¹H-NMR (CDCl₃) δ: 2.05(3H, dd, J=1.8, 8.6 Hz), 3.85(3H, s), 3.93(3H, s), 4.41(2H, s), 6.92(1H, m), 7.03(1H, d, J=8.6 Hz), 7.58(1H, m), 7.69(1H, dd, J=2.5, 8.6 Hz), 7.86(1H, s), 8.11(1H, d, J=2.5 Hz).

The following compounds were synthesized according to the above methods of Examples 1 to 6.

2-(4-methoxybenzylsulfanyl)-9-methyl-6-(1-trans-propenyl)-9H-purine (Compound 163)

¹H-NMR (CDCl₃) δ: 2.05(3H, dd, J=1.8, 6.9 Hz), 3.78(3H, s), 3.81(3H, s), 4.47(2H, s), 6.83(2H, d, J=8.7 Hz), 6.90(1H, m), 7.41(2H, d, J=8.7 Hz), 7.50(1H, m), 7.85(1H, s).

2-(4-methoxybenzylsulfanyl)-9-methyl-6-propyl-9H-purine (Compound 164)

¹H-NMR (CDCl₃) δ: 1.01(3H, t, J=7.4 Hz), 1.87-1.91(2H, m), 3.09(2H, t, J=7.4 Hz), 3.78(3H, s), 3.85(3H, s), 4.45(2H, s), 6.83(2H, d, J=8.7 Hz), 7.42(2H, d, J=8.7 Hz), 7.84(1H, s).

2-(4-methoxybenzylsulfanyl)-9-methyl-6-vinyl-9H-purine (Compound 165)

¹H-NMR (CDCl₃) δ: 3.78(3H, s), 3.83(3H, s), 4.47(2H, s), 5.93(1H, dd, J=2.0, 10.7 Hz), 6.83(2H, d, J=8.7 Hz), 7.01(1H, dd, J=2.0, 17.5 Hz), 7.22(1H, dd, J=10.7, 17.5 Hz), 7.48(2H, d, J=8.7 Hz), 7.88(1H, s).

2-(4-methoxybenzylsulfanyl)-9-methyl-6-(4-nitrophenyl)-9H-purine (Compound 166)

¹H-NMR (CDCl₃) δ: 3.79(3H, s), 3.91(3H, s), 4.54(2H, s), 6.85(2H, d, J=9.2 Hz), 7.43(2H, d, J=9.2 Hz), 8.02(1H, s), 8.37(2H, d, J=9.1 Hz), 8.99(2H, d, J=9.1 Hz).

6-(2-furyl)-2-(4-methoxybenzylsulfanyl)-9-methyl-9H-purine (Compound 167)

¹H-NMR (CDCl₃) δ: 3.78(3H, s), 3.86(3H, s), 4.50(2H, s), 6.65(2H, dd, J=0.9, 1.8 Hz), 6.84(2H, d, J=8.7 Hz), 7.44(2H, d, J=8.7 Hz), 7.75-7.78(2H, m), 7.94(1H, s).

2-(4-methoxybenzylsulfanyl)-9-methyl-6-(3-thienyl)-9H-purine (Compound 168)

¹H-NMR (CDCl₃) δ: 3.78(3H, s), 3.85(3H, s), 4.53(2H, s), 6.83(2H, d, J=8.4 Hz), 7.41-7.44(3H, m), 7.91(1H, s) 8.26 (1H, dd, J=1.2, 5.1 Hz), 8.87(1H, dd, J=1.2, 3.1 Hz).

6-(3,5-dimethylisoxazol-4-yl)-2-(4-methoxybenzylsulfanyl)-9-methyl-9H-purine (Compound 169)

¹H-NMR (CDCl₃) δ: 2.48(3H, s), 2.65(3H, s), 3.79(3H, s), 3.88(3H, s), 4.47(2H, s), 6.85(2H, d, J=8.4 Hz), 7.39(2H, d, J=8.4 Hz), 7.91(1H, s).

2-(4-methoxybenzylsulfanyl)-9-methyl-6-(pyrazol-4-yl)-9H-purine (Compound 170)

¹H-NMR (CDCl₃) δ: 3.78(3H, s), 3.87(3H, s), 4.51(2H, s), 6.85(2H, d, J=8.6 Hz), 7.43(2H, d, J=8.6 Hz), 7.88(1H, s), 8.70(2H, s).

2-(4-methoxybenzylsulfanyl)-9-methyl-6-(1-methylpyrazol-4-yl)-9H-purine (Compound 172)

¹H-NMR (CDCl₃) δ: 3.78(3H, s), 3.84(3H, s), 4.01(3H, s), 4.50(2H, s), 6.83(2H, d, J=8.6 Hz), 7.42(2H, d, J=8.6 Hz), 7.87(1H, s), 8.49(1H, s), 8.55(1H, s).

2-(3-amino-4-methoxybenzylsulfanyl)-9-methyl-6-(1-trans-propenyl)-9H-purine (Compound 173)

$^1$H-NMR (CDCl$_3$) δ: 2.05(3H, dd, J=1.8, 8.6 Hz), 3.81(3H, s), 3.82(3H, s), 4.44(2H, s), 6.69 (1H, m), 6.84(2H, m), 6.95 (1H, ddt, J=1.8, 8.6, 17.5 Hz), 7.60(1H, m), 7.84(1H, s).

2-(4-methoxybenzylsulfanyl)-9-methyl-6-(2-thienyl)-9H-purine (Compound 174)

$^1$H-NMR (CDCl$_3$) δ: 3.78(3H, s), 3.85(3H, s), 4.53(2H, s), 6.84(2H, d, J=8.7 Hz), 7.24(1H, m), 7.43(2H, d, J=8.7 Hz), 7.61(1H, d, J=4.9 Hz), 7.92(1H, s), 8.62(1H, d, J=3.7 Hz).

In addition, the compounds explained in the above examples (Compounds 1 to 174) and the structures thereof are shown in the above Table 1. The compound numbers in the table correspond to the compounds explained in the above examples (Compounds 1 to 174).

Next, the results of tests for verifying the effects of the compounds explained in the above examples (Compounds 1 to 174) shall be explained. In addition, the test compound numbers in each test correspond to the compounds explained in the above examples (Compounds 1 to 174).

Example 7

[Pharmacological Test 1: in vitro Antitumor Activity Test]
1) Antitumor Activity Against Various Tumor Cells
(Test Method)
i) Adhesive Cancer Cells WiDr cells (human colon cancer cells) subcultured in a culture medium composed of a MEM medium added with 10% fetal bovine serum, 25 mM HEPES and 0.1 mg/ml kanamycin under the conditions of 37° C. and 5% carbon dioxide gas were made into single floating cells by treating with trypsin/EDTA, and a single cell suspension of 3×10$^4$ cells per 1 ml was prepared using the MEM medium (added with 10% fetal bovine serum, 25 mM HEPES and 0.1 mg/ml kanamycin). After dissolving the test compounds in DMSO, they were diluted in a RPMI 1640 medium (added with 10% fetal bovine serum, 25 mM HEPES and 0.1 mg/ml kanamycin) and prepared so that the concentrations were 2.0×10$^{-9}$ to 2.0×10$^{-4}$ M.

0.1 ml of the cell suspension was placed into each well of 96-well microplates, cultured for 24 hours to allow the cells to adhere to the microplates, then 0.1 ml of the sample solutions were added, and cultured for 72 hours at 37° C. in 5% carbon dioxide gas.

Afterwards, the level of growth inhibition at various sample concentrations was obtained using XTT colorimetry, and concentrations at which growth was inhibited by 50% (GI$_{50}$ values [μM]) were calculated.

In addition, cells other than WiDr cells that were used, and the condition for preparing each single cell suspension were as follows.

A549 cells (human lung cancer cells): 2×10$^4$ cells/ml
PC-3 cells (human prostate cancer cells): 2×10$^4$ cells/ml
B16F10 cells (mouse melanoma [malignant melanoma] cells): 1×10$^4$ cells/ml ii) P388 Cells (Hematolotic Tumor)

P388 cells (mouse leukemia cells) passaged in the abdominal cavity of DBA/2 mice were extracted with ascitic fluid, and cultured in a RPMI 1640 medium (added with 10% fetal bovine serum, 25 mM HEPES, 0.1 mg/ml kanamycin and 5 μM 2-hydroxyethyldisulfide) at 37° C. in 5% carbon dioxide gas. After culturing for 16 hours, floating P388 cells were made into a single cell suspension of 4×10$^4$ cells per 1 ml using the same RPMI 1640 medium as given above. The test substances were dissolved in DMSO, then diluted in a RPMI 1640 medium (added with 10% fetal bovine serum, 25 mM HEPES and 0.1 mg/ml kanamycin) and prepared so that the concentrations were 2.0×10$^{-9}$ to 2.0×10$^{-4}$ M.

0.1 ml of the cell suspension was placed into each well of 96-well microplates, then 0.1 ml of the sample solutions were added, and cultured for 72 hours at 37° C. in 5% carbon dioxide gas.

Afterwards, the level of growth inhibition at various sample concentrations was obtained using XTT colorimetry, and concentrations at which growth was inhibited by 50% (GI$_{50}$ values [μM]) were calculated.
(Results)
Some of the results are shown in the table below.
In vitro Antitumor Activity (GI$_{50}$ Values)

TABLE 2

| Compound Number | P388 | PC-3 | B16F10 | WiDr | A549 |
| --- | --- | --- | --- | --- | --- |
| 1 | 0.29 | 0.28 | 0.41 | 0.35 | 0.56 |
| 2 | 0.11 | 0.10 | 0.30 | 0.30 | 0.14 |
| 6 | 0.72 | 0.60 | 1.16 | 0.94 | 0.87 |
| 7 | 0.12 | 0.14 | 0.34 | 0.25 | 0.13 |
| 8 | 1.02 | 0.61 | 1.70 | 1.47 | 2.20 |
| 9 | 0.30 | 0.38 | 1.17 | 0.40 | 0.57 |
| 10 | 1.28 | 0.89 | 1.82 | 1.25 | 1.69 |
| 11 | 0.67 | 0.40 | 1.49 | 1.04 | 1.16 |
| 12 | 1.25 | 0.85 | 3.91 | 1.24 | 1.89 |
| 14 | 0.20 | 0.16 | 0.34 | 0.26 | 0.12 |
| 15 | 0.87 | 0.82 | 1.80 | 1.16 | 2.28 |
| 16 | 0.85 | 0.91 | 1.68 | 1.22 | 1.75 |
| 17 | 0.36 | 0.46 | 1.29 | 0.51 | 0.76 |
| 18 | 0.35 | 0.69 | 1.09 | 3.14 | 0.95 |
| 19 | 0.32 | 0.40 | 0.45 | 4.04 | 0.45 |
| 20 | 0.08 | 0.04 | 0.32 | 0.08 | 0.16 |
| 21 | 0.10 | 0.14 | 0.34 | 0.14 | 0.22 |
| 22 | 0.95 | 0.64 | 1.61 | 1.19 | 1.25 |
| 23 | 0.23 | 0.13 | 0.50 | 0.44 | 0.25 |
| 24 | 0.20 | 0.26 | 0.44 | 0.21 | 0.32 |
| 25 | 0.68 | 1.13 | 1.38 | 0.82 | 0.95 |
| 26 | 0.07 | 0.11 | 0.34 | 0.08 | 0.11 |
| 27 | 0.67 | 0.65 | 1.34 | 0.92 | 0.58 |
| 28 | 0.81 | 0.99 | 1.14 | 1.20 | 0.90 |
| 45 | 0.09 | 0.15 | 0.28 | 0.83 | 0.12 |
| 49 | 0.29 | 0.46 | 1.34 | 0.39 | 0.32 |
| 50 | 0.38 | 0.62 | 1.43 | 1.02 | 0.89 |
| 51 | 0.07 | 0.10 | 0.38 | 0.14 | 0.10 |
| 55 | 1.05 | 0.78 | 1.39 | 1.39 | 1.34 |
| 60 | 0.61 | 0.87 | 1.00 | 1.30 | 1.40 |
| 61 | 0.33 | 0.89 | 0.84 | 0.46 | 0.52 |
| 63 | 1.50 | 0.87 | 1.90 | 3.30 | 1.60 |
| 64 | 0.38 | 0.45 | 0.38 | 0.31 | 0.48 |
| 69 | 0.11 | 0.12 | 0.20 | 0.15 | 0.15 |
| 71 | 0.08 | 0.05 | 0.11 | 0.08 | 0.10 |
| 72 | <0.04 | <0.04 | <0.04 | <0.04 | <0.04 |
| 73 | <0.04 | <0.04 | <0.04 | <0.04 | <0.04 |
| 75 | 0.38 | 0.56 | 0.38 | 0.38 | 0.52 |
| 78 | 0.91 | 0.36 | 1.20 | 1.10 | 1.10 |
| 79 | 1.0 | 0.44 | 1.50 | 1.30 | 1.40 |
| 80 | 0.07 | 0.07 | 0.21 | 0.16 | 0.14 |
| 82 | 0.11 | 0.30 | 0.30 | 0.21 | 0.14 |
| 83 | 0.09 | 0.18 | 0.18 | 0.14 | 0.15 |
| 84 | 0.26 | 0.98 | 0.51 | 1.90 | 0.55 |
| 85 | 0.07 | 0.12 | 0.12 | 0.08 | 0.14 |
| 86 | 0.03 | 0.05 | 0.06 | 0.04 | 0.05 |
| 87 | 0.02 | 0.04 | 0.08 | 0.04 | 0.05 |
| 89 | 0.11 | 0.21 | 0.13 | 0.12 | 0.15 |
| 90 | 0.52 | 1.73 | 1.10 | 1.37 | 0.72 |
| 91 | 0.09 | 0.34 | 0.14 | 0.09 | 0.14 |
| 94 | 0.08 | 0.11 | 0.14 | 0.08 | 0.10 |
| 97 | 0.09 | 0.12 | 0.29 | 0.30 | 0.14 |
| 99 | 0.96 | 5.95 | 1.98 | 1.29 | 1.18 |
| 100 | 3.29 | 0.15 | 4.63 | 6.11 | 3.90 |
| 102 | 0.72 | 0.83 | 1.42 | 0.92 | 0.83 |
| 103 | 0.17 | 0.13 | 0.32 | 0.28 | 0.23 |
| 105 | 0.24 | 0.56 | 0.41 | 0.26 | 0.24 |

TABLE 2-continued

| Compound Number | P388 | PC-3 | B16F10 | WiDr | A549 |
|---|---|---|---|---|---|
| 106 | 0.20 | 0.95 | 0.30 | 0.29 | 0.14 |
| 107 | 0.03 | 0.05 | 0.10 | 0.31 | 0.07 |
| 109 | 0.32 | 0.58 | 0.51 | 0.36 | 0.57 |
| 110 | 0.47 | 1.40 | 1.43 | 0.79 | 0.95 |
| 116 | 0.29 | 0.32 | 0.44 | 0.33 | 0.45 |
| 117 | 0.30 | 0.31 | 0.37 | 0.29 | 0.43 |
| 123 | 0.13 | 0.24 | 0.37 | 0.20 | 0.42 |
| 130 | 0.25 | 0.54 | 0.63 | 0.28 | 0.40 |
| 137 | 0.06 | 0.06 | 0.10 | 0.07 | 0.05 |
| 140 | 0.05 | 0.11 | 0.16 | 0.36 | 0.09 |
| 141 | 0.26 | 0.47 | 0.41 | 4.85 | 0.37 |
| 142 | 0.05 | 0.10 | 0.19 | 1.15 | 0.08 |
| 145 | <0.04 | 0.13 | 0.19 | 0.81 | 0.08 |
| 147 | 0.04 | 0.12 | 0.08 | 0.04 | 0.05 |
| 148 | 0.09 | 0.13 | 0.29 | 0.13 | 0.24 |
| 149 | 0.49 | 0.53 | 1.38 | 0.35 | 0.47 |
| 150 | 0.11 | 0.15 | 0.30 | 0.78 | 0.15 |
| 151 | 0.57 | 1.44 | 1.47 | 3.40 | 0.70 |
| 152 | <0.04 | <0.04 | <0.04 | <0.04 | <0.04 |
| 153 | <0.04 | <0.04 | <0.04 | <0.04 | <0.04 |
| 154 | 0.09 | 0.22 | 0.37 | 0.17 | 0.10 |
| 155 | 0.49 | 1.50 | 1.31 | 0.94 | 0.50 |
| 156 | 0.74 | 1.04 | 1.40 | 3.38 | 0.70 |
| 157 | 0.04 | 0.09 | 0.08 | 0.08 | 0.06 |
| 158 | 0.24 | 0.31 | 0.42 | 0.35 | 0.41 |
| 163 | 0.28 | 0.87 | 0.54 | 0.51 | 0.67 |
| 165 | 0.26 | 3.20 | 0.98 | 4.10 | 3.30 |
| 166 | 0.28 | 1.39 | 1.55 | 0.82 | 0.67 |
| 167 | 1.87 | 1.80 | 2.47 | 1.75 | 1.49 |
| 168 | 0.14 | 0.32 | 0.21 | 0.14 | 0.22 |
| 169 | <0.04 | 0.07 | 0.11 | 0.08 | <0.04 |
| 170 | <0.04 | 0.05 | 0.07 | <0.04 | <0.04 |
| 171 | 0.22 | 0.47 | 0.56 | 0.37 | 0.27 |
| 173 | 0.09 | 0.38 | 0.25 | 1.51 | 0.16 |
| A | 22.5 | >100 | 22.6 | 70 | >100 |
| B | >10.0 | >10.0 | >10.0 | >10.0 | >10.0 |
| C | >10.0 | >10.0 | >10.0 | >10.0 | >10.0 |

Additionally, Compound A: 6-mercaptopurine

Compound B: compound described in the document "Chemistry & Biology, Vol. 11, 135-146, January 2004:

[Chem. 21]

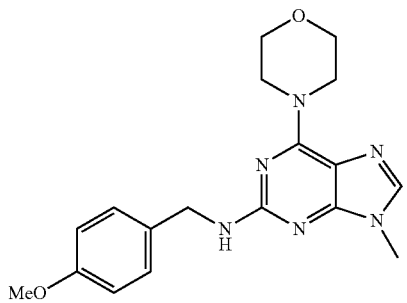

Compound C: compound described in the patent (WO 99/28321)

[Chem. 22]

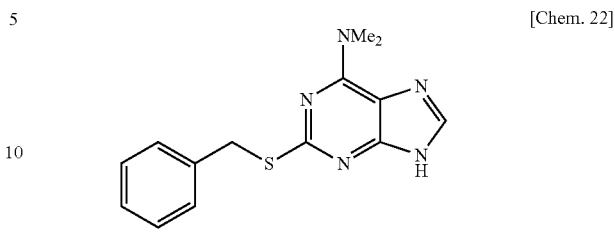

Based on the above results, it was confirmed that the compounds in the above table have higher antitumor activity than Compounds A to C, which are purine derivates having similar skeletons.

2) Antitumor Activity Against Breast Cancer Cells
(Test Method)

MCF-7 cells (human breast cancer cells) subcultured in a culture medium composed of a MEM medium added with 10% fetal bovine serum, 25 mM HEPES and 0.1 mg/ml kanamycin under the conditions of 37° C. and 5% carbon dioxide gas were made into single floating cells by treating with trypsin/EDTA, and a single cell suspension of $4 \times 10^4$ cells per 1 ml was prepared using the MEM medium (added with 10% fetal bovine serum, 25 mM HEPES and 0.1 mg/ml kanamycin). After dissolving the test substances (Compound 2 and Compound 7) in DMSO, they were diluted with the MEM medium (added with 10% fetal bovine serum, 25 mM HEPES and 0.1 mg/ml kanamycin) and prepared so that the concentrations were $6.4 \times 10^{-8}$ to $2.0 \times 10^{-5}$ M.

0.1 ml of the cell suspension was placed into each well of a 96-well microplate, cultured for 24 hours to allow the cells to adhere to the microplate, then 0.1 ml of the sample solutions were added, and cultured for 72 hours at 37° C. in 5% carbon dioxide gas.

Afterwards, the cells in each well were made single floating cells by treating with trypsin/EDTA, and the number of cells was counted using a cell counter to obtain the growth inhibition rate at various sample concentrations and calculate the concentrations at which growth was inhibited by 50% ($GI_{50}$ values [μM]).

(Results)

Compound 2 and Compound 7 dose-dependently inhibited the growth of MCF-7 cells, and the $GI_{50}$ values were 0.11 μM for Compound 2 and 0.13 μM for Compound 7.

Example 8

[Pharmacological Test 2: In Vivo Antitumor Activity Test]
1) Effects of Compound 2 and Compound 7 on Nude Mice Transplanted with Human Lung Cancer A549
(Test Method)

Tumor tissue fragments of human lung cancer A549 (3 mm×3 mm×3 mm) were transplanted subcutaneously into the chests of six-week-old female BALB/c-nu/nu mice, and sample administration started when the tumor volume reached at least approximately 100 mm³ (day 0). Compound 2 and Compound 7 were suspended in a 1% hydroxypropylcellulose (HPC [L]) solution using an agate mortar. 400 mg/kg of Compound 2 was orally administered daily from day 0 to day 13 (excluding day 3 and day 10, a total of 12 times). 400 mg/kg of Compound 7 was intraperitoneally administered daily from day 0 to day 13 (excluding day 4 and day 11, a total of 12 times). Tumor diameters were measured to calculate tumor volume (½×long diameter×short diameter×short diameter), and the tumor volume after 14 days (at day 14) from the start of sample administration was divided by the tumor volume at the start of the administration to calculate relative tumor growth rate. The percentage of the relative tumor growth rate of the control group with respect to the relative tumor growth rate of the group administered with Compound 2 or Compound 7 was taken as T/C (%).
(Results)
Compound 2 and Compound 7 significantly inhibited tumor growth, and their T/C was respectively 73.1% and 55.4%
2) Effect of Compound 2 on Nude Mice Transplanted with Human Prostate Cancer PC-3
(Test Method)
Tumor tissue fragments of human prostate cancer PC-3 (3 mm×3 mm×3 mm) were transplanted subcutaneously into the chests of six-week-old female BALB/c-nu/nu mice, and sample administration started when the tumor volume reached at least approximately 100 mm³ (day 0). Compound 2 was suspended in a 1% HPC (L) solution using an agate mortar. 400 mg/kg of Compound 2 was orally administered daily from day 0 to day 13 (excluding day 3 and day 10, a total of 12 times). Tumor diameters were measured to calculate tumor volume (½×long diameter×short diameter×short diameter), and the tumor volume after 14 days (at day 14) from the start of sample administration was divided by the tumor volume at the start of the administration to calculate relative tumor growth rate. The percentage of the relative tumor growth rate of the control group with respect to the relative tumor growth rate of the group administered with Compound 2 was taken as T/C (%).
(Results)
Compound 2 significantly inhibited tumor growth, and the T/C was 32.2%.
3) Effect of Compound 2 on Nude Mice Transplanted with Human Colon Cancer WiDr
(Test Method)
Tumor tissue fragments of human colon cancer WiDr (3 mm×3 mm×3 mm) were transplanted subcutaneously into the chests of six-week-old female BALB/c-nu/nu mice, and sample administration started when the tumor volume reached at least approximately 100 mm³ (day 0). Compound 2 was suspended in a 1% HPC (L) solution using an agate mortar. 400 mg/kg of Compound 2 was orally administered daily from day 0 to day 13 (excluding day 3 and day 10, a total of 12 times). Tumor diameters were measured to calculate tumor volume (½×long diameter×short diameter×short diameter), and the tumor volume after 14 days (at day 14) from the start of sample administration was divided by the tumor volume at the start of the administration to calculate relative tumor growth rate. The percentage of the relative tumor growth rate of the control group with respect to the relative tumor growth rate of the group administered with Compound 2 was taken as T/C (%).
(Results)
Compound 2 significantly inhibited tumor growth, and the T/C was 62.1%.
Based on the results of the above experiments, it was confirmed that the purine derivatives of the present invention provide superior effects as antitumor agents or anticancer agents.
The above examples illustratively explained the present invention with reference to examples, and those skilled in the art will understand that various modifications are possible and such modifications are also within the scope of the present invention. For example, in the above examples, concrete explanation was only made using some of the compounds on which test results were confirmed, and it is possible to apply compounds other than the compounds used in the above examples to diseases other than the types of cancers used in the examples, and that is also covered by the technical scope of the present invention.

The various embodiments explained above based on the descriptions of the modes for carrying out the invention are not disclosed for the purpose of limiting the present invention but for the purpose of illustration. The technical scope of the present invention is defined by the recitations of the claims, and those skilled in the art can make various design changes within the technical scope of the invention recited in the claims.

In addition, the disclosures of all patents, patent applications and documents cited in the present specification are incorporated in the present specification by reference.

The invention claimed is:
1. A compound represented by formula (I), or a pharmaceutically acceptable salt thereof:

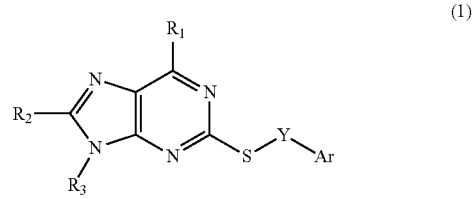

wherein
Ar represents a phenyl group, pyridyl group, thiazolyl group, benzofuranyl group, dihydrobenzofuranyl group, naphthalenyl group, imidazolyl group or pyrazolyl group, optionally independently substituted with one, two or three halogens, formyl groups, cyano groups, nitro groups, amino groups, hydroxyl groups or carboxyl groups; or with one, two or three (C1-C6) alkyl groups, (C2-C6) alkenyl groups, (C1-C6) alkylcarbonyl groups, (C1-C6) alkylamino groups, (C1-C6) alkylcarbonylaminocarbonyl groups, (C3-C6) cycloalkylamino groups, (C1-C7) alkoxycarbonylamino groups, di[(C1-C6)alkyl]amino groups, (C1-C6) alkylcarbonylamino groups, (C3-C6) cycloalkylcarbonylamino groups, di[(C1-C6) alkyl]aminocarbonylamino groups, di[(C1-C6) alkyl]aminothiocarbonylamino groups, heteroarylcarbonylamino groups, phenyloxycarbonylamino groups, phenylcarbonylamino groups, (C1-C6) alkylsulfonylamino groups, di[(C1-C6) alkyl]aminosulfonylamino groups, (C1-C6) alkoxy groups, (C1-C6) alkylthio groups, (C1-C6) alkylenedioxy groups, (C1-C6) alkoxycarbonyl groups, amino(C1-C6) alkylcarbonylamino groups, phenyl(C2-C6) alkenylcarbonylamino groups, (C1-C6) alkoxy(C1-C6) alkylcarbonylamino groups, (C1-C6) alkoxycarbonylamino(C1-C6) alkylcarbonylamino groups, phenyl groups or phenyl(C1-C6) alkoxy groups optionally substituted with a halogen, cyano group, amino group, hydroxyl group or carboxyl group;
Y represents a (C1-C6) alkylene group optionally comprising a carbonyl group in the carbon chain, one or two of Ar, or both;
$R_1$ represents a (C1-C6) alkyl group or (C2-C6) alkenyl group; or an amino group substituted with one or two (C1-C6) alkyl groups, (C1-C6) alkoxy groups, (C1-C6) alkoxy(C1-C6) alkyl groups, (C3-C6) cycloalkyl groups or (C2-C6) alkenyl groups; or a (C1-C6) alkylcarbonylamino group optionally substituted with one or two (C1-C6) alkyl groups, (C1-C6) alkoxy groups, (C1-C6) alkoxy(C1-C6) alkyl groups, (C3-C6) cycloalkyl groups or (C2-C6) alkenyl groups; or a heterocyclic group optionally substituted with one or two nitroso groups, formyl groups, hydroxyl groups, (C1-C6) alkyl groups, (C1-C6) alkylcarbonyl groups, (C1-C6) alkoxy groups, (C1-C6) alkoxycarbonyl groups or hydroxy (C1-C6) alkylamino groups; or a phenyl group substituted with a halogen, formyl group, cyano group, nitro group, amino group, hydroxyl group, or carboxyl group;

R$_2$ represents H; or a (C1-C6) alkyl group, (C2-C6) alkenyl group, (C2-C6) alkynyl group or (C3-C6) cycloalkyl group optionally substituted with one or two halogens, nitro groups or amino groups; and R$_3$ represents a (C1-C6) alkyl group, (C2-C6) alkenyl group, (C2-C6) alkynyl group, (C3-C6) cycloalkyl group, (C3-C6) cycloalkyl(C1-C6) alkyl group, amino (C1-C6) alkyl group, three- to five-membered ether-(C1-C6) alkyl group or (C1-C6) alkylcarbonylamino (C1-C6) alkyl group optionally substituted with a halogen or hydroxyl group.

2. The compound of claim 1, or a pharmaceutically acceptable salt thereof, wherein Ar is a phenyl group, naphthalenyl group or pyrazolyl group optionally independently substituted with one, two or three halogens, formyl groups, cyano groups, nitro groups, amino groups, hydroxyl groups or carboxyl groups; or with one, two or three (C1-C6) alkyl groups, (C2-C6) alkenyl groups, (C1-C6) alkoxycarbonylamino groups, di[(C1-C6) alkyl]amino groups, (C1-C6) alkylcarbonylamino groups, (C3-C6) cycloalkylcarbonylamino groups, di[(C1-C6) alkyl]aminocarbonylamino groups, heteroarylcarbonylamino groups, phenylcarbonylamino groups, di[(C1-C6) alkyl]aminosulfonylamino groups, (C1-C6) alkoxy groups, amino(C1-C6) alkylcarbonylamino groups, phenyl(C1-C6) alkoxy groups, (C1-C6) alkylthio groups, (C1-C6) alkylenedioxy groups, (C1-C6) alkoxycarbonyl groups or phenyl groups optionally substituted with a halogen.

3. The compound of claim 1, or a pharmaceutically acceptable salt thereof, wherein Ar is a phenyl group, naphthalenyl group or pyrazolyl group optionally independently substituted with one, two or three halogens, cyano groups, nitro groups, amino groups, hydroxyl groups, (C1-C6) alkyl groups, (C2-C6) alkenyl groups, (C1-C6) alkylcarbonylamino groups, heteroarylcarbonylamino groups, phenylcarbonylamino groups, di[(C1-C6) alkyl]aminosulfonylamino groups, (C1-C6) alkoxy groups, phenyl(C1-C6) alkoxy groups or amino(C1-C6) alkylcarbonylamino groups.

4. The compound of claim 1, or a pharmaceutically acceptable salt thereof, wherein Y is a (C1-C6) alkylene group.

5. The compound of claim 1, or a pharmaceutically acceptable salt thereof, R$_1$ is a (C2-C6) alkenyl group; or an amino group or (C1-C6) alkylcarbonylamino group optionally substituted with one or two (C1-C6) alkyl groups, (C1-C6) alkoxy groups or (C3-C6) cycloalkyl groups; or a heterocyclic group optionally substituted with one or two nitroso groups, (C1-C6) alkyl groups, (C1-C6) alkylcarbonyl groups or (C1-C6) alkoxycarbonyl groups.

6. The compound of claim 1, or a pharmaceutically acceptable salt thereof, wherein R$_1$ is an amino group or (C1-C6) alkylcarbonylamino group optionally substituted with one or two (C1-C6) alkyl groups or (C1-C6) alkoxy groups; or a heterocyclic group optionally substituted with one or two nitroso groups, (C1-C6) alkyl groups or (C1-C6) alkylcarbonyl groups.

7. The compound of claim 1, or a pharmaceutically acceptable salt thereof, wherein the heterocyclic group is a morpholino group, oxadinyl group, dihydrooxadinyl group, piperazinyl group, pyrrolinyl group, pyrrolyl group, imidazolyl group, pyrazolyl group, triazolyl group, oxazolyl group, isoxazolyl group, thienyl group or furyl group.

8. The compound of claim 1, or a pharmaceutically acceptable salt thereof, wherein the heterocyclic group is a morpholino group, dihydrooxadinyl group, pyrrolyl group, imidazolyl group, pyrazolyl group, isoxazolyl group or thienyl group.

9. The compound of claim 1, or a pharmaceutically acceptable salt thereof, wherein R$_2$ is H, a (C1-C6) alkyl group, (C2-C6) alkenyl group or (C3-C6) cycloalkyl group.

10. The compound of claim 1, or a pharmaceutically acceptable salt thereof, wherein R$_2$ is H, a (C1-C6) alkyl group or (C2-C6) alkenyl group.

11. The compound of claim 1, or a pharmaceutically acceptable salt thereof, wherein R$_3$ is a (C1-C6) alkyl group, (C2-C6) alkenyl group or acetylamino(C1-C6) alkyl group optionally substituted with a halogen or hydroxyl group.

12. The compound of claim 1, or a pharmaceutically acceptable salt thereof, wherein R$_3$ is a (C1-C6) alkyl group optionally substituted with a halogen or hydroxyl group.

13. The compound of claim 1, or a pharmaceutically acceptable salt thereof, wherein the compound is:

8-ethyl-2-(4-methoxybenzylsulfanyl)-9-methyl-6-morpholino-9H-purine;
2-(3-amino-4-methoxybenzylsulfanyl)-8-ethyl-9-methyl-6-morpholino-9H-purine;
2-(4-methoxybenzylsulfanyl)-8,9-dimethyl-6-morpholino-9H-purine;
2-(4-methoxybenzylsulfanyl)-9-methyl-6-morpholino-8-propyl-9H-purine;
8-ethyl-2-(4-methoxycarbonylbenzylsulfanyl)-9-methyl-6-morpholino-9H-purine;
8-ethyl-2-(4-methoxybenzylsulfanyl)-6-morpholino-9-propyl-9H-purine;
8-ethyl-2-(4-methoxybenzylsulfanyl)-9-methyl-6-(4-nitrosopiperazin-1-yl)-9H-purine;
8-ethyl-9-methyl-2-(4-methylbenzylsulfanyl)-6-morpholino-9H-purine;
2-(4-methoxybenzylsulfanyl)-9-methyl-6-morpholino-9H-purine;
8-ethyl-9-methyl-6-morpholino-2-(4-vinylbenzylsulfanyl)-9H-purine;
8-ethyl-2-(3-fluoro-4-methylbenzylsulfanyl)-9-methyl-6-morpholino-9H-purine;
8-ethyl-2-(4-ethylbenzylsulfanyl)-9-methyl-6-morpholino-9H-purine;
8-ethyl-2-(3-hydroxy-4-methoxybenzylsulfanyl)-9-methyl-6-morpholino-9H-purine;
8-ethyl-2-(3-fluoro-4-methoxybenzylsulfanyl)-9-methyl-6-morpholino-9H-purine;
2-(2-benzyloxy-4-methoxybenzylsulfanyl)-8-ethyl-9-methyl-6-morpholino-9H-purine;
2-(3-chloro-4-methoxybenzylsulfanyl)-8-ethyl-9-methyl-6-morpholino-9H-purine;
2-(4-ethoxybenzylsulfanyl)-8-ethyl-9-methyl-6-morpholino-9H-purine;
2-(3-amino-4-methoxybenzylsulfanyl)-9-methyl-6-morpholino-9H-purine;
2-(3-amino-4-methoxybenzylsulfanyl)-6-dimethylamino-9-methyl-9H-purine;
8-ethyl-2-(3-fluoro-4-methoxybenzylsulfanyl)-9-methyl-6-(4-nitrosopiperazin-1-yl)-9H-purine;
6-dimethylamino-2-(4-methoxybenzylsulfanyl)-9-methyl-9H-purine;

8-ethyl-2-(4-methoxybenzylsulfanyl)-9-methyl-6-[(3S)-3-methyl-4-nitrosopiperazin-1-yl]-9H-purine;
2-(3-amino-4-methoxybenzylsulfanyl)-6-dimethylamino-8-ethyl-9-methyl-9H-purine;
6-dimethylamino-8-ethyl-2-(4-methoxybenzylsulfanyl)-9-methyl-9H-purine;
6-diethylamino-2-(4-methoxybenzylsulfanyl)-9-methyl-9H-purine;
2-(4-methoxybenzylsulfanyl)-9-methyl-6-methylamino-9H-purine;
2-(3-acetylamino-4-methoxybenzylsulfanyl)-8-ethyl-9-methyl-6-morpholino-9H-purine;
2-[3-(2-aminoacetylamino)-4-methoxybenzylsulfanyl]-8-ethyl-9-methyl-6-morpholino-9H-purine hydrochloride;
9-(2-acetylaminoethyl)-8-ethyl-2-(4-methoxybenzylsulfanyl)-6-morpholino-9H-purine;
8-ethyl-9-(2-fluoroethyl)-2-(4-methoxybenzylsulfanyl)-6-morpholino-9H-purine;
8-ethyl-2-(4-fluoromethylbenzylsulfanyl)-9-methyl-6-morpholino-9H-purine;
8-ethyl-9-methyl-2-(4-methylsulfanylbenzylsulfanyl)-6-morpholino-9H-purine;
8-ethyl-2-(2-fluoro-4-methoxybenzylsulfanyl)-9-methyl-6-morpholino-9H-purine;
6-(4-acetylpiperazin-1-yl)-8-ethyl-2-(4-methoxybenzylsulfanyl)-9-methyl-9H-purine;
2-(4-dimethylaminobenzylsulfanyl)-8-ethyl-9-methyl-6-morpholino-9H-purine;
2-(benzo[1,3]dioxol-5-yl-methylsulfanyl)-8-ethyl-9-methyl-6-morpholino-9H-purine;
8-ethyl-2-(4-methoxy-3-methylbenzylsulfanyl)-9-methyl-6-morpholino-9H-purine;
8-ethyl-2-[1-(4-methoxyphenyl)ethylsulfanyl]-9-methyl-6-morpholino-9H-purine;
8-ethyl-2-(3-methoxycarbonylamino-4-methoxybenzylsulfanyl)-9-methyl-6-morpholino-9H-purine;
2-(3-amino-4-methylbenzylsulfanyl)-8-ethyl-9-methyl-6-morpholino-9H-purine;
2-(5-chloro-3-methyl-1-phenyl-1H-pyrazol-4-ylmethylsulfanyl)-8-ethyl-9-methyl-6-morpholino-9H-purine;
8-ethyl-2-(6-methoxynaphthalen-2-ylmethylsulfanyl)-9-methyl-6-morpholino-9H-purine;
8-ethyl-2-(4-methoxynaphthalen-1-ylmethylsulfanyl)-9-methyl-6-morpholino-9H-purine;
8-ethyl-2-[2-(4-methoxyphenyl)ethylsulfanyl]-9-methyl-6-morpholino-9H-purine;
2-(3-amino-4-methoxybenzylsulfanyl)-9-methyl-6-methylamino-9H-purine;
2-(4-bromobenzylsulfanyl)-8-ethyl-9-methyl-6-morpholino-9H-purine;
8-ethyl-2-[2-(4-fluorobenzoyl)ethylsulfanyl]-9-methyl-6-morpholino-9H-purine;
8-ethyl-2-[2-(4-methylbenzoyl)ethylsulfanyl]-9-methyl-6-morpholino-9H-purine;
8-ethyl-2(4-iodobenzylsulfanyl)-9-methyl-6-morpholino-9H-purine;
8-ethyl-2-[3-(4-methoxyphenyl)propylsulfanyl]-9-methyl-6-morpholino-9H-purine;
2-(3-cyano-4-methoxybenzylsulfanyl)-8-ethyl-9-methyl-6-morpholino-9H-purine;
8-ethyl-2-(4-methoxy-3-pivaloylaminobenzylsulfanyl)-9-methyl-6-morpholino-9H-purine;
8-ethyl-2-(4-methoxy-3-propionylaminobenzylsulfanyl)-9-methyl-6-morpholino-9H-purine;
2-(3-cyclopropancarbonylamino-4-methoxybenzylsulfanyl)-8-ethyl-9-methyl-6-morpholino-9H-purine;
8-ethyl-2-[3-(2-furylcarbonylamino)-4-methoxybenzylsulfanyl]-9-methyl-6-morpholino-9H-purine;
2-(3-dimethylaminocarbonylamino-4-methoxybenzylsulfanyl)-8-ethyl-9-methyl-6-morpholino-9H-purine;
2-(3-dimethylsulfamoylamino-4-methoxybenzylsulfanyl)-8-ethyl-9-methyl-6-morpholino-9H-purine;
2-(3-dimethylaminothiocarbonylamino-4-methoxybenzylsulfanyl)-8-ethyl-9-methyl-6-morpholino-9H-purine;
8-ethyl-2-[3-(4-fluorobenzoylamino)-4-methoxybenzylsulfanyl]-9-methyl-6-morpholino-9H-purine;
2-(3-acetylamino-4-methoxybenzylsulfanyl)-6-dimethylamino-8-ethyl-9-methyl-9H-purine;
6-(N-acetyl-N-methylamino)-2-(4-methoxybenzylsulfanyl)-9-methyl-9H-purine;
2-[3-(2-tert-butoxycarbonylaminoacetyl)amino-4-methoxybenzylsulfanyl]-8-ethyl-9-methyl-6-morpholino-9H-purine;
8-ethyl-2-(3-methoxyacetylamino-4-methoxybenzylsulfanyl)-9-methyl-6-morpholino-9H-purine;
6-ethylamino-2-(4-methoxybenzylsulfanyl)-9-methyl-9H-purine;
8-ethyl-6-(N-ethyl-N-methylamino)-2-(4-methoxybenzylsulfanyl)-9-methyl-9H-purine;
[2-(3-trans-cinnamoylamino)-4-methoxybenzylsulfanyl]-8-ethyl-9-methyl-6-morpholino-9H-purine;
2-(3-dimethylamino-4-methoxybenzylsulfanyl)-8-ethyl-9-methyl-6-morpholino-9H-purine;
8-ethyl-6-(N-ethyl-N-methylamino)-2-(4-iodobenzylsulfanyl)-9-methyl-9H-purine;
2-(3-cyano-4-methoxybenzylsulfanyl)-6-dimethylamino-8-ethyl-9-methyl-9H-purine;
2-[3-(iso-butoxycarbonylamino)-4-methoxybenzylsulfanyl]-8-ethyl-9-methyl-6-morpholino-9H-purine;
6-dimethylamino-8-ethyl-2-(3-fluoro-4-methoxybenzylsulfanyl)-9-methyl-9H-purine;
2-(3-cyano-4-methoxybenzylsulfanyl)-6-methylamino-9-methyl-9H-purine;
2-(3-fluoro-4-methoxybenzylsulfanyl)-6-methylamino-9-methyl-9H-purine;
6-diethylamino-8-ethyl-2-(4-methoxybenzylsulfanyl)-9-methyl-9H-purine;
6-(N-ethyl-N-methylamino)-2-(4-methoxybenzylsulfanyl)-9-methyl-9H-purine;
6-acetylamino-2-(4-methoxybenzylsulfanyl)-9-methyl-9H-purine;
8-ethyl-2-(3-heptoxycarbonylamino-4-methoxybenzylsulfanyl)-9-methyl-6-morpholino-9H-purine;
2-(3-bromo-4-methoxybenzylsulfanyl)-8-ethyl-9-methyl-6-morpholino-9H-purine;
8-ethyl-2-(4-methoxy-3-vinylbenzylsulfanyl)-9-methyl-6-morpholino-9H-purine;
2-(3-cyano-4-methoxybenzylsulfanyl)-9-methyl-6-morpholino-9H-purine;
8-ethyl-2-[3-(N-acetylcarbamoyl)-4-methoxybenzylsulfanyl]-9-methyl-6-morpholino-9H-purine;
6-(N-ethyl-N-methylamino)-2-(3-fluoro-4-methoxybenzylsulfanyl)-9-methyl-9H-purine;
2-(3-fluoro-4-methoxybenzylsulfanyl)-9-methyl-6-morpholino-9H-purine;
2-(3-amino-4-methoxybenzylsulfanyl)-6-(N-ethyl-N-methylamino)-9-methyl-9H-purine;
2-(3-cyano-4-methoxybenzylsulfanyl)-6-(N-ethyl-N-methylamino)-9-methyl-9H-purine;
6-dimethylamino-2-(3-fluoro-4-methoxybenzylsulfanyl)-9-methyl-9H-purine;

2-(3-cyano-4-methoxybenzylsulfanyl)-6-dimethylamino-9-methyl-9H-purine;
6-(2-ethoxymorpholino)-2-(4-methoxybenzylsulfanyl)-9-methyl-9H-purine;
2-(3-cyano-4-methoxybenzylsulfanyl)-6-ethylamino-9-methyl-9H-purine;
2-(3-amino-4-ethylbenzylsulfanyl)-8-ethyl-9-methyl-6-morpholino-9H-purine;
6-ethylamino-2-(3-fluoro-4-methoxybenzylsulfanyl)-9-methyl-9H-purine;
2-(3-amino-4-methoxybenzylsulfanyl)-6-ethylamino-9-methyl-9H-purine;
9-(2-cyclopropylmethyl)-2-(4-methoxybenzylsulfanyl)-6-morpholino-9H-purine;
2-(3-cyano-4-methoxybenzylsulfanyl)-8,9-diethyl-6-morpholino-9H-purine;
2-(4-methoxybenzylsulfanyl)-6-morpholino-9-oxiranylmethyl-9H-purine;
9-allyl-2-(4-methoxybenzylsulfanyl)-6-morpholino-9H-purine;
2-(3-amino-4-methoxybenzylsulfanyl)-8,9-diethyl-6-morpholino-9H-purine;
2-(4-methoxybenzylsulfanyl)-6-morpholino-9-propargyl-9H-purine;
2-(4-ethoxybenzylsulfanyl)-9-methyl-6-morpholino-9H-purine;
2-benzhydrylsulfanyl-8-ethyl-9-methyl-6-morpholino-9H-purine;
6-cyclopropylamino-2-(4-methoxybenzylsulfanyl)-9-methyl-9H-purine;
9-ethyl-2-(4-methoxybenzylsulfanyl)-8-methyl-6-morpholino-9H-purine;
2-(3-amino-4-ethoxybenzylsulfanyl)-8-ethyl-9-methyl-6-morpholino-9H-purine;
2-(4-methoxybenzylsulfanyl)-9-ethyl-6-morpholino-8-propyl-9H-purine;
6-(N-methoxy-N-methylamino)-2-(4-methoxybenzylsulfanyl)-9-methyl-9H-purine;
2-(3-amino-4-ethoxybenzylsulfanyl)-8,9-diethyl-6-morpholino-9H-purine;
2-(3-amino-4-ethoxybenzylsulfanyl)-9-methyl-6-methylamino-9H-purine;
2-(4-methoxybenzylsulfanyl)-6-[(2-methoxyethyl)-methyl-amino]-9-methyl-9H-purine;
9-methyl-2-(4-methoxybenzylsulfanyl)-6-(1-pyrrolyl)-9H-purine;
6-(imidazol-1-yl)-2-(4-methoxybenzylsulfanyl)-9-methyl-9H-purine;
6-(2-ethoxymorpholino)-8-ethyl-2-(4-methoxybenzylsulfanyl)-9-methyl-9H-purine;
3-[2-(4-methoxybenzylsulfanyl)-9-methyl-9H-purin-6-yl]-1-methyl-imidazolinium iodide;
2-(3-amino-4-propoxybenzylsulfanyl)-8-ethyl-9-methyl-6-morpholino-9H-purine;
2-(3-amino-4-ethoxybenzylsulfanyl)-9-methyl-6-morpholino-9H-purine;
8,9-diethyl-2-(3-iodo-4-methoxybenzylsulfanyl)-6-morpholino-9H-purine;
2-(4-ethoxy-3-fluorobenzylsulfanyl)-8-ethyl-9-methyl-6-morpholino-9H-purine;
8,9-diethyl-2-(4-ethoxy-3-fluorobenzylsulfanyl)-6-morpholino-9H-purine;
6-(2-ethoxymorpholino)-2-(4-methoxy-3-nitrobenzylsulfanyl)-9-methyl-9H-purine;
2-(3-amino-4-methoxybenzylsulfanyl)-6-(2-ethoxymorpholino)-9-ethyl-9H-purine;
2-(3-amino-4-methoxybenzylsulfanyl)-6-(2-ethoxymorpholino)-9-methyl-9H-purine;
2-(4-methoxybenzylsulfanyl)-9-methyl-6-(pyrazol-1-yl)-9H-purine;
2-(3-amino-4-ethoxybenzylsulfanyl)-9-ethyl-8-methyl-6-morpholino-9H-purine;
8,9-diethyl-2-(3-fluoro-4-methoxybenzylsulfanyl)-6-morpholino-9H-purine;
2-(4-methoxybenzylsulfanyl)-9-methyl-6-(1,2,4-triazol-1-yl)-9H-purine;
2-(3-amino-4-methoxybenzylsulfanyl)-9-ethyl-6-methylamino-9H-purine;
6-allylamino-2-(4-methoxybenzylsulfanyl)-9-methyl-9H-purine;
6-(N,N-diallylamino)-2-(4-methoxybenzylsulfanyl)-9-methyl-9H-purine;
2-(4-methoxybenzylsulfanyl)-9-methyl-6-(3-methylpyrrol-1-yl)-9H-purine;
6-(2-methoxymorpholino)-2-(4-methoxy-3-nitrobenzylsulfanyl)-9-methyl-9H-purine;
2-(4-methoxybenzylsulfanyl)-9-methyl-6-(3-pyrrolin-1-yl)-9H-purine;
6-(2-hydroxymorpholino)-2-(4-methoxy-3-nitrobenzylsulfanyl)-9-methyl-9H-purine;
2-(4-methoxybenzylsulfanyl)-9-methyl-6-morpholino-8-(1-propenyl)-9H-purine;
6-(2-ethoxymorpholino)-2-(3-fluoro-4-methoxybenzylsulfanyl)-9-methyl-9H-purine;
2-(3-cyano-4-methoxybenzylsulfanyl)-6-(2-ethoxymorpholino)-9-methyl-9H-purine;
6-(2-ethoxymorpholino)-9-ethyl-2-(3-fluoro-4-methoxybenzylsulfanyl)-9H-purine;
2-(3-amino-4-methoxybenzylsulfanyl)-6-dimethylamino-9-ethyl-9H-purine;
2-(3-fluoro-4-methoxybenzylsulfanyl)-6-(N-methoxy-N-methylamino)-9-methyl-9H-purine;
6-(2-ethoxymorpholino)-2-(4-ethoxy-3-nitrobenzylsulfanyl)-9-ethyl-9H-purine;
2-(4-methoxy-3-nitrobenzylsulfanyl)-9-methyl-6-(1-pyrrolyl)-9H-purine;
2-(3-amino-4-ethoxybenzylsulfanyl)-6-dimethylamino-9-methyl-9H-purine;
2-(3-amino-4-methoxybenzylsulfanyl)-9-methyl-6-(1-pyrrolyl)-9H-purine;
2-(4-methoxy-3-nitrobenzylsulfanyl)-9-methyl-6-(3-pyrrolin-1-yl)-9H-purine;
6-(N-methoxy-N-methylamino)-2-(4-methoxy-3-nitrobenzylsulfanyl)-9-methyl-9H-purine;
2-(3-amino-4-methoxybenzylsulfanyl)-9-methyl-6-(3-pyrrolin-1-yl)-9H-purine;
2-(3-amino-4-methoxybenzylsulfanyl)-6-(N-methoxy-N-methylamino)-9-methyl-9H-purine;
2-[2-(6-methoxynaphthalen-2-yl)-2-oxoethylsulfanyl]-8-ethyl-9-methyl-6-morpholino-9H-purine;
6-(2,3-dihydro-[1,4]oxadin-4-yl)-2-(4-methoxybenzylsulfanyl)-9-methyl-9H-purine;
6-(2,3-dihydro-[1,4]oxadin-4-yl)-8-ethyl-2-(4-methoxybenzylsulfanyl)-9-methyl-9H-purine;
6-(2,3-dihydro-[1,4]oxadin-4-yl)-2-(4-methoxy-3-nitrobenzylsulfanyl)-9-methyl-9H-purine;
2-(3-amino-4-methoxybenzylsulfanyl)-6-(2,3-dihydro-[1,4]oxadin-4-yl)-9-methyl-9H-purine;
2-(3-amino-4-methoxybenzylsulfanyl)-6-(2,3-dihydro-[1,4]oxadin-4-yl)-9-ethyl-9H-purine;
6-(2,3-dihydro-[1,4]oxadin-4-yl)-2-(3-fluoro-4-methoxybenzylsulfanyl)-9-methyl-9H-purine;

2-(3-cyano-4-methoxybenzylsulfanyl)-6-(2,3-dihydro-[1,4]oxadin-4-yl)-9-methyl-9H-purine;
6-(2,3-dihydro-[1,4]oxadin-4-yl)-9-ethyl-2-(3-fluoro-4-methoxybenzylsulfanyl)-9H-purine;
6-(2,3-dihydro-[1,4]oxadin-4-yl)-9-ethyl-2-(3-nitro-4-ethoxybenzylsulfanyl)-9H-purine;
2-(3-amino-4-ethoxybenzylsulfanyl)-6-(2,3-dihydro-[1,4]oxadin-4-yl)-9-ethyl-9H-purine;
6-(2,3-dihydro[1,4]oxadin-4-yl)-8-ethyl-2-(3-fluoro-4-methoxybenzylsulfanyl)-9-methyl-9H-purine;
8,9-diethyl-6-(2,3-dihydro-[1,4]oxadin-4-yl)-2-(4-methoxybenzylsulfanyl)-9H-purine;
6-(2,3-dihydro-[1,4]oxadin-4-yl)-2-(4-ethoxy-3-nitrobenzylsulfanyl)-9-methyl-9H-purine;
2-(3-amino-4-ethoxybenzylsulfanyl)-6-(2,3-dihydro-[1,4]oxadin-4-yl)-9-methyl-9H-purine;
2-(3-cyano-4-methoxybenzylsulfanyl)-6-(2,3-dihydro-[1,4]oxadin-4-yl)-8-ethyl-9-methyl-9H-purine;
2-(3-amino-4-methoxybenzylsulfanyl)-6-(2,3-dihydro-[1,4]oxadin-4-yl)-8-ethyl-9-methyl-9H-purine;
2-(4-methoxybenzylsulfanyl)-9-methyl-6-(1-trans-propenyl)-9H-purine;
2-(4-methoxybenzylsulfanyl)-9-methyl-6-propyl-9H-purine;
2-(4-methoxybenzylsulfanyl)-9-methyl-6-vinyl-9H-purine;
2-(4-methoxybenzylsulfanyl)-9-methyl-6-(4-nitrophenyl)-9H-purine;
6-(2-furyl)-2-(4-methoxybenzylsulfanyl)-9-methyl-9H-purine;
2-(4-methoxybenzylsulfanyl)-9-methyl-6-(3-thienyl)-9H-purine;
6-(3,5-dimethylisoxazol-4-yl)-2-(4-methoxybenzylsulfanyl)-9-methyl-9H-purine;
2-(4-methoxybenzylsulfanyl)-9-methyl-6-(pyrazol-4-yl)-9H-purine;
2-(4-methoxy-3-nitrobenzylsulfanyl)-9-methyl-6-(1-trans-propenyl)-9H-purine;
2-(4-methoxybenzylsulfanyl)-9-methyl-6-(1-methylpyrazol-4-yl)-9H-purine; or
2-(3-amino-4-methoxybenzylsulfanyl)-9-methyl-6-(1-trans-propenyl)-9H-purine;
2-(4-methoxybenzylsulfanyl)-9-methyl-6-(2-thienyl)-9H-purine.

14. A composition, comprising the compound of claim 1, or a pharmaceutically acceptable salt thereof, and a pharmaceutically acceptable adjuvant, diluent or carrier.

15. A pharmaceutical composition for treating tumor, comprising the compound of claim 1, or a pharmaceutically acceptable salt thereof.

\* \* \* \* \*